US009320644B2

(12) United States Patent
Kreck et al.

(10) Patent No.: US 9,320,644 B2
(45) Date of Patent: Apr. 26, 2016

(54) NON-INVASIVE SYSTEMS, DEVICES, AND METHODS FOR SELECTIVE BRAIN COOLING

(75) Inventors: Thomas Kreck, San Francisco, CA (US); Seth Rodgers, San Francisco, CA (US); Ian Sas, Maple Ridge (CA)

(73) Assignee: NEUROSAVE, INC., San Francisco, CA (US)

(*) Notice: Subject to any disclaimer, the term of this patent is extended or adjusted under 35 U.S.C. 154(b) by 563 days.

(21) Appl. No.: 13/558,108

(22) Filed: Jul. 25, 2012

(65) Prior Publication Data

US 2013/0030411 A1    Jan. 31, 2013

Related U.S. Application Data

(60) Provisional application No. 61/511,409, filed on Jul. 25, 2011.

(51) Int. Cl.
*A61M 31/00* (2006.01)
*A61F 7/12* (2006.01)
*A61M 19/00* (2006.01)
A61F 7/00 (2006.01)
A61F 7/02 (2006.01)
A61M 16/04 (2006.01)

(52) U.S. Cl.
CPC .............. *A61F 7/12* (2013.01); *A61M 16/0459* (2014.02); *A61M 16/0479* (2014.02); *A61M 19/00* (2013.01); *A61F 2007/0063* (2013.01); *A61F 2007/0288* (2013.01); *A61M 16/04* (2013.01); *A61M 2205/3606* (2013.01); *A61M 2210/0618* (2013.01)

(58) Field of Classification Search
CPC ................ A61F 2007/0056; A61F 2007/0063; A61M 2205/3606; A61M 19/00; A61M 3/0229
See application file for complete search history.

(56) References Cited

U.S. PATENT DOCUMENTS

| 3,897,790 | A | 8/1975 | Magilton et al. .............. 607/105 |
| 5,149,321 | A | 9/1992 | Klatz et al. ..................... 604/500 |
| 5,474,533 | A | 12/1995 | Ward et al. ...................... 604/26 |

(Continued)

FOREIGN PATENT DOCUMENTS

| EP | 0382787 | 11/1989 |
| EP | 0382787 | 3/1995 |

(Continued)

OTHER PUBLICATIONS

International Preliminary Report on Patentability issued in International Application No. PCT/US2012/048160, dated Feb. 6, 2014.

(Continued)

*Primary Examiner* — Emily Schmidt
(74) *Attorney, Agent, or Firm* — Norton Rose Fulbright US LLP

(57) ABSTRACT

Methods, systems, and devices are disclosed for providing selective and non-selective cooling and warming of a patient. Multiple embodiments of devices are disclosed for performing rapid induction and maintenance of therapeutic hypothermia either in a hospital setting or in the field so that hypothermic treatment can be quickly instituted before significant tissue damage occurs. Methods are also disclosed for targeting brain cooling by irrigating the upper airway, aerodigestive tract, and/or more generalized cooling by irrigating the esophagus and/or stomach.

35 Claims, 34 Drawing Sheets

(56) References Cited

U.S. PATENT DOCUMENTS

| | | | |
|---|---|---|---|
| 5,522,870 A | 6/1996 | Ben-Zion | 607/104 |
| 5,531,776 A | 7/1996 | Ward et al. | 607/105 |
| 5,755,756 A | 5/1998 | Freedman et al. | 607/110 |
| 5,908,870 A | 6/1999 | McLeod | 514/771 |
| 5,916,242 A | 6/1999 | Schwartz | 607/113 |
| 5,927,273 A | 7/1999 | Federowicz et al. | 128/200.24 |
| 5,989,238 A | 11/1999 | Ginsburg | 604/500 |
| 6,007,571 A | 12/1999 | Neilson et al. | 607/105 |
| 6,030,412 A | 2/2000 | Klatz et al. | 607/104 |
| 6,033,383 A | 3/2000 | Ginsburg | 604/113 |
| 6,051,019 A | 4/2000 | Dobak | 607/104 |
| 6,126,680 A | 10/2000 | Wass | 607/96 |
| 6,126,684 A | 10/2000 | Gobin et al. | 607/113 |
| 6,149,624 A | 11/2000 | McShane | 604/113 |
| 6,149,677 A | 11/2000 | Dobak | 607/106 |
| 6,149,962 A | 11/2000 | Loh et al. | 426/573 |
| 6,156,057 A | 12/2000 | Fox | 607/96 |
| 6,231,594 B1 | 5/2001 | Dae | 607/96 |
| 6,290,717 B1 | 9/2001 | Philips | 607/113 |
| 6,411,852 B1 | 6/2002 | Danek et al. | 607/42 |
| 6,416,532 B1 | 7/2002 | Fallik | 607/109 |
| 6,436,071 B1 | 8/2002 | Schwartz | 604/113 |
| 6,447,474 B1 | 9/2002 | Balding | 604/66 |
| 6,485,450 B1 | 11/2002 | Owen | 604/24 |
| 6,497,721 B2 | 12/2002 | Ginsburg et al. | 607/106 |
| 6,511,502 B2 | 1/2003 | Fletcher | 607/109 |
| 6,527,798 B2 | 3/2003 | Ginsburg et al. | 607/106 |
| 6,533,804 B2 | 3/2003 | Dobak et al. | 607/105 |
| 6,547,811 B1 | 4/2003 | Becker et al. | 607/105 |
| 6,558,412 B2 | 5/2003 | Dobak | 607/105 |
| 6,592,612 B1 | 7/2003 | Samson et al. | 607/105 |
| 6,620,131 B2 | 9/2003 | Pham et al. | 604/113 |
| 6,645,233 B1 | 11/2003 | Ayers et al. | 607/105 |
| 6,648,906 B2 | 11/2003 | Lasheras et al. | 607/105 |
| 6,676,688 B2 | 1/2004 | Dobak et al. | 607/105 |
| 6,682,552 B2 | 1/2004 | Ramsden et al. | 607/109 |
| 6,702,840 B2 | 3/2004 | Keller et al. | 607/105 |
| 6,726,708 B2 | 4/2004 | Lasheras | 607/105 |
| 6,726,709 B1 | 4/2004 | Lennox | 607/105 |
| 6,730,115 B1 | 5/2004 | Heaton | 607/104 |
| 6,743,250 B2 | 6/2004 | Renfro | 607/104 |
| 6,758,832 B2 | 7/2004 | Barbut et al. | 604/113 |
| 6,827,898 B1 | 12/2004 | Fausset et al. | 422/46 |
| 6,846,322 B2 | 1/2005 | Kane et al. | 607/111 |
| 6,849,063 B1 | 2/2005 | Eshel et al. | 604/113 |
| 6,849,072 B2 | 2/2005 | Lee et al. | 606/21 |
| 6,849,083 B2 | 2/2005 | Ginsburg | 607/96 |
| 6,887,262 B2 | 5/2005 | Dobak et al. | 607/105 |
| 6,918,924 B2 | 7/2005 | Lasheras et al. | 607/105 |
| 6,929,656 B1 | 8/2005 | Lennox | 607/105 |
| 6,942,686 B1 | 9/2005 | Barbut et al. | 607/105 |
| 6,962,601 B2 | 11/2005 | Becker et al. | 607/105 |
| 6,983,749 B2 | 1/2006 | Kumar et al. | 128/204.15 |
| 6,986,783 B2 | 1/2006 | Gunn et al. | 607/110 |
| 7,044,960 B2 | 5/2006 | Voorhees et al. | 607/96 |
| 7,056,282 B2 | 6/2006 | Chester et al. | 600/107 |
| 7,066,947 B2 | 6/2006 | Nest et al. | 607/105 |
| 7,077,858 B2 | 7/2006 | Fletcher et al. | 607/104 |
| 7,087,075 B2 | 8/2006 | Briscoe et al. | 607/104 |
| 7,089,995 B2 | 8/2006 | Koscheyev et al. | 165/46 |
| 7,118,591 B2 | 10/2006 | Frank et al. | 607/105 |
| 7,144,418 B1 | 12/2006 | Lennox | 607/105 |
| 7,172,586 B1 | 2/2007 | Dae et al. | 604/500 |
| 7,175,649 B2 | 2/2007 | Machold et al. | 607/104 |
| 7,179,279 B2 | 2/2007 | Radons et al. | 607/108 |
| 7,189,253 B2 | 3/2007 | Lunderqvist et al. | 607/105 |
| 7,204,833 B1 | 4/2007 | Osorio et al. | 606/22 |
| RE39,651 E | 5/2007 | Schwartz | 607/113 |
| 7,217,282 B2 | 5/2007 | Ginsburg et al. | 607/96 |
| 7,232,458 B2 | 6/2007 | Saadat | 607/105 |
| 7,241,307 B2 | 7/2007 | Lennox | 607/104 |
| 7,258,662 B2 | 8/2007 | Machold et al. | 600/104 |
| 7,300,453 B2 | 11/2007 | Yon | 607/106 |
| 7,318,834 B2 | 1/2008 | Njemanze | 607/105 |
| 7,422,601 B2 | 9/2008 | Becker et al. | 607/105 |
| 7,458,984 B2 | 12/2008 | Yon et al. | 607/106 |
| 7,494,504 B2 | 2/2009 | Ginsburg et al. | 607/113 |
| 7,604,631 B2 | 10/2009 | Reynolds | 606/20 |
| 7,637,931 B2 | 12/2009 | Heaton | 607/104 |
| 7,641,632 B2 | 1/2010 | Noda et al. | 604/113 |
| 7,758,623 B2 | 7/2010 | Dzeng et al. | 607/105 |
| 7,771,460 B2 | 8/2010 | Ginsburg et al. | 607/96 |
| 7,806,915 B2 | 10/2010 | Scott et al. | 607/106 |
| 7,850,721 B2 | 12/2010 | Gonzales | 607/96 |
| 7,892,269 B2 | 2/2011 | Collins et al. | 607/104 |
| 7,896,009 B2 | 3/2011 | Stull | 128/898 |
| 7,909,861 B2 | 3/2011 | Balachandran et al. | 607/104 |
| 7,914,564 B2 | 3/2011 | Magers et al. | 607/106 |
| 7,922,752 B2 | 4/2011 | Dobak et al. | 607/106 |
| 7,930,772 B2 | 4/2011 | Fontanez | 2/425 |
| 7,963,986 B2 | 6/2011 | Machold et al. | 607/105 |
| 8,066,752 B2 | 11/2011 | Hamilton et al. | 607/111 |
| RE43,007 E | 12/2011 | Lalonde et al. | 606/22 |
| 8,123,789 B2 | 2/2012 | Khanna | 607/105 |
| 8,167,923 B2 | 5/2012 | Barbut et al. | 607/105 |
| 8,172,788 B2 | 5/2012 | Koninckx et al. | 604/26 |
| 8,182,520 B2 | 5/2012 | Schock et al. | 607/108 |
| 8,221,481 B2 | 7/2012 | Takeda et al. | 607/105 |
| 8,231,664 B2 | 7/2012 | Kulstad et al. | 607/105 |
| 8,236,038 B2 | 8/2012 | Nofzinger | 607/109 |
| 8,257,340 B2 | 9/2012 | Saab | 604/509 |
| 8,267,878 B2 | 9/2012 | Sandhu et al. | 602/18 |
| 8,267,983 B2 | 9/2012 | Rogers et al. | 607/104 |
| 8,273,114 B2 | 9/2012 | Wasowski | 607/104 |
| 8,308,786 B2 | 11/2012 | Rozenberg et al. | 607/105 |
| 8,361,132 B2 | 1/2013 | Arad | 607/96 |
| 8,382,746 B2 | 2/2013 | Williams et al. | 606/21 |
| 8,388,577 B2 | 3/2013 | Noda et al. | 604/113 |
| 8,435,277 B2 | 5/2013 | Schock et al. | 607/104 |
| 8,435,278 B2 | 5/2013 | Callister et al. | 607/105 |
| 8,439,960 B2 | 5/2013 | Burnett et al. | 607/105 |
| 8,449,590 B2 | 5/2013 | Brader | 607/110 |
| 8,475,509 B2 | 7/2013 | Dae | 607/105 |
| 8,506,494 B2 | 8/2013 | Ginsburg | 600/481 |
| 8,512,280 B2 | 8/2013 | Rozenberg et al. | 604/94.01 |
| 8,512,387 B2 | 8/2013 | Fishel | 607/113 |
| 8,522,786 B2 | 9/2013 | Takeda et al. | 128/207.14 |
| 8,529,612 B2 | 9/2013 | Singh | 607/105 |
| 8,551,151 B2 | 10/2013 | Machold et al. | 607/105 |
| 8,568,464 B2 | 10/2013 | Dae et al. | 607/105 |
| 8,603,151 B2 | 12/2013 | Latham | 607/112 |
| 8,617,230 B2 | 12/2013 | Diller et al. | 607/108 |
| 8,652,189 B2 | 2/2014 | Gafni et al. | 607/96 |
| 8,663,211 B2 | 3/2014 | Fourkas et al. | 606/21 |
| 8,690,826 B2 | 4/2014 | Noda et al. | 604/113 |
| 8,696,725 B2 | 4/2014 | Kulstad et al. | 607/105 |
| 8,721,699 B2 | 5/2014 | Barbut et al. | 607/105 |
| 8,740,959 B2 | 6/2014 | Machold et al. | 607/104 |
| 8,771,329 B2 | 7/2014 | Christensen et al. | 607/96 |
| 8,808,241 B2 | 8/2014 | DiMeo et al. | 604/113 |
| 8,834,404 B2 | 9/2014 | Beaudin | 604/6.13 |
| 8,900,170 B1 | 12/2014 | Elkins | 602/2 |
| 8,905,968 B2 | 12/2014 | Thomas | 604/113 |
| 8,911,485 B2 | 12/2014 | Brian et al. | 607/105 |
| 8,932,339 B2 | 1/2015 | Harikrishna et al. | 607/107 |
| 9,004,066 B2 | 4/2015 | Belson | 128/204.15 |
| 2002/0151945 A1 | 10/2002 | Gobin et al. | 607/105 |
| 2003/0028137 A1* | 2/2003 | Levin | 604/8 |
| 2003/0208156 A1 | 11/2003 | Pham et al. | 604/113 |
| 2004/0199114 A1 | 10/2004 | Noda | 604/113 |
| 2004/0267338 A1 | 12/2004 | Harrison | 607/105 |
| 2005/0065584 A1 | 3/2005 | Schiff et al. | 607/105 |
| 2005/0107741 A1 | 5/2005 | Willard et al. | 604/113 |
| 2005/0222652 A1 | 10/2005 | Mori | 607/105 |
| 2006/0111764 A1 | 5/2006 | Kirkman | 607/104 |
| 2006/0175543 A1 | 8/2006 | Elefteriades | 250/231.13 |
| 2006/0276552 A1 | 12/2006 | Barbut et al. | 514/743 |
| 2007/0055328 A1 | 3/2007 | Mayse et al. | 607/105 |
| 2007/0225781 A1 | 9/2007 | Saadat et al. | 607/105 |
| 2008/0027523 A1 | 1/2008 | Behringer et al. | 607/109 |
| 2008/0243112 A1 | 10/2008 | De Neve | 606/28 |
| 2008/0269852 A1 | 10/2008 | Lennox et al. | 607/104 |
| 2009/0165786 A1 | 7/2009 | Barbut et al. | 128/203.12 |
| 2009/0177258 A1 | 7/2009 | Takeda et al. | 607/105 |

(56) References Cited

U.S. PATENT DOCUMENTS

| | | | |
|---|---|---|---|
| 2010/0100161 A1 | 4/2010 | Barbut et al. | 607/96 |
| 2010/0121159 A1 | 5/2010 | Burnett et al. | 600/301 |
| 2010/0174278 A1 | 7/2010 | Barbut et al. | 606/21 |
| 2010/0198319 A1 | 8/2010 | Arad | 607/105 |
| 2010/0204765 A1 | 8/2010 | Hall et al. | 607/105 |
| 2010/0211140 A1 | 8/2010 | Barbut et al. | 607/105 |
| 2010/0292765 A1 | 11/2010 | Etwil | 607/105 |
| 2010/0312315 A1 | 12/2010 | Etwil | 607/105 |
| 2010/0324483 A1 | 12/2010 | Rozenberg et al. | 604/98.01 |
| 2010/0324635 A1 | 12/2010 | Kreck | 607/105 |
| 2011/0125053 A1 | 5/2011 | Kulstad et al. | 600/561 |
| 2011/0125233 A1 | 5/2011 | Shen et al. | 607/105 |
| 2011/0125234 A1 | 5/2011 | Kulstad et al. | 607/105 |
| 2011/0130811 A1 | 6/2011 | Kulstad et al. | 607/105 |
| 2011/0208276 A1 | 8/2011 | Machold et al. | 607/104 |
| 2011/0275935 A1 | 11/2011 | Ginsburg et al. | 600/433 |
| 2011/0295163 A1 | 12/2011 | Vijayanagar | 601/18 |
| 2011/0319748 A1 | 12/2011 | Bronskill et al. | 600/420 |
| 2012/0029408 A1* | 2/2012 | Beaudin | 604/4.01 |
| 2012/0031405 A1 | 2/2012 | Geist et al. | 128/204.15 |
| 2012/0095537 A1 | 4/2012 | Hall et al. | 607/105 |
| 2012/0123509 A1 | 5/2012 | Merrill et al. | 607/105 |
| 2012/0136343 A1 | 5/2012 | Burnett | 606/21 |
| 2012/0265172 A1 | 10/2012 | Kulstad et al. | 604/540 |
| 2012/0288848 A1 | 11/2012 | Latham et al. | 435/1.1 |
| 2012/0310312 A1 | 12/2012 | Yee | 607/105 |
| 2012/0323296 A1 | 12/2012 | Takeda et al. | 607/105 |
| 2013/0000642 A1 | 1/2013 | Fearnot et al. | 128/204.15 |
| 2013/0030411 A1 | 1/2013 | Kreck et al. | 604/514 |
| 2013/0041439 A1 | 2/2013 | Gallagher | 607/109 |
| 2013/0090708 A1 | 4/2013 | Dabrowiak et al. | 607/105 |
| 2013/0090709 A1 | 4/2013 | Machold et al. | 607/106 |
| 2013/0172966 A1 | 7/2013 | Arad et al. | 607/105 |
| 2013/0296772 A1 | 11/2013 | Albalat | 604/28 |
| 2013/0302445 A1 | 11/2013 | Barbut et al. | 424/700 |
| 2013/0317578 A1 | 11/2013 | Diller et al. | 607/104 |
| 2013/0325089 A1 | 12/2013 | Divani et al. | 607/104 |
| 2014/0052224 A1 | 2/2014 | Kassab et al. | 607/105 |
| 2014/0067026 A1 | 3/2014 | Kulstad et al. | 607/104 |
| 2014/0194959 A1 | 7/2014 | Fries et al. | 607/104 |
| 2014/0194961 A1 | 7/2014 | Evans | 607/112 |
| 2014/0249466 A1 | 9/2014 | Hakim | 604/20 |
| 2014/0277305 A1 | 9/2014 | Kulstad et al. | 607/105 |
| 2014/0330197 A1 | 11/2014 | Fontaine | 604/23 |
| 2015/0018667 A1 | 1/2015 | Radman et al. | 600/411 |
| 2015/0018764 A1 | 1/2015 | Park et al. | 604/113 |
| 2015/0025607 A1 | 1/2015 | Lim et al. | 607/105 |
| 2015/0051673 A1 | 2/2015 | Rivas | 607/107 |
| 2015/0105687 A1 | 4/2015 | Abreu | 600/549 |
| 2015/0119962 A1 | 4/2015 | Kulstad et al. | 607/105 |

FOREIGN PATENT DOCUMENTS

| | | | |
|---|---|---|---|
| EP | 1061977 | 6/2002 | |
| EP | 1104272 | 10/2002 | |
| EP | 1301153 | 4/2003 | |
| EP | 1459714 | 9/2004 | |
| EP | 1631222 | 1/2007 | |
| EP | 1107714 | 2/2007 | |
| EP | 1301151 | 5/2007 | |
| EP | 1898850 | 3/2008 | |
| EP | 1820480 | 5/2009 | |
| EP | 1596791 | 7/2011 | |
| EP | 1731118 | 10/2011 | |
| EP | 1915943 | 10/2012 | |
| EP | 1729702 | 9/2013 | |
| EP | 2117485 | 9/2013 | |
| EP | 1935382 | 4/2014 | |
| EP | 2162186 | 9/2014 | |
| JP | 2000245764 | 9/2000 | |
| JP | 3702295 | 7/2005 | |
| JP | 4658758 | 1/2011 | |
| JP | 4738595 | 5/2011 | |
| JP | 4871256 | 11/2011 | |
| JP | 2012080996 | 4/2012 | |
| JP | 5124724 | 11/2012 | |
| JP | 5468414 | 2/2014 | |
| WO | WO 99/47191 | 9/1999 | |
| WO | WO 01/76655 | 10/2001 | |
| WO | WO 2005/087156 | 9/2005 | |
| WO | WO 2006/124702 | 11/2006 | |
| WO | WO 2009/094601 | 7/2009 | |
| WO | WO 2009094601 A2 * | 7/2009 | A61M 19/00 |
| WO | WO 2013/102051 | 7/2013 | |

OTHER PUBLICATIONS

International Search Report and Written Opinion issued in PCT Application PCT/US2012/048160, dated Feb. 28, 2013.

U.S. Appl. No. 61/697,112, "Devices, Systems and Methods for Controlling Pediatric Subjects", Sep. 2012. (not yet published).

Supplemental Search Report issued in European Patent Application No. 12816860, dated Oct. 2, 2015.

Office Action issued in Chinese Application No. 201280046676.3 on Jul. 28, 2015.

* cited by examiner

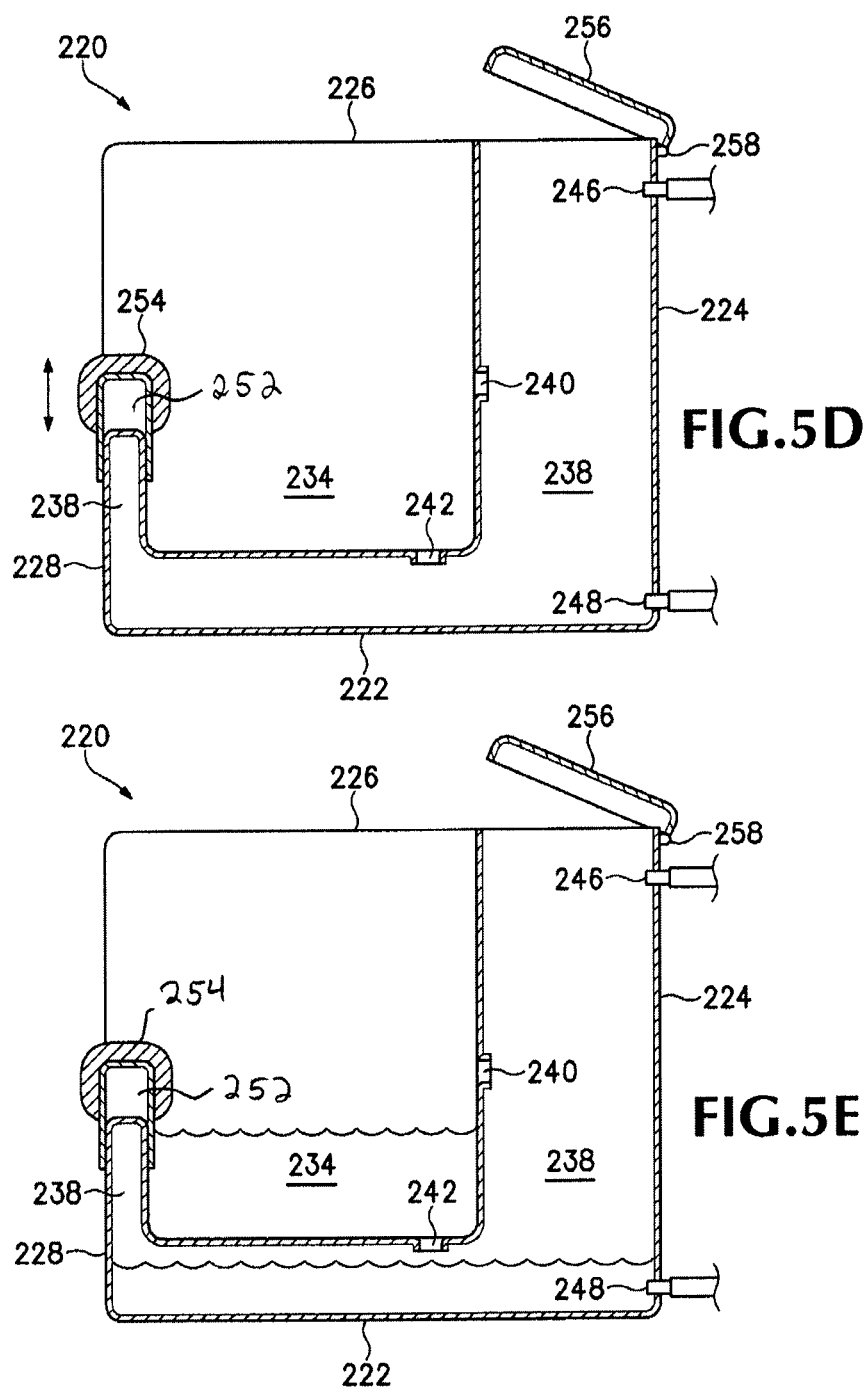

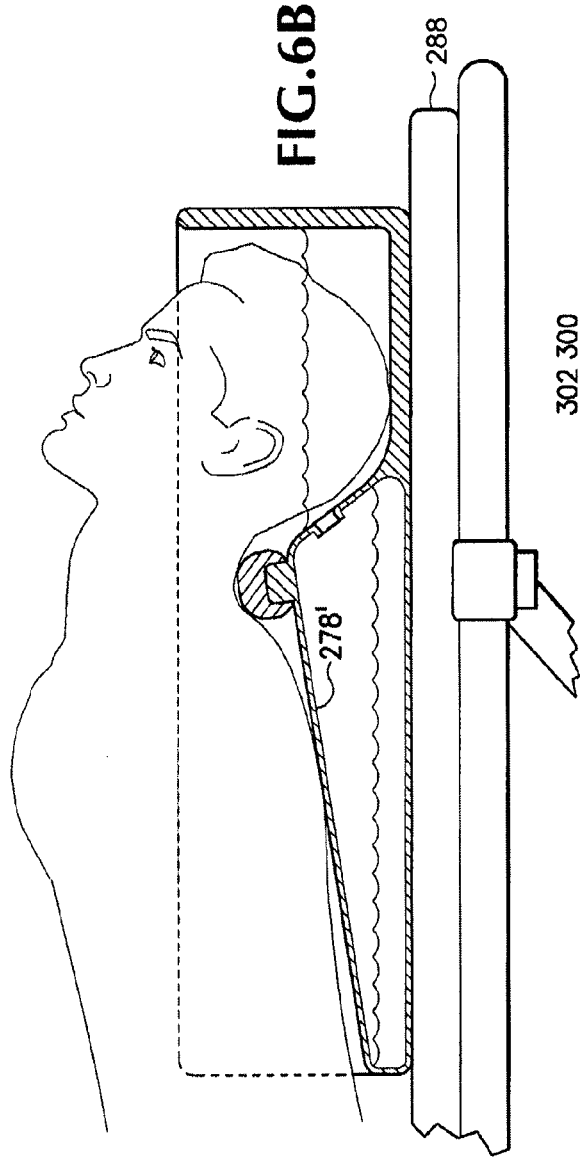

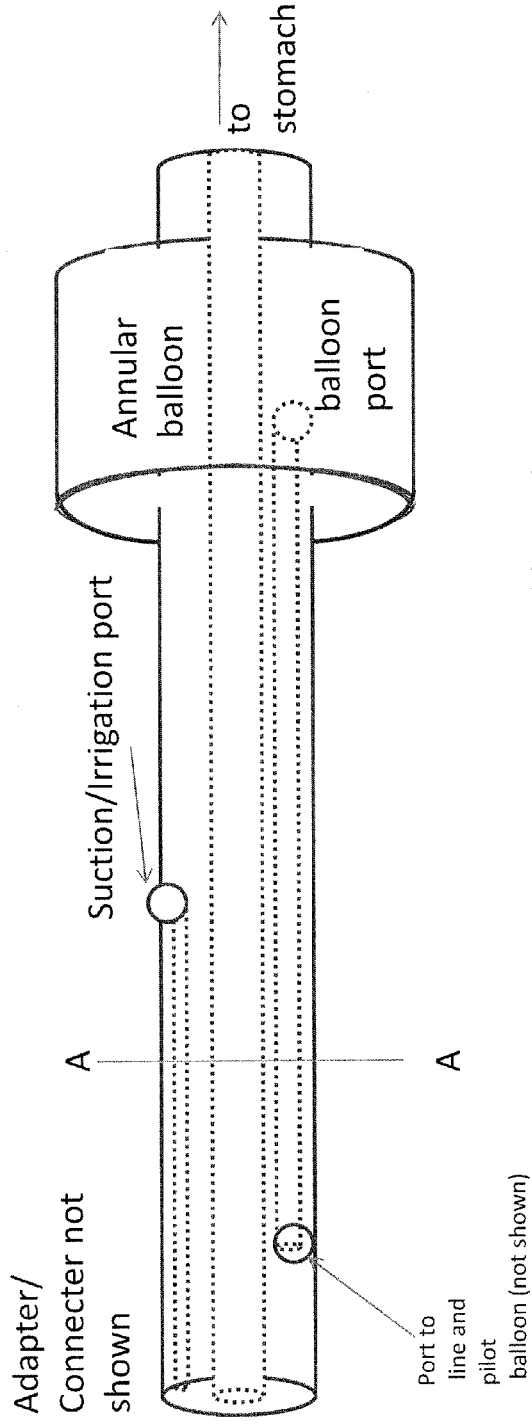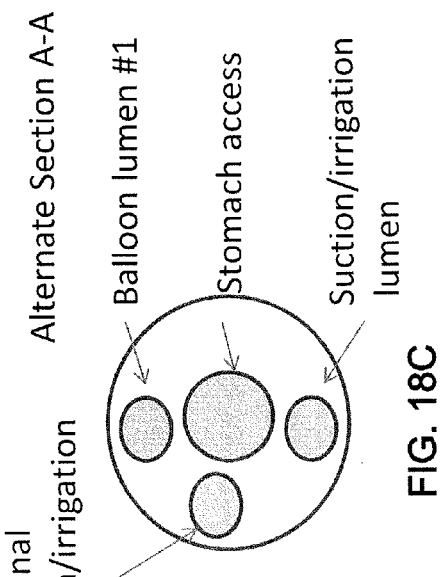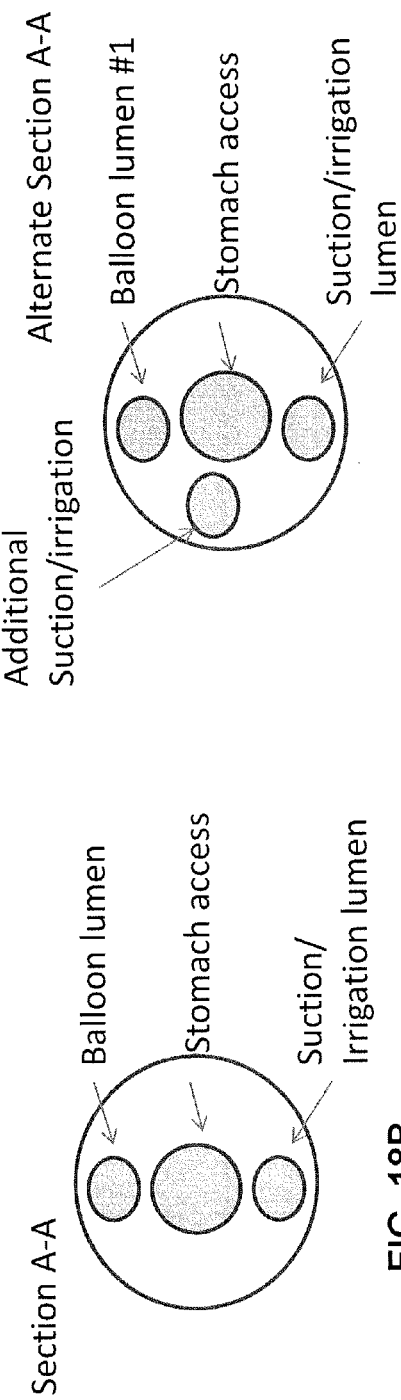

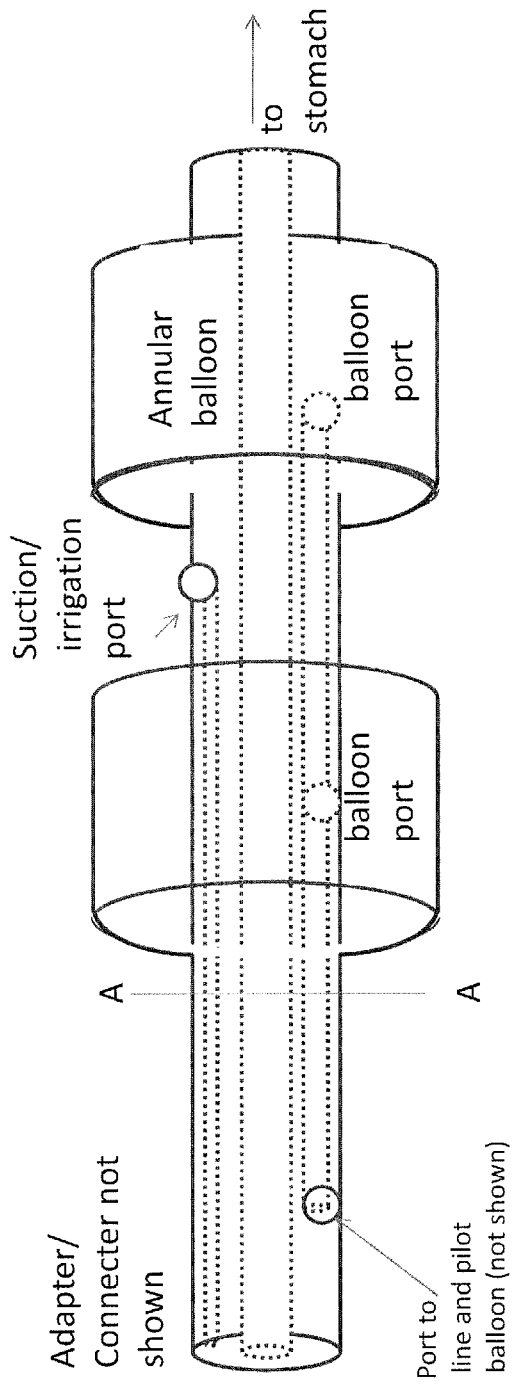
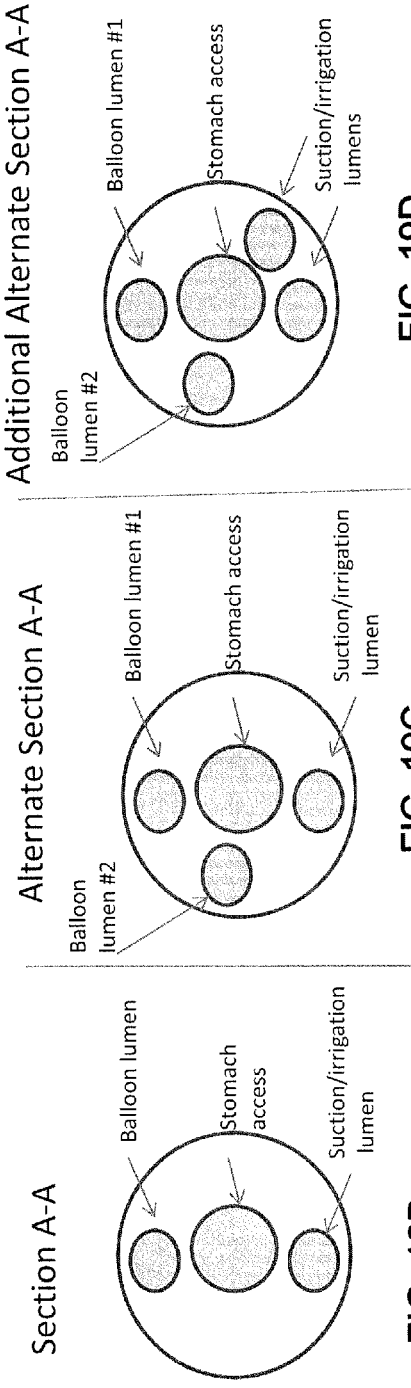
FIG. 19A
FIG. 19B
FIG. 19C
FIG. 19D

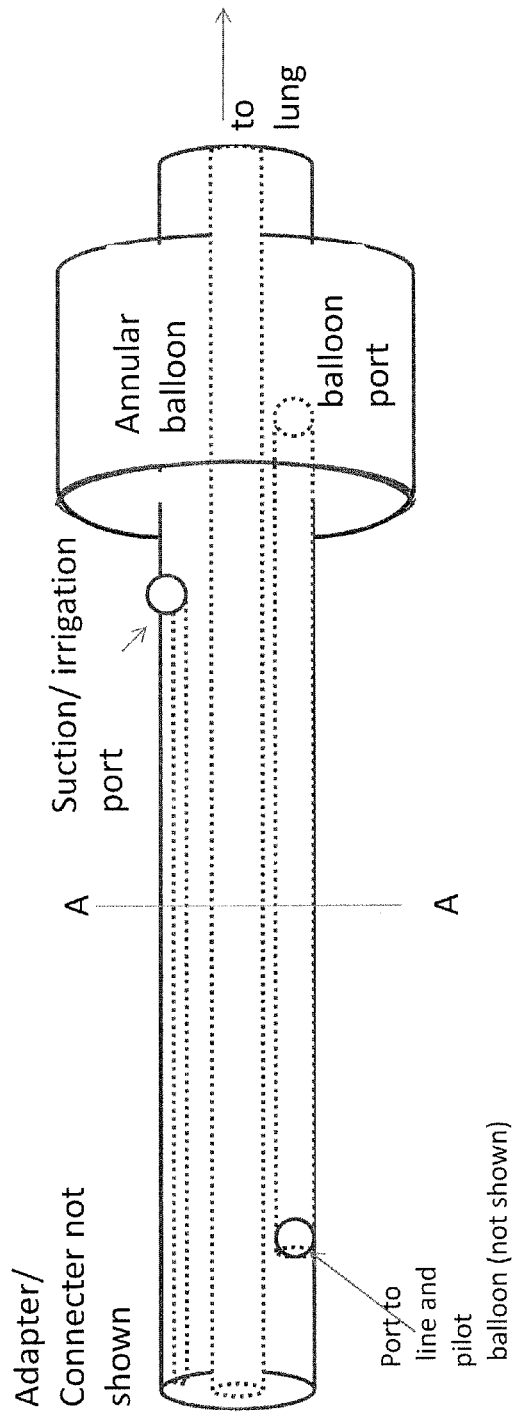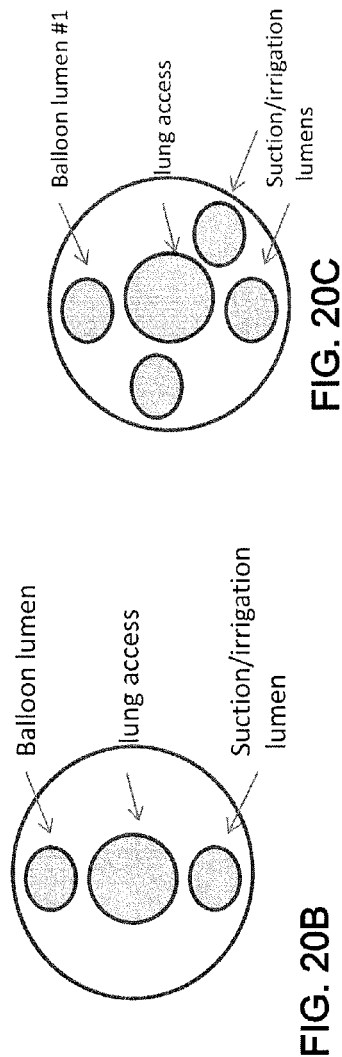
FIG. 20A
FIG. 20B
FIG. 20C

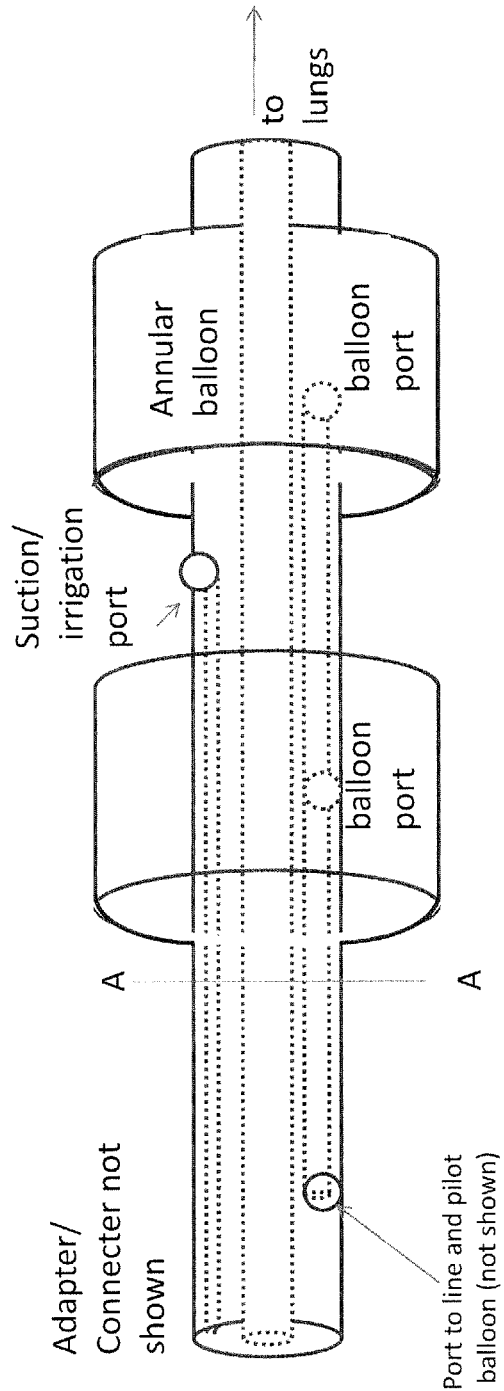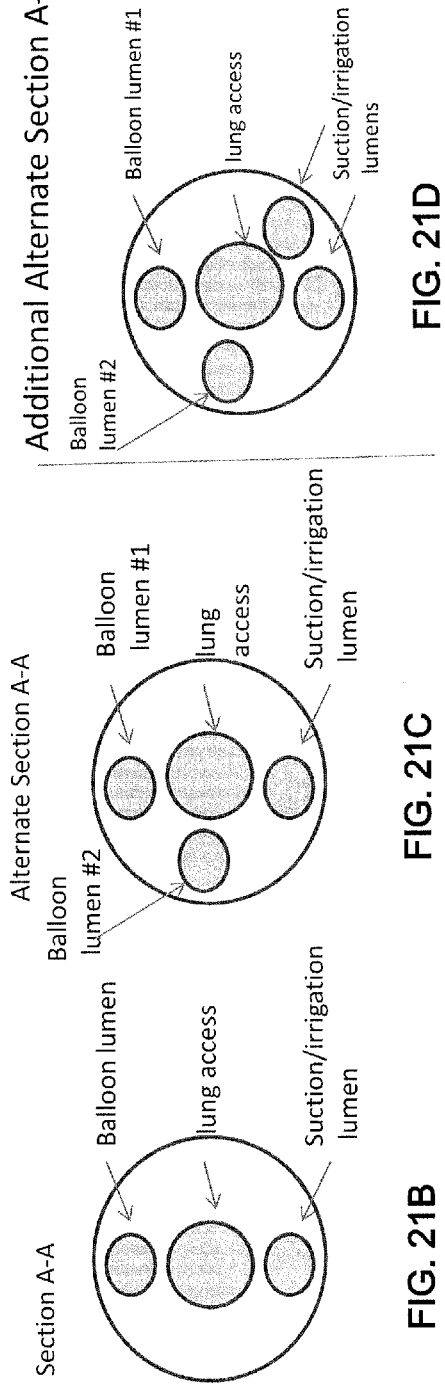
FIG. 21A
FIG. 21B
FIG. 21C
FIG. 21D

Example 1; X Axis: Minutes; Y Axis: Temperature in Celsius

Example 1; X Axis: Minutes; Y Axis: Temperature in Celsius

Example 2; X Axis: Minutes; Y Axis: Temperature in Celsius

NON-INVASIVE SYSTEMS, DEVICES, AND METHODS FOR SELECTIVE BRAIN COOLING

This application claims priority to U.S. Provisional Patent Application No. 61/511,409 filed Jul. 25, 2011, which is incorporated herein by reference in its entirety.

BACKGROUND

1. Field of the Invention

A device, system, and method are disclosed for controlling and/or regulating temperatures of the brain and/or body in a subject.

2. Description of Related Art

Brain injury is common, devastating, and often very expensive to treat. Management of patient temperature by either induction of hypothermia or aggressive treatment of fever has been recommended by the American Heart Association (AHA) as the standard of care for cardiac arrest. Brain temperature management has also been used to treat birth-related cerebral damage and has been FDA approved therapy during cardiac and neurosurgery. Temperature management has been investigated for a variety of central nervous system conditions, including stroke, mechanical brain trauma, and spinal cord injury. A variety of devices have been proposed for therapeutic organ cooling and in particular therapeutic cooling of the brain. Such devices generally fall into one of two broad categories: systemic devices and selective devices.

Systemic devices are widely used today, but selective devices offer compelling advantages. Selective cooling enables the creation of a temperature gradient between the brain and the body core, which can reduce complications associated with body core cooling, resulting in improved patient safety and enabling deep cooling of the brain tissue to achieve neuro-protection.

In general, a high degree of selectivity in temperature management has required a high, and generally undesirable, degree of invasiveness. Surgically invasive devices, such as intravascular devices, often focus on cooling the blood supply to a target area and warming the returning blood supply to prevent cooling of the body core. Intravascular systems and other similarly invasive devices, however, may not be suitable for rapid deployment because they require intervention by a surgeon. A further limitation of catheter-based devices is that they require surgical invasion of a major blood vessel, introducing risk of infection, bleeding, thrombosis, rupture of the blood vessel, dissection of the blood vessel wall and introduction or dislodging debris in the vasculature. These risks are doubled when an intravascular warming catheter is introduced to re-warm blood flow returning from the cooled organ(s).

Other selective, brain focused, non-invasive cooling devices require nebulized fluids that undergo a phase change (evaporation) to maximize a rate of heat transfer from the body. An example of this method is described for example, in U.S. Pat. No. 7,837,722 to Barbut et al. Drawbacks of this approach include exposure of the patient to fluorocarbon coolant (if used as a free flowing liquid), exposure of bystanders to fluorocarbon coolant, and the formation of entrained debris that is difficult to recapture as the coolant leaves the patient. Also, this approach appears to yield a relatively slow cooling rate in human trials, about 2° C. per hour and to our knowledge, a shallow average depth of cooling of <4° C. steady state reduction in brain temperature.

Another selective device is described in U.S. Pat. No. 7,189,253 to Lunderqvist et al. The Lunderqvist devices introduce fluid filled balloons into the nasal cavity and cool the cavity by recirculating cold fluid. These devices control brain temperature by adjusting the temperature of the cooling fluid based on measurement of tympanic membrane temperature. Drawbacks of this approach include a reduction in heat transfer rate due to a reduction in surface area exploited (e.g., the surface area of the sinuses is excluded and the air in the sinuses acts as a barrier to heat transfer) and the heat transfer resistance of the balloon itself. In addition, trauma to the nasal cavity is possible during balloon expansion in the nasal cavity, which is accomplished by restricting fluid flow from the balloon to increase a fluid pressure within the balloon.

These approaches are limited in that they exploit the nasal cavity only, resulting in in a lower heat transfer rate than one which includes, for example, the remainder of the pharynx and the esophagus. For example, the surface area used for heat transfer is greater when the pharynx and esophagus are included. As another example, the heat transfer rate through the perivascular tissue is slow relative to the flow rate of blood rising in the carotid and vertebral arteries. That is to say, the blood flowing in the large arteries of the chest, neck, and head will not thermally equilibrate with the tissue surrounding the arteries during active temperature manipulation, except in circumstances of severely reduced blood flow. The long cold zone of a combined esophageal, pharyngeal, and nasal approach means an enhanced residence time in the cold zone for the blood and thus a greater degree of equilibration and cooling.

Other conventional approaches utilize balloon-based devices, such as those disclosed by Takeda in U.S. Patent Publication Nos. 2008/0086186 and 2009/0177258. Such contained use of fluids generally does not, for example, provide good surface contact with the tissues of the airway or stomach, reducing heat transfer. In addition, such methods can make it difficult to provide access to adjacent areas of the body to promote respiration and/or allow the passage of liquids or gases.

If warming and cooling are used together to create a brain-body temperature gradient, it can be beneficial to use some type of control system to coordinate the warming and cooling activities. Conventional systems for providing temperature controls to separately cool and warm portions of a patient, like that disclosed by Lennox in U.S. Patent Publication No. 2003/0130651, do not have integrated control systems and, as a result, neither temperature control is aware of the action of the other except via measurements of patient temperature. Accordingly, such systems, with their non-integrated controls and reliance on single point measurements of brain and body temperature, respectively, cannot optimally account for time lags between actions in the brain cooling system and responses in body temperature, among other things.

SUMMARY

The slow rate of cooling and/or delays in initial treatment, for example, in conventional therapeutic hypothermia devices and methods can limit the effectiveness of those systems in preserving tissue function (e.g., such as neurological function) following hypoxia, myocardial function following myocardial infarction, stroke, and/or other types of function following inflammation or injury. Conventional systems also have suffered from difficulties in focusing cooling on the desired target organs without incurring cooling-related complications in the rest of the body. At least some of these disadvantages are addressed by the systems and method disclosed herein, resulting in systems and methods that permit more rapid and/or deeper selective therapeutic hypothermia, among other things.

In one embodiment, a method for selectively and non-invasively cooling the brain includes introducing an irrigating fluid into a patient's aerodigestive tract, monitoring a first temperature of the patient's body, setting a target temperature that is different from the first temperature, and changing the rate of flow of the irrigating fluid to bring the first temperature closer to the target temperature. The method can include changing the rate of flow (e.g., intermittently starting and stopping the flow) of irrigating fluid to the patient's aerodigestive tract, as needed, in response to a difference between the first temperature and the target temperature.

In some disclosed embodiments, the cooling can be targeted to the brain (for example, to preserve neurological function following a stroke, brain injury, myocardial infarction, or episode of cardiac arrest) or more generally to the entire body (for example, to control generalized inflammation or injury to non-brain structures, such as the spinal cord and/or myocardium).

In other disclosed embodiments, the improved systems for inducing rapid hypothermia include cooling a region of the aerodigestive tract for rapid selective brain cooling. This rapid cooling can permit the method to be used more effectively in urgent situations so that effective cooling can be induced prior to completion of irreversible tissue damage. Following induction, the method is also capable of effectively maintaining cooling for sustained periods of time to provide maximal therapeutic benefit. Variations of the method can achieve targeted or selective cooling of the brain, or less selective cooling of both the brain and the body, as required by clinical conditions.

In other embodiments, an apparatus for selective and non-invasive cooling of the brain is provided. The apparatus can include at least one nasal catheters (e.g., sized to be introduced through the nostrils of a patient), at least one esophageal catheters (e.g., multi-lumen esophageal catheters sized to be inserted into the esophagus of the patient), and at least one tracheal catheter (e.g., at least one multi-lumen tracheal catheter sized to be inserted into the trachea of the patient). The esophageal catheter can have a distal end and a proximal end, with the distal end configured to extend past the aortic arch of the patient when the esophageal catheter is disposed in the esophagus of a patient. The esophageal catheter can include a first lumen, a second lumen, and/or a third lumen (and in some embodiments, as discussed below, a fourth lumen), with the first lumen of the esophageal catheter extending, for example, from the proximal end to the distal end to provide access to the stomach when the esophageal catheter is disposed in the esophagus of a patient, the second lumen of the esophageal catheter extending, for example, from the proximal end and terminating inside a first esophageal inflatable member near the distal end of the esophageal catheter, and the third lumen of the esophageal catheter extending, for example, from the proximal end to at least one port (e.g., one or more ports) located proximal to the first esophageal inflatable member. The tracheal catheter can include a first lumen, a second lumen, and/or a third lumen (and in some embodiments, as discussed below, a fourth lumen), with the first lumen of the tracheal catheter extending, for example, from the proximal end to the distal end to provide access to the lungs to allow the passage of air into and out of the lungs when the tracheal catheter is disposed in the trachea of a patient, the second lumen of the tracheal catheter extending, for example, from the proximal end and terminating inside a first tracheal inflatable member near the distal end of the tracheal catheter, and the third lumen of the tracheal catheter extending, for example, from the proximal end to at least one port (e.g., one or more ports) located proximal to the first tracheal inflatable member. In some embodiments, as discussed below, tracheal and/or esophageal inflatable members can be inflated with fluid and/or gases. In some embodiments, tracheal and/or esophageal inflatable members can comprise at least one pressure sensor configured to detect at least one of a pressure within the inflatable member and a pressure exerted by the inflatable member on tissue. In some embodiments, the apparatus further comprises a base unit coupled to at least one of the tracheal and the esophageal catheter and configured to regulate pressure in the inflatable members. In some embodiments, the base unit can be configured to alert a user when a threshold pressure is met or exceeded (e.g., within the inflatable member and/or due to surrounding tissue). Catheters in the present invention can comprise a circular or a non-circular cross-section.

In other embodiments, the present apparatuses comprise an apparatus for cooling at least one of the brain and the spinal column, where the apparatus is configured to direct free flowing fluid (e.g., non-nebulized) into an aerodigestive tract of a patient, remove the fluid from the aerodigestive tract of the patient, and recirculate the fluid into the aerodigestive tract until reaching at least one of a target brain to body core temperature gradient (e.g., at least 3° C., 4° C., 5° C., 6° C., 7° C., 8° C., 9° C., 10° C., 11° C., 12° C., 13° C., or, for example, from 3° C. to 25° C., 4° C. to 12° C., 10 to 12° C., etc.) and a target spinal column to body core temperature gradient (e.g., at least 3° C., 4° C., 5° C., 6° C., 7° C., 8° C., 9° C., 10° C., 11° C., 12° C., 13° C., or, for example, from 3° C. to 25° C., 4° C. to 12° C., 10 to 12° C., etc.).

In another embodiment, a method for selective and non-invasively cooling the brain is provided. The method can include directing a free flowing fluid (e.g., non-nebulized) into a nasopharynx, oropharynx, hypopharanx, and/or esophagus of a patient, with the fluid being introduced into the nose, mouth, and/or esophagus of the patient through a plurality of catheters. The fluid can be directed out of the nasopharynx, oropharynx, hypopharanx, and esophagus of the patient through one or more of the plurality of catheters. The fluid can be recirculated and redirected back into the nasopharynx, oropharynx, hypopharanx, and esophagus of the patient. One or more of the cooling depth, duration, power, and/or incoming fluid temperature can be controlled based on measurements obtained from temperature inputs from the body of the patient outside of the patient's brain.

In another embodiment, a method for preventing ventilator associated pneumonia is provided. The method can include (a) placing a tracheal catheter with a tracheal inflatable cuff at a distal end of the tracheal catheter into the patient, (b) placing an esophageal catheter with an esophageal inflatable cuff at a distal end of the esophageal catheter into the patient, (c) introducing a free flowing non-nebulized cold non-toxic irrigation liquid into the aerodigestive tract with the cold irrigation liquid substantially filling and directly contacting the walls of the aerodigestive tract, and (d) inflating the tracheal inflatable cuff and the esophageal inflatable cuff (e.g., with gas or liquid) to restrict the flow of liquid in the patient to above a level of the trachea and the stomach to achieve selective targeted cooling of the brain.

In some disclosed embodiments, organ hypothermia is induced by introducing a flow of non-nebulized cold, biologically compatible irrigation liquid into the aerodigestive tract—but not the lungs—of the subject so that the cold irrigation liquid substantially fills and directly contacts the walls of the aerodigestive tract to achieve rapid and effective heat exchange over the large and irregular surface of the tract that the liquid contacts. The cold irrigation liquid can be maintained at a temperature of, for example, −30° C. to 20° C. The liquid is allowed to flow in a coherent large volume mass through the aerodigestive tract and along the exposed irregular surface of the aerodigestive tract. In some embodiments, a flow of liquid is also directed externally against the head of the subject (such as the face and/or scalp) to further accelerate cooling. The head of the subject may be at least partially immersed in cold liquid that is agitated to apply flow for convective heat transfer. As another example, a flow of a cold liquid can be directed toward the head of the subject from a liquid flow tube even when the head is not immersed in the cool liquid.

In one embodiment of the present methods, the irrigation liquid is introduced into the aerodigestive tract by placing multi-lumen catheters in the aerodigestive tract and flowing liquid through the catheters into the aerodigestive tract. The catheters in some examples are placed in the aerodigestive tract to introduce the liquid only above the level of the trachea and esophagus to achieve selective targeted cooling of the brain by primarily cooling the structures near the brain and in contact with blood vessels that supply blood to the brain.

In other examples, the catheters are placed to introduce the liquid into the esophagus and/or stomach to achieve non-selective organ cooling by bringing the liquid into contact with the insulated structures of the mediastinum through which venous blood returns to the heart. The insulated anatomic chamber provided by the mediastinum, in combination with the high flow of cooling liquid, permits excellent heat exchange with the circulating blood to achieve the desired rapid cooling effect in a manner that is less brain specific. In addition to the placement of catheters in the esophagus and stomach, one or more catheters can also be placed to introduce the flow of liquid into the upper aerodigestive tract structures above the level of the esophagus to provide additional or maximal cooling. For example, the catheters are placed with their introduction ports or tips in the nasal cavity, oral cavity, and/or hypopharynx (and preferably all three). In other embodiments, the catheters have multiple lumens and/or multiple ports to introduce the cooling liquid at multiple points along the length of the catheters to increase the fluid flows outside of the catheter that have been found to be effective in the rapid protective induction of therapeutic hypothermia.

A subject can also be intubated with an endotracheal tube having a cuff on the tube so that the cuff can be inflated (e.g., with gas, liquid, etc.) to inhibit entry of the irrigation liquid into the lungs. In addition, a tube with an inflatable balloon can be placed in the esophagus, and the balloon can be inflated (e.g., with gas, liquid, etc.) to substantially inhibit flow of liquid out of the upper airway into the lower esophagus and stomach. Isolating the gastrointestinal tract (including the lower esophagus (e.g., substantially below the aortic arch)) from the flow of cold liquid in the upper airway helps direct the cooling effect to the upper airway and the structures (including blood vessels) that are in heat transferring proximity with the cold liquid.

To help achieve and maintain rapid and effective cooling of the desired anatomic structures, it can be useful to provide a sufficient reservoir of pre-cooled liquid for introduction internally into the aerodigestive tract and/or externally against the head. An external reservoir of irrigation liquid is provided that supplies a sufficient volume of cool liquid at the selected flow rate. In some embodiments, the reservoir is also a container in which the head is completely or partially immersed. Alternatively, the reservoir partially or completely surrounds a receptacle in which the head is placed, and the receptacle collects cooling liquid that flows out of the mouth and/or nose after it has circulated within the aerodigestive tract outside of the irrigation catheters. In other embodiments, the reservoir is placed in a back support that also contacts the back and optionally cools the body and structures of the back, such as the spinal cord. These and other embodiments can be incorporated into devices that are or can be attached to (or roll in tandem with) a stretcher so that the hypothermia therapy can be administered to a patient in transit.

The liquid that is introduced into the aerodigestive tract can leave the aerodigestive tract by flowing out of the mouth and/or nose of the subject to return to the external reservoir. The return of the liquid can be passive, and not contained in a suction tube, so that the cool return liquid flows along the length of at least the upper airway or along the entire aerodigestive tract to intimately contact the entire irregular surface of that tract. In some embodiments, the aerodigestive tract—other than the lungs—is substantially filled with the cooling liquid. Passive return of the liquid can help avoid traumatic damage to the aerodigestive tract that could occur if a return lumen is occluded in a system that requires flow through such a circuit for removal. Liquid that flows out of the mouth and nose of the subject can return passively to the reservoir to be cooled, or circulated externally of the reservoir for cooling. In other embodiments, the external reservoir is a container in which at least part of the head is contained, or over which the head is positioned, to collect the liquid that flows out of the mouth and/or nose of the subject by gravity-assisted flow of the liquid. However, in other embodiments, as described in detail throughout this application, fluid can be actively removed from the aerodigestive tract (e.g., by a suction device through at least one of a plurality of catheters).

In some embodiments of the present methods, the liquid reservoir is a neck support on which the neck of the subject is positioned with the neck tilted backwards (extended) to help protect the airway of the subject and promote the flow of liquids through the aerodigestive tract (and not the lungs). In embodiments in which the neck is extended, the head may be tilted back into a container of cool liquid to partially, substantially, or completely immerse the head in the cold liquid. Alternatively, the liquid reservoir is a back and neck support that helps stabilize the spine (for example, in cases of possible spinal injury). The support itself may be hollow and contain the reservoir of cold liquid, or the support may be a body supporting platform suspended over a tub of cold water. For example, a tub can be large enough to receive a body that is suspended above it, and in which ice or other cold items can be placed along with the supply of cooling liquid. In other examples, the reservoir has 1-50 liters of cool liquid in it, or liquid to be cooled. The volume of cool liquid in the reservoir can vary depending on the clinical circumstances. For example, smaller volumes (1-20 L) may be preferred outside of an inpatient setting (for example, in an ambulance), but larger volumes (e.g., greater than 20, 30, or 40 L) can be used for inpatient settings.

In some embodiments, a method can comprise directing a free flowing fluid (e.g., non-nebulized) into the aerodigestive tract of a patient (e.g., through a plurality of catheters), removing the fluid from the aerodigestive tract of the patient (e.g., through at least one of the plurality of catheters), and recirculating the fluid into the aerodigestive tract (e.g., through a plurality of catheters) until reaching a target brain to body core temperature gradient (e.g., at least 3° C., 4° C., 5° C., 6° C., 7° C., 8° C., 9° C., 10° C., 11° C., 12° C., 13° C., or, for example, from 3° C. to 25° C., 4° C. to 12° C., 10 to 12° C., etc.) and/or a target spinal column to body core temperature gradient (e.g., at least 3° C., 4° C., 5° C., 6° C., 7° C., 8° C., 9° C., 10° C., 11° C., 12° C., 13° C., or, for example, from 3° C. to 25° C., 4° C. to 12° C., 10 to 12° C., etc.). In some embodiments, the methods are configured to maintain a target brain to body core temperature gradient and/or a target spinal column to body core temperature gradient at a substantially constant gradient for at least 1 hour, at least 4 hours, at least 12 hours, at least 24 hours, and/or from 1 to 12 hours. In other embodiments, the fluid can comprise various additives, such as, for example, electrolytes, antibacterial agents, propylene glycol, mucosal protectants, and/or additives to make the fluid hypertonic. In some embodiments, no cooling procedures are directed to the exterior of the patient's head.

In some embodiments, a method can further comprise activating a warming device to warm at least a portion of a patient, directing a free flowing fluid (e.g., non-nebulized) into the aerodigestive tract of the patient (e.g., through a plurality of catheters), removing the fluid from the aerodigestive tract of the patient (e.g., through at least one of the plurality of catheters), and recirculating the fluid into the aerodigestive tract of the patient (e.g., through the plurality of catheters). In such embodiments, the warming device can comprise, for example, warming blankets, hot air blankets, water blankets, and/or warming bulbs. In some embodiments, the warming device can be disposed in contact with a patient's head, in contact with the palms of a patient's hands, in contact with the soles of a patient's feet, in proximity to at least one of a patient's veins, and/or the like. Further, warmed air can be passed into a patient's lung (e.g., through at least one of the plurality of catheters).

In other embodiments, the present methods can comprise reducing blood flow to a patient's brain, directing a free flowing fluid (e.g., non-nebulized) into the aerodigestive tract of the patient (e.g., through a plurality of catheters), removing the fluid from the aerodigestive tract of the patient (e.g., through at least one of the plurality of catheters), and recirculating the fluid into the aerodigestive tract of the patient (e.g., through the plurality of catheters). Reducing blood flow to a patient's brain can comprise, for example, sedating the patient, decreasing the patient's blood pressure, administering barbiturates to the patient (e.g., thiopental, phenobarbital, pentobarbital, methohexital, etc.), administering propofol to the patient, administering benzodiazepines to the patient, administering lidocaine to the patient, administering etomidate to the patient, administering caffeine to the patient, administering alcohol to the patient, administering narcotics to the patient, administering cocaine to the patient, administering beta-blockers to the patient (e.g., labetalol), administering anti-migraine medications to the patient (e.g., triptans, ergotamines, etc.), administering clonidine to the patient, and/or administering vasoconstrictors to the patient (e.g., phenylephrine). In other embodiments, reducing blood flow to a patient's brain can comprise warming the exterior of the patient's head, warming the patient's skin, reducing the brain's metabolism, shunting blood to the body core away from the brain, increasing jugular vein pressure, and/or inducing temporary hyperventilation.

In some embodiments, the present methods comprise directing a free flowing fluid (e.g., non-nebulized) into the aerodigestive tract of the patient (e.g., a plurality of catheters), removing the fluid from the aerodigestive tract of the patient (e.g., through at least one of the plurality of catheters), monitoring a temperature of at least one of patient's brain and the patient's body core, and recirculating the fluid into the aerodigestive tract (e.g., through the plurality of catheters) until a target temperature is reached. In some embodiments, monitoring a temperature of a patient's brain can comprise disposing a bolt comprising a temperature sensor in the patient's brain, administering a magnetic resonance imaging procedure to the patient, and/or inserting a temperature sensor intravenously in the jugular and positioning the temperature sensor near the brain.

This specification also discloses multiple devices for carrying out the methods of inducing organ cooling in a subject. In one example, a head receptacle is adapted for receiving and maintaining a head of the subject at least partially immersed in cool liquid, and a neck support for supporting the neck of the subject with the head of the subject tilted backwards into the liquid container. The container can include a liquid reservoir of cold cooling liquid outside of the receptacle, or the receptacle itself can serve as the reservoir. The device further includes an outflow port for delivering cold liquid from the reservoir with one or more outflow lines (such as catheters) connected to the outflow port for placement in the aerodigestive tract of the subject. One or more pumps can withdraw liquid from the reservoir to move it through the catheter(s) and into the aerodigestive tract. In some examples, the one or more pumps are capable of delivering 0.1 to 10 L/min of cooling liquid to the aerodigestive tract of the subject.

In one embodiment of the device, the liquid reservoir is a compartment that at least partially abuts the head receptacle, and a drain communicates between the head receptacle and the liquid reservoir to return liquid from the head receptacle to the liquid reservoir. The liquid reservoir may be an at least partially hollow backboard for supporting a back of a subject, and the backboard that contains the cooling liquid can be thermally conductive so that cool liquid within the backboard cools the back of a subject placed on the board. The backboard may include a top, body-supporting surface and an inclined neck tilt inducing surface that inclines into the head receptacle to support the body above the head receptacle. The top surface of the backboard may incline upwardly to elevate the thorax relative to the feet, and also downwardly to provide a downwardly sloping surface on which the head rests with the neck extended. The top surface of the backboard may further include a neck support that is placed at the level of the cervical spine of the subject. The neck support may be adjustable in height and/or padded.

One advantage of the disclosed method and device is that it is suitable for use outside of or in transit to the hospital, for example in an ambulance or on a stretcher that is being moved. For example, a wheeled stretcher has a body support surface on which a back board is placed, a neck support board that inclines from the back support board into a reservoir for liquid, and a head support member carried by the neck support board. The position of the head support member is adjustable along the neck support member to adjust the head at a desired height (or depth) in the reservoir. In some embodiments, a wheeled support is provided beneath the reservoir so that the reservoir can be wheeled in tandem with the stretcher.

In some embodiments of the device, the head receptacle comprises a bottom support surface, a back wall, side walls, and a front wall, wherein the front wall is shorter than the back and side walls to support the neck of the subject. The front wall is adjustable in height to support the neck of the subject at different heights and may be padded for the protection of the patient. The head receptacle is surrounded by a container that serves as the reservoir.

The system further includes catheters for placement in the aerodigestive tract of the subject, and a pump for circulating liquid from the receptacle into the aerodigestive tract.

In other disclosed embodiments, the brain is cooled by direct external cooling of the head and cooling of blood that is delivered to the brain. The head can be placed in a container that holds a reservoir of circulating cold liquid that externally cools the brain. Cold liquid can be infused into the upper airway through catheters placed in the nasal cavity, oral cavity, and/or upper chest to directly cool the inferior surface of the brain and the brainstem, and indirectly cool other areas of the brain by cooling blood that passes through the carotid and vertebral arteries. Sufficient volumes of cool liquid can be delivered to the upper airway such that fluid substantially fills the upper airway with the cool liquid which then flows out of the nose and mouth and into the reservoir of cool liquid that is circulating around the head in the container.

In some disclosed embodiments, the head in the container is completely submerged in the cool liquid, with the liquid covering the nose and mouth to help completely fill the upper airway with the liquid.

Some devices or systems for carrying out the methods of cooling the brain include a liquid container for receiving and maintaining the head of the subject at least partially immersed in cool liquid, and a source of cool liquid for absorbing heat to induce brain hypothermia. A plurality of liquid delivery catheters are connected to the source of cool liquid for insertion into the aerodigestive tract of the subject for direct delivery of cool liquid to those sites. A liquid circulation tube is also connected to the source of cool liquid and is placed in the container to circulate cooled liquid around the head of the subject in the container. Pumps are operatively associated with the device to move liquid from the container through the liquid delivery catheters and into the patient. The system, for example, cools the outer surface of the brain through the cranium, cools the inferior surface of the brain and brainstem through cool liquid delivered into the nasopharynx, and cools the blood perfusing the brain from the arteries of the mediastinum and neck (such as the internal carotid, vertebral arteries, proximal-inferior portions of the cerebral arteries, proximal portions of the penetrating arteries of the inferior surface of the brain, etc.) through liquid delivered into the pharynx and/or esophagus.

The cool liquid can be maintained, for example, at a temperature of −30° C. to 20° C. to transfer heat from the brain at a sufficient quantity and at a sufficient rate to quickly induce hypothermia. Suitable liquids for this purpose include, for example, perfluorocarbons, oils, and/or water mixtures containing salts, simple sugars, organic compounds (such as propylene glycol), antibacterial agents, mucosal protectants (e.g., antioxidants, free-radical scavengers, etc.), and/or electrolyte additives (e.g., to prevent loss of potassium, calcium, etc., into the fluid bath, especially when fluid is not recycled to a subject again).

The source of cool liquid preferably provides sufficient liquid to substantially fill the upper airway (including the nasopharynx, oropharynx, hypopharynx, and proximal trachea) with the cool liquid. In other embodiments, the source of liquid is also sufficient to substantially fill the upper esophagus, entire esophagus, and/or stomach.

The foregoing and other objects, features, and advantages of the invention will become more apparent from the following detailed description, which proceeds with reference to the accompanying figures.

Any embodiment of any of the present devices, systems, and methods can consist of or consist essentially of—rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures illustrate the described elements using graphical symbols that will be understood by those of ordinary skill in the art. The embodiments of the present devices (and their components), systems, and methods shown in the figures are drawn to scale for at least the embodiments shown.

FIG. 5D shows an alternative version of the device with a front wall having an adjustable height for supporting the neck of a subject in different degrees of neck extension. FIG. 5E shows the device of FIG. 5D with the head receptacle at least partially filled with cooling liquid.

FIG. 6B is a view similar to FIG. 6A, but showing a back support that has an upwardly included surface to elevate the upper thorax above the waist.

FIG. 7 is a view of another embodiment of the device in which a flat body support platform is fixed in, on, or slightly above a large tub of cooling water with ice floating in it to cool the water in the tub.

FIGS. 18A-C are representative sketches of one embodiment of a multi-function esophageal catheter for use with the described cooling and temperature management system and exemplary section views taken along line A-A in FIG. 18A.

FIGS. 19A-D are representative sketches of one embodiment of a "double section" balloon esophageal catheter used in certain embodiments of the described cooling and temperature management system and exemplary section views taken along line A-A in FIG. 19A.

FIGS. 20A-C are representative sketches of one embodiment of a multi-lumen tracheal catheter for use with the described cooling and temperature management system and exemplary section views taken along line A-A in FIG. 20A.

FIGS. 21A-D are representative sketches of one embodiment of a "double section" balloon tracheal catheter used in certain embodiments of the described cooling and temperature management system and exemplary section views taken along line A-A in FIG. 21A.

DESCRIPTION OF ILLUSTRATIVE EMBODIMENTS

Figure 1A:
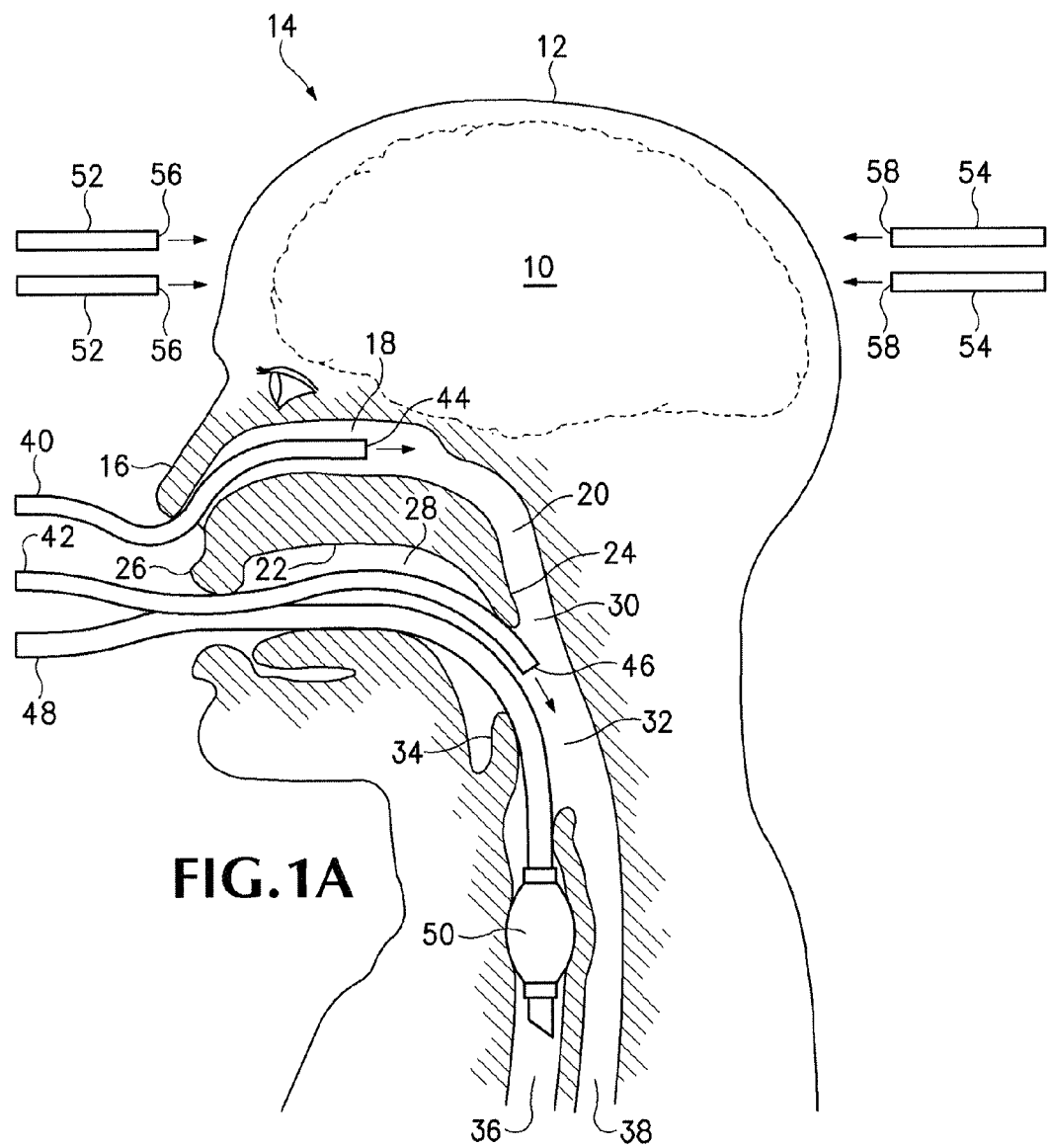
FIG. 1A is a schematic sectional side view of a human head and upper thorax depicting one configuration of nasal and oral catheters inserted to flow cooling liquid through the upper aerodigestive tract. An embodiment of an endotracheal tube with an inflated cuff is shown inserted into the proximal trachea. Also depicted are optional external catheters configured to apply liquid flow externally against the head.

The following description is exemplary in nature and is not intended to limit the scope, applicability, or configuration of the invention in any way. Various changes to the described embodiments may be made in the function and arrangement of the elements described herein without departing from the scope of the invention.

Although the operations of exemplary embodiments of the disclosed methods may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment or example are not limited to that embodiment or example, and can be applied, in whole or in part, to any embodiment or example disclosed herein.

As used in this application and in the claims, the terms "a," "an," and "the" include both the singular and plural forms of the element(s) they refer to unless the context clearly dictates otherwise.

The term "aerodigestive tract" refers to a complex of organs that, in total, make up the tissues and organs of the upper respiratory tract and the upper part of the digestive tract. The aerodigestive tract, as used herein, can include the lips and mouth, tongue, nose, throat, vocal cords, esophagus, stomach and/or trachea. The aerodigestive tract does not include the lungs. The phrase "introducing liquid into the aerodigestive tract" includes introducing liquids into any part of the aerodigestive tract, such as the nasal cavity, upper airway (nasal and oral cavity and pharynx), the nasal cavity and upper airway and esophagus, or the nasal cavity and upper airway and esophagus and stomach, or any combination or sub-combination thereof.

The term "coupled" is defined as connected, although not necessarily directly, and not necessarily mechanically (e.g., electrically, electromagnetically, physically, chemically, etc.). Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled to the second structure.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device or system that "comprises," "has," "includes," or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps.

Terms such as "first" and "second" are used only to differentiate structures or features, and not to limit the different structures or features to a particular order or quantity.

"Extension" of the neck refers to bending the neck to move the head posteriorly.

"Pharynx" refers to the part of the neck and throat situated immediately posterior to the mouth and nasal cavity, but superior to the esophagus, larynx, and trachea. It is anatomically divided into the nasopharynx (posterior to the nasal cavity), oropharynx (posterior to the oral cavity), and hypopharynx or layngopharynx (between the oropharynx and the esophagus).

"Hypothermia" refers to a condition in which body or organ temperature is below normal physiological temperatures. "Therapeutic hypothermia" refers to hypothermia induced to attempt medical benefit in a subject. Inducing "selective hypothermia" does not require absolute selectivity; relative selectivity of cooling a target organ or area can occur. Hence inducing "selective hypothermia" refers to inducing hypothermia in a target organ or organs to a greater extent or substantially greater extent than in non-target organs. For example, selective hypothermia may be induced in the brain or head of a subject by selectively cooling blood vessels that perfuse that organ as well as selectively cooling anatomic structures that are contiguous with that organ. Selective hypothermia need not be absolutely selective, and some cooling of other organs (or the entire body) can occur. In particular examples, selective hypothermia can reduce the temperature of the target organ (such as the brain) by at least 10%, 25%, 50%, or 75% more than the reduction of overall core body temperature. Inducing "non-selective hypothermia" refers to a generalized cooling of the body that is not specifically targeted to any particular organ (such as the brain). However, even with "non-selective" cooling some preferential cooling of a particular organ can occur.

A "non-nebulized" liquid is one that is not turned into a fine spray or atomized. The non-nebulized liquid therefore emerges in a continuous liquid stream instead of discontinuous droplets. The continuous or coherent liquid flow provides greater flow rates (with consequently greater cooling rates) and can be achieved by using non-nebulized, but perhaps intermittent introduction of cooling liquid into the aerodigestive tract.

"Turbulent flow" of liquid is agitated flow that is not strictly laminar. Turbulent flow helps disrupt liquid barriers and increases heat transfer as compared to laminar flow.

"Forced flow" describes any non-stagnant flow—e.g., moving liquid driven by a pressure head, pump, or residual kinetic energy. The flow can be either laminar or turbulent.

"Upper aerodigestive tract" refers to the portion of the aerodigestive tract above the esophagus. The "upper airway" refers to the air passageways above the trachea, which includes the nasal and oral cavities, as well as the pharynx.

References to "introducing a catheter" are understood to refer to introducing one or more catheters. For example, introducing a catheter into the nasal cavity can refer to introducing a catheter into each nostril so that there are two catheters in the nasal cavities. As another example, introducing a catheter into the nasal cavity can refer to introducing a catheter into one of the two nostrils so that there is one catheter in the nasal cavity. Catheters may have multiple lumens to allow passage of instruments, measuring devices, liquid flows, and/or gas flows "Catheter" refers to a hollow tube configured to be inserted into a body cavity, duct, or vessel to allow passage of fluid and/or gases. Catheters may have—but are not required to have—multiple lumens to allow passage of instruments, measuring devices, liquid flows and or gas flows. Any use of the term catheter throughout the application should be interpreted to be broad enough to include both single- and multi-lumen catheters.

"Tube" refers to a generally hollow cylinder, especially one that conveys fluids as a passage. A tube can have—but is not required to have—multiple lumens, similarly to catheters. A "line" is a "tube" that can be, but is not necessarily, generally cylindrical like a "tube."

"Lumen" refers to an inner open space of a catheter, tube, or other such member.

As used herein, a "temperature management kit" refers to a system that includes a base unit, an interface kit, and any associated software that can function to control the temperature of the patient in the manner described herein.

"User" or "care provider" refers to those taking care of the patient or those setting up, operating, or otherwise using the devices, systems, and/or methods disclosed herein.

A "reusable base unit" refers to a part of a system that is intended to be used with more than one patient.

An "interface kit" refers to a part of a system that is intended to be used only once (e.g., because it comes in contact with the patient's body or bodily fluids).

A "control unit" or "control system" refers to a mechanical, optical, or electronic system used to, for example, maintain a desired output, receiving and processing measured data from the patient, comparing it to the user's commands, and adjusting power and/or flow rates as needed to reach and maintain goal temperature(s) and/or pressure(s). As an example, a control unit or control system can be part of a base unit and can include software responsible for carrying out some or all of the described procedures.

The term "reusable cooling system" refers to a component (e.g., part of the base unit) that causes energy to move to and from a single use heat exchanger. A reusable cooling system can include, for example, thermoelectric devices and associated electronics refrigeration system, and/or other heat pumps or other means (such as endothermic chemical reaction) for creating a cold cooling surface.

A "cooling surface" refers to a part of the cooling system that is in thermal contact with a single use heat exchanger.

A liquid flow described as "continuous" or "coherent" is distinguished from a nebulized flow by having a density of 90% or more of that typical of the bulk liquid. However, the flow may be intermittent on timescales greater than about 10 seconds.

In general, it is believed that the neuroprotective benefits of temperature management arise from cooling the brain, in particular, while the observed complications arise from cooling the body core. Therefore, brain selective devices are in general preferred over systemic ones. Systemic, non-invasive devices are sometimes used to cool the entire patient, which eventually leads to cooling of the brain. However, it is generally recognized that cooling the body can create complications such as pneumonia, shivering, low cardiac output, and cardiac arrhythmia that weigh against the neuroprotective benefits of cooling the brain tissue. In addition, systemic cooling is typically very slow, as the thermal mass of the body, intrinsic metabolic heat production, as well as defense mechanisms (such as vasoconstriction and shivering) should be addressed. Cooling rates of systemic cooling can often be slow enough to impair the effectiveness of the therapy.

Therapeutic devices, systems, and methods are disclosed herein for cooling the brain, spinal cord, and more generally the body of a subject to clinically beneficial temperatures that help preserve tissue function (such as brain function) following potentially tissue-damaging events, such as hypoxia (as can occur following cardiac arrest or respiratory failure), neurovascular events (such as a stroke), direct trauma (such as a closed head injury or spinal contusion), or perinatal insults (such as difficult deliveries). However, the treatment can be used for any person at risk of tissue injury or inflammation damage from a traumatic or other medical incident. The therapeutic method can be initiated prior to arrival at a medical center, but it is also suitable for in-hospital use.

The therapeutic method may be continued for hours or days as clinically needed and can be used with other methods of brain or body cooling. The therapeutic method can also be used as a bridge to concomitant therapies, such as thrombolysis or thrombectomy (for treating stroke) and cardiopulmonary bypass (for treating cardiac arrest). In the event of cardiac arrest, brain cooling may be initiated before or after spontaneous circulation is reestablished, and even when spontaneous circulation cannot be reestablished prior to presentation at a medical center.

In some embodiments of the new method, the brain is—but is not required to be—cooled by (either separately or in combination with) two functional mechanisms: direct head cooling and cooling of blood that is delivered to the brain. The head can be directly cooled externally by immersing it completely or partially in a container through which cold liquid circulates. As another example, the head can be cooled by applying a well-mixed flow of cold liquid externally against the head. Direct cooling of the inferior surface of the brain and brain stem can be achieved by infusing cold liquid into the upper aerodigestive tract using catheters placed in the upper airway (for example, into the nasal cavity, nasopharynx, oral cavity, oropharynx, and/or hypopharynx). By intermittent or continuous irrigation with non-nebulized cold liquid, an effective and rapid internal cooling of the nasopharyngeal cavity, upper airway, or aerodigestive tract occurs.

Cooling the upper aerodigestive tract and/or scalp causes blood delivered to the brain to be cooled as it flows through the arteries of the neck and head. Optional additional cooling is achieved by delivering cold liquid into the esophagus via a catheter inserted through the mouth with the tip positioned in (or near) the esophagus, for example the mid-esophagus. Alternatively, multiple outlet ports (either from a single or multiple catheters) can deliver even more cooling liquid in the esophagus. The outlet ports in the esophageal catheter(s) can deliver the cold liquid into the proximal, and/or mid, and/or distal esophagus, and/or the stomach.

In some embodiments, the cool liquid circulating from the esophagus and upper airway/aerodigestive tract exits the mouth and mixes with the liquid surrounding the scalp, whence it is withdrawn from the container, optionally cooled and optionally returned to the container, for example through liquid delivery catheters (such as the catheters in the nose, mouth and esophagus). Cooled liquid can be cooled and/or stored in a reservoir external to the head receptacle. In yet other illustrated embodiments described in greater detail below, the liquid can be cooled in the head receptacle without withdrawing it from the receptacle (e.g., the receptacle is the reservoir) by adding ice or other cold items to the liquid. In yet other embodiments in which cool liquid passively flows out of the mouth and nose, the cool liquid can be returned to a cooling reservoir by the action of gravity, for example, by passing through a liquid permeable net that supports the head, or a drain in the receptacle that leads to the reservoir.

While in some embodiments it can be advantageous for the systems, methods, and devices of the present invention to be used with an external cooling reservoir, box, and/or receptacle at least partially surrounding a subject's head, it is not required. In other embodiments, it can be advantageous to use the systems, methods, and devices without a reservoir, box, and/or receptacle at least partially surrounding a subject's head (e.g., to provide greater access to a subject's head). Similarly, while in some embodiments, it can be advantageous to permit cooling liquid circulating within the aerodigestive tract during a procedure to exit passively from a subject's nose and/or mouth as described above, it is not required. In other embodiments, and described in detail below, it can be advantageous to actively remove fluid from the aerodigestive tract (e.g., using a negative pressure device (e.g., a suctioning device) coupled to at least one of the present catheters while the catheter is disposed in a subject's aerodigestive tract).

An initial temperature of liquid used for cooling can comprise various temperature ranges. For example, the initial temperature of the liquid can be in the range of −30 to 30° C. (e.g., −30 to 10° C., −20 to 10° C., etc.). Optimal temperature may vary depending on various factors, such as body size, procedure type, desired brain/body core temperature gradient, and the like. For example, a liquid used for cooling can be maintained at a temperature (such as a substantially fixed temperature) of less than 30° C., less than 10° C., less than −10° C., and the like (such as a temperature of about −17° C.). The liquid can be maintained at any substantially constant temperature (for example, within a range of ±2° C.) by equilibration with a heat exchanger at the desired temperature in a "single fluid pass" configuration or by circulating it between the receptacle/reservoir and a separate heat exchanger cooling unit, adding additional cool liquid as required or by adding cold objects to the reservoir of liquid. Alternatively, the temperature is maintained by adding ice (including dry ice) or other cool objects at a desired temperature to the liquid.

In embodiments in which the scalp is exposed to cooling liquid, forced flow of the liquid over the surfaces of the scalp is achieved, for example, by constantly withdrawing the liquid to be cooled and reintroducing the cooled liquid under pressure into the head receptacle (e.g., through a tube directed at the head). However, other means of liquid agitation within the head receptacle may also be used. Forced flow over internal and/or external body surfaces improves heat transfer by reducing the depth of the boundary layer of immobile cool liquid. Hair may be removed if it has an insulating effect that interferes with effective rapid heat exchange.

One configuration of the cooling method is illustrated in FIG. 1A, which schematically shows the placement of irrigation catheters that deliver a flow of cooling liquid to structures that substantially selectively cool the brain 10 in the head 12 of a subject 14, as opposed to generalized induction of hypothermia throughout the body of subject 14. The sectional view shows (moving anterior to posterior) the nose 16 with nasal cavities 18 (only one shown) and nasopharynx 20. The bottom wall of nasal cavity 18 is defined by the palate, which is divided into the anterior hard palate 22 and posterior soft palate 24. Mouth 26 defines an entrance to oral cavity 28, which leads to a posterior oropharynx 30. Inferior to oropharynx 30 is hypopharynx 32 that is bounded anteriorly by epiglottis 34 and leads inferiorly to the anteriorly situated trachea 36 and posteriorly situated esophagus 38.

In the embodiments shown, targeted cooling of the brain can be achieved, for example, by introducing a continuous or coherent flow of liquid that circulates through the upper airway (e.g., above the level of the trachea and esophagus) and includes the nasal and oral cavities 18 and 28, nasopharynx 20, oropharynx 30, and hypopharynx 32. FIG. 1A provides an example of how to provide this continuous flow by introducing nasal catheters 40 into the nasal cavities and an oral catheter 42 into the oral cavity of subject 14. First and second nasal catheters 40 (only one is shown in FIG. 1A) are inserted into each nostril of nose 16 and advanced until the distal open delivery tip 44 is positioned in the nasal cavity above the hard palate 22 (although it can alternatively be positioned above hard palate 22, soft palate 24, or nasopharynx 20). Oral catheter 42 is similarly inserted into the oral cavity 24 with the open delivery tip 46 advanced toward and positioned, for example, slightly beyond and below soft palate 24 with open delivery tip 46 positioned in (or near) oropharynx 32. In other embodiments, however, oral catheter 42 can be positioned before soft palate 24 (e.g., such that open delivery tip 46 is directed toward oropharynx 32). To help isolate the lungs from the upper airway and aerodigestive tract, an endotracheal tube 48 is shown inserted through mouth 26 and hypopharynx 32 into trachea 36. An optional inflatable peripheral cuff 50 is shown in its expanded condition occluding the lumen of trachea 36.

An inflatable cuff (or balloons)—whether esophageal, tracheal, or other—can be inflated with gas (e.g., air) and/or liquid (e.g., water). In some embodiments, the gas and/or liquid can be chilled to a desired temperature to assist in cooling the tissue with which the inflatable cuff is in contact (e.g., and by effect, cooling the blood flowing to the brain). In other embodiments, the gas and/or liquid can be warmed to a desired temperature (e.g., with respect to the irrigation fluid) in order, for example, to improve a contact/interface with surrounding tissue. Inflating a cuff with fluid can have the additional advantage of pre-equilibrating the cuff with the cooling fluid in a subject's upper airway (e.g., preventing and/or eliminating contraction of the cuff).

Inflatable cuffs can comprise any biocompatible material configured to expand in response to a sufficient outward force. Such material can further be configured such that the cuff responds to an application of sufficient inward force from a portion of the aerodigestive tract (e.g., tracheal/esophageal tissue) by cooperating with the aerodigestive tract to form a substantially fluid-tight seal (e.g., such that water entering the mouth and/or nose through catheters is substantially prevented from moving beyond the cuff). The thickness of the material used to create an inflatable cuff can be varied depending on a number of factors, such as, a desired force with which the cuff should expand, malleability of the cuff in contact with aerodigestive tissue, desired strength of the cuff, a given procedure, a desired location of the cuff within the aerodigestive tract, and the like.

Further, inflatable cuffs can comprise a double balloon structure having a first opening interior to a first balloon and a second opening defined by an outer surface of the first balloon and an inner surface of a second balloon. A first and second opening of a double balloon structure can be filled with the same or different substances.

Inflatable cuffs can also comprise various measurement devices (discussed in detail below) configured to measure information about the cuff (e.g., pressure, temperature, volume, etc.) and/or the tissue (e.g., temperature) with which the cuff is in contact.

The illustrated catheters 40, 42, 48 can be single or multiple lumen catheters. The bores of catheters 40 and 42 are of a sufficient size to permit a flow of a continuous or coherent column of cooling liquid through the catheters and out of open tips 44 and 46, respectively, to establish the coherent flow of liquid that substantially fills the upper airway. One or more optional fronto-tempero-parietal catheters 52 are schematically shown in FIG. 1A positioned to direct a forced flow of cooling liquid against the anterior portion of head 12, for example, against the fronto-parietal portions of the head (e.g., against the forehead or side of the head). One or more optional posterior catheters 54 can also be situated to direct a forced flow of cooling liquid against a posterior portion of head 12, for example, against the occipital portion of head 12. Catheters 52 have open tips 56 oriented within 1-5 cm of the surface of the head, and catheters 54 have open tips 58 similarly situation within 1-5 cm of the head surface.

Although not shown in the schematic illustration of FIG. 1A, each of the catheters is adapted for operative connection to a source of liquid for introduction through the catheter. Catheters 40, 42, 52, 54 are adapted for connection to a sufficient supply of cooling liquid of a temperature adequate to lower the brain to a targeted temperature (such as 33° C. or less), or by a targeted change in temperature within a set period of time (such as 5° C. within 30 minutes or less). Endotracheal tube 48 is adapted for operative connection to a ventilator or other source of respirable gas that can be introduced under pressure for mechanical ventilation of the lungs (not shown). Although the illustrated catheters are shown having end openings for discharging the liquid from the catheter into the aerodigestive tract, the catheters can instead be provided with multiple side holes in the distal 5-10 cm of the catheter to allow liquid to be discharged laterally from the catheter instead of (or in addition to) discharge from the tip. Lateral discharge can help promote well-mixed flow within the aerodigestive tract.

Cooling liquid is introduced through tips 44, 46, 56, 58 of tubes 40, 42, 52, 54, respectively, as shown by arrows in FIG. 1A. The volume of cooling liquid circulates through the upper airway/aerodigestive tract (e.g., above the level of the esophagus and trachea), to at least partially fill the upper airway with the cooling liquid and assure substantial contact between the cooling liquid and the exposed surfaces of the upper aerodigestive tract/airway. In some embodiments, the upper airway and upper aerodigestive tract are substantially filled with the cooling liquid.

Many of the surfaces of the upper aerodigestive tract are irregular (such as the richly vascularized nasal turbinates) and the flow of liquid that moves along the irregular surfaces of the airway can provide superior heat exchange to cool the airway. The mixing induced by a large flow of liquid being introduced into the confined space of the upper aerodigestive tract and returning outside of any catheters or tubes through the airway itself further disrupts any insulative areas as the circulating liquid moves toward the mouth and nose. In some embodiments, liquid passively moves out of the mouth and nose as new cooling liquid moves into the upper airway to continuously replenish the cooling effect of the liquid.

Figure 1B:
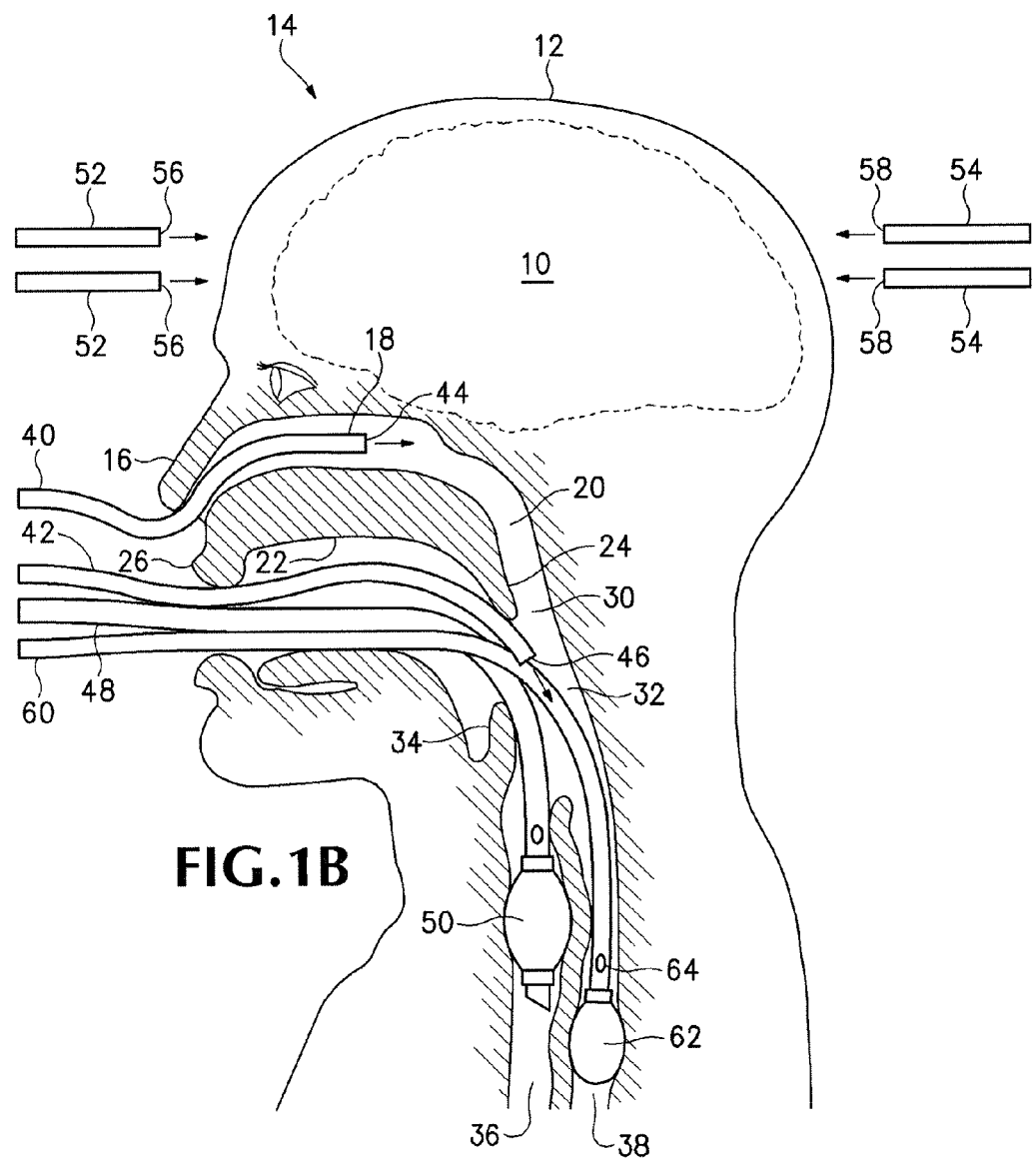
FIG. 1B is a schematic sectional side view of a human head and upper thorax, similar to FIG. 1A, but depicting another configuration of nasal and oral catheters (e.g., with a catheter obstructing flow into the esophagus).

FIG. 1B shows another configuration of the systems and methods illustrated in FIG. 1A. For simplicity, and not by way of limitation, like parts have been given like reference numbers to those found in FIG. 1A. In the embodiment shown in FIG. 1B, an esophageal tube 60 can additionally be inserted through mouth 26 into esophagus 38. Esophageal tube 60 has a distal balloon 62 that is shown in an inflated condition in the proximal or middle portion of esophagus 38 to substantially prevent fluid from moving beyond balloon 62. Additionally, esophageal tube 60 can be operatively connected to a source of cooling liquid (not shown) to introduce a flow of liquid through the lumen of esophageal tube 60 and emerges through side port 64 to thereby serve as an additional source of cooling liquid circulating through the upper airway.

The methods of cooling described in FIG. 1A and FIG. 1B are examples of "selective" cooling of the head and the brain in that cooling of those structures proceeds faster than cooling of other parts of the body. However, a certain amount of non-selective cooling can also occur as well.

Figure 2A:
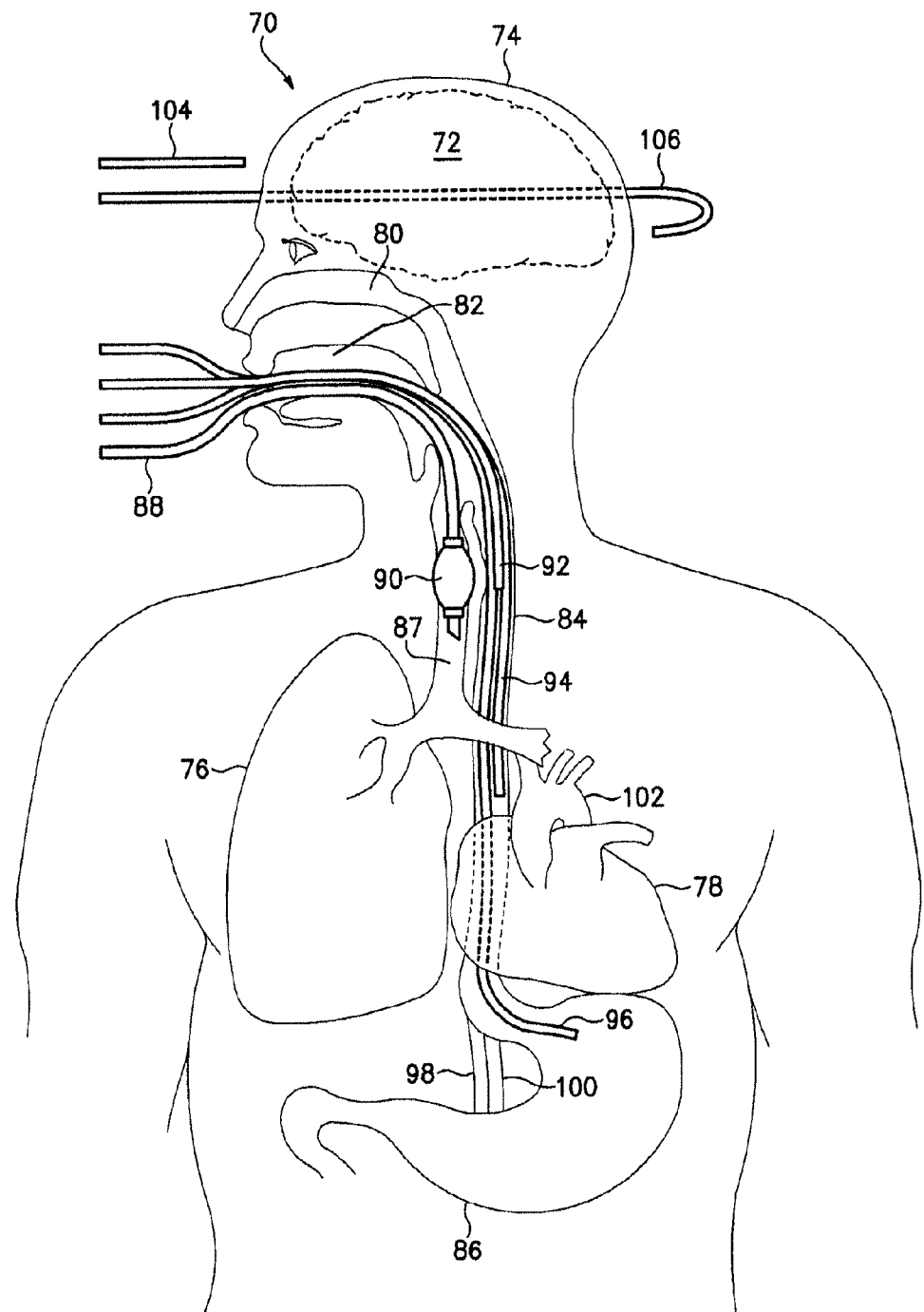
FIG. 2A is a view of the upper thorax and head, illustrating another configuration of oral and nasal irrigation tubes and optional external irrigation tubes configured to direct cooling liquid against the face and head, where the irrigation tubes are configured to deliver cooling liquid to the esophagus and stomach for inducing hypothermia in the body (without more selectively cooling the head and brain).

FIG. 2A illustrates an example of a relatively non-selective cooling method for inducing non-selective hypothermia in a subject 70 by generally cooling the body of the subject without specifically targeting the brain. FIG. 2A schematically shows the subject's brain 72, within head 74. One of the two lungs 76 is illustrated in the chest of subject 70, as is the position of heart 78. The subject's nasal cavity 80 and oral cavity 82 communicate with esophagus 84 and stomach 86, and trachea 87 that communicates with lung 76. In the embodiment shown, no tubes are placed in nasal cavity 80, but an endotracheal tube 88 is positioned in trachea 87 with an optional inflated cuff 90 to isolate the lungs from the flow of cooling liquid in the upper aerodigestive tract. In other embodiments, however, tubes can be placed in nasal cavity 80, only, or in combination with one or more tubes placed in oral cavity 82, such that the one or more tubes can be disposed in the oral cavity, the esophagus, and/or trachea (e.g., to achieve a greater cooling effect). In the embodiment shown, the esophagus and stomach are cooled by three esophageal tubes, namely an upper esophageal cooling tube 92 positioned with a single outlet (e.g., an open end) in the upper esophagus, a middle esophageal cooling tube 94 positioned with a single outlet (e.g., an open end) in the mid esophagus, and a gastric tube 96 positioned with a single outlet (e.g., an open end) in the stomach for cooling the stomach. Although three tubes are illustrated in this example, a single multi-lumen tube with multiple outlet ports could alternatively be used. As previously described, side ports instead of end openings could also be used to increase mixing in the flow.

Cooling liquid can be introduced through all three tubes and delivered to different levels of the digestive tract to provide primary cooling of the esophagus and stomach as the cool liquid returns from the stomach and esophagus. The cool liquid in the stomach contacts the rugae that greatly increases the surface area across which heat exchange with the blood can occur. Cooling liquid in the esophagus and stomach is also in close anatomic proximity to the inferior vena cava 98, superior vena cava (not shown), descending aorta 100, and aortic arch 102 to cool the blood therein as it moves through body, and particularly as the blood moves through the structures of the mediastinum.

Although FIG. 2A only shows tubes inserted in the esophagus and stomach, it will be understood that cooling of the entire aerodigestive tract can occur by side ports or by retroflow of cool liquid through the aerodigestive tract to the mouth and nose. In addition, irrigation catheters can be inserted in the mouth and nose as in FIG. 1A to further increase the flow of cooling liquid through the aerodigestive tract.

External liquid application tubes 104 and 106 can optionally be positioned to apply a forced flow of liquid externally to the head of the subject. Tube 104 is positioned to flow liquid against the frontal area of the head (for example, against the forehead) and tube 106 is positioned to flow liquid against the occipital region.

Figure 2B:
FIG. 2B shows the structures of the mediastinum that form a thermally insulated compartment that helps maintain mediastinal cooling induced by the methods, systems, and devices disclosed herein.

FIG. 2B illustrates that the mediastinum is an anatomic compartment that is somewhat insulated and therefore can retain the cooling effect of the liquid introduced through the esophageal tubes. The mediastium contains the heart, the great vessels of the heart, esophagus, and trachea, and is insulated laterally by the air-filled lungs and inferiorly by the stomach.

All of the cardiac output passes through the veins of the mediastinum. Internal cooling of the mediastinum can be accomplished by cooling substantially all of the aerodigestive tract, from the nares to the pyloris (excluding lungs). The mediastinum is insulated from heat from the rest of the body by the lungs, larynx, and stomach. The lateral aspects of the mediastinum are bordered by the lungs, which have low mass and are kept cool by the normal function of ventilation. The inferior aspect of the mediastinum can be cooled by cooling the stomach. The superior aspect of the mediastinum, e.g., the neck, can be cooled by cooling the upper airway. Insulation of the mediastinum enables cooling of the venous blood in the vena cava more efficiently than if similar cooling were to be performed on the vena cava within the abdomen. If vena cava cooling were attempted in the abdomen, heat from the surrounding organs would also be delivered to the vena cava, which could significantly impede cooling.

Figure 3:
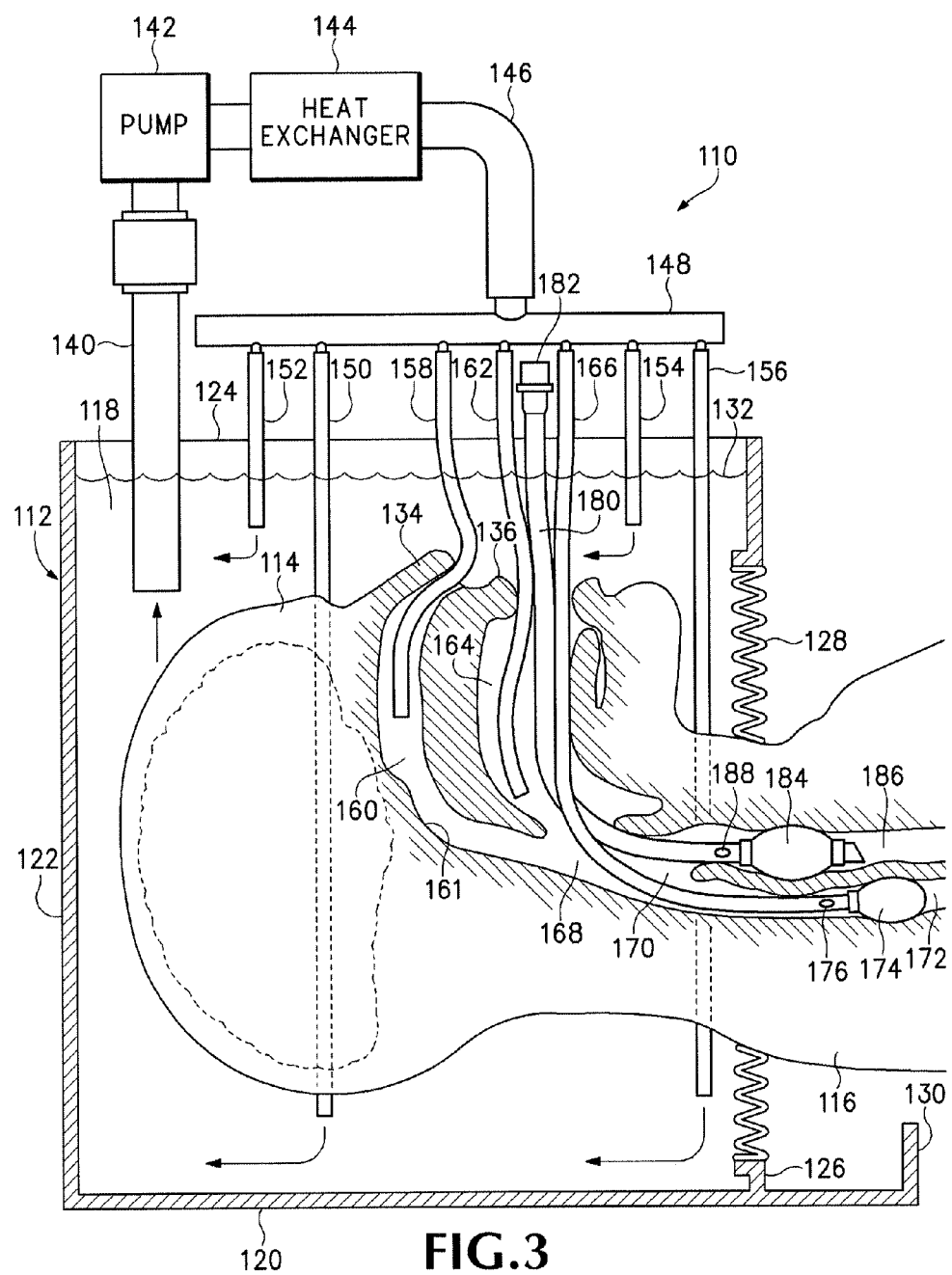
FIG. 3 is a partially schematic side view of the head of a supine subject placed in a container of cool liquid with liquid instillation and another configuration of tubes (e.g., recirculation tubes inserted in the nose, mouth, and upper esophagus, and an endotracheal tube in the trachea).

FIG. 3 provides an example of another brain cooling device 110 for carrying out the selective cooling method, wherein a container 112 at least partially encloses a head 114 of a subject 116 who is in a supine position (with the face up). Head 114 can be partially or totally immersed in cool liquid 118, but the illustrated embodiment shows total immersion of the head and face. In the embodiment shown, the container 112 is a rectangular or square box having a solid flat bottom wall 120, three solid upright side walls 122 (only one is shown in FIG. 1), and open top face 124. Side walls 122 are connected to bottom wall 120 with liquid tight seals. Each of side walls 122 is also connected to adjacent side walls 122 with liquid tight seals. One of side walls 122 (e.g., side wall 126) can be configured to receive a subject's head and/or neck. The bottom wall 120 and side walls 122 and 126 may, for example, be preformed out of contiguous material, as in a seamless unitary piece of molded plastic. Open top face 124 defines a square or rectangular opening large enough to provide access to the entire face. An upright side wall 126 defines a head and/or neck receiving opening that contains an annular flexible seal 128 to inhibit flow of liquid from container 112 (e.g., and sized to adjustably accommodate a subject's neck). An overflow trough 130 may extend along the bottom edge of face 126 to collect liquid that leaks through the seal such that the liquid can, for example, be re-circulated to the container by a recirculation pump (recirculation tubing not shown). For example, the dimensions of the container can be approximately 25 to 50 cm in length, width, and height for an adult-sized box and 10 to 25 cm on all sides for an infant-sized box.

The reservoir of cool liquid 118 can substantially fill container 112. The liquid in the box has a top liquid level 132 that, in the illustrated embodiment, is within 2-10 cm of the top edge of the box, such that the liquid completely submerges head 114 below liquid level 132. With the liquid at this level, both the nose 134 and mouth 136 of subject 116 are completely covered with liquid, and the upper airways can passively fill with liquid from the container in addition to being actively filled with liquid pumped into the airway, as described below. The area around the head and in the upper airways can therefore be a substantially uninterrupted continuum of cooling liquid that can establish thermal exchange with the anatomic structures that come into contact with the continuum of liquid. In other embodiments, as described above, top liquid level 132 can comprise a level such that mouth 136 and/or the nose 134 are not completely submerged in cool liquid 118. In such embodiments, head 114 can still be cooled passively by cool liquid 118, and the upper airways can be actively filled with liquid pumped into the airway, as described below.

In the embodiment shown in FIG. 3, device 110 can be configured to control the temperature of the liquid in container 112. Device 110 can be configured in various ways to permit control of the temperature of the liquid in the container, such as, for example, configuring container 112 similarly to a refrigeration unit, adding cool objects (such as ice) to the liquid, and/or using endothermic chemical reactions (such as ammonium nitrate in water) in the walls of the container to cool them. In the embodiment shown, liquid in container 112 is cooled externally to the container by pumping it from the container to a heat exchanger 144, where it is cooled and pumped back to the container. The heat exchanger can be of any type, such as a shell and tube heat exchanger, a plate heat exchanger, a regenerative heat exchanger, an adiabatic wheel heat exchanger, a fluid heat exchanger, or a dynamic scraped surface heat exchanger. Additional information about such devices is readily available, for example, in Sadik Kakac and Hongtan Liu *Heat Exchangers: Selection, Rating and Thermal Design,* 2nd Edition, CRC Press (2002) (ISBN 0849309026).

FIG. 3 further shows an intake conduit 140 that extends from container 112 to a liquid pump 142. Pump 142 is coupled to heat exchanger 144. Outlet conduit 146 extends from heat exchanger 144 and communicates with an elongated distribution conduit 148 that provides multiple catheter connection outlets. Although the illustrated embodiment shows a single pump, more than one pump can be used. The pump can also be manually operated (for example, by manually rotating or reciprocating a pump handle) or non-manually operated (for example, by actuating an electrically operated pump).

Liquid circulation conduits of various lengths are connected to the outlets on distribution conduit 148 and extend through the open top face 124 of container 112. Four of them are liquid circulation tubes 150, 152, 154, 156, which can deliver flow of liquid to the scalp and face. Tubes 150 and 156 extend substantially to the bottom of container 112 for deep recirculation of liquid. Tubes 152 and 154 extend into the top portion of container 112 to provide more recirculation of liquid in the container. Another of the liquid circulation conduits is a first liquid delivery catheter 158 for delivering cool liquid to the nasal cavity 160 of the subject. First liquid delivery catheter 158 can be any length sufficient to extend from distribution conduit 148 to a distance of about 3 to 6 cm into the nasal cavity 160 with the outlet of catheter 158 directed at (or near to) nasopharynx 161. Another of the conduits is a second liquid delivery catheter 162 for delivering cool liquid to the oral cavity 164 of the subject. Catheter 162 can be any length sufficient to extend a distance of about 6-12 cm into oral cavity 164 with the outlet of catheter 162 directed at (or near to) oropharynx 168.

In the embodiment shown, device 110 further comprises a third liquid delivery catheter 166 configured similarly to a nasogastric tube. Catheter 166 extends from distribution conduit 148 and can comprise any length sufficient to extend through oral cavity 164, oropharynx 168, hypopharynx 170, and into esophagus 172 (e.g., 25 to 30 cm beyond mouth 136). Catheter 166 can be a multi-lumen catheter with a balloon tip 174 that is selectively inflatable, for example, by using a source of pressurized air (e.g., a syringe (not shown)) that introduces the air through one of the lumens to the balloon tip 174. Another lumen of catheter 166 opens to a side port 176 that is in fluid communication with distribution conduit 148 (e.g., such that side port 176 can deliver cool liquid into the proximal esophagus). Side port 176 is proximal to balloon tip 174 so that when balloon tip 174 is inflated the liquid delivered into esophagus 172 does not flow beyond balloon tip 174 into the distal gastrointestinal tract (such as the stomach), but can instead move in a proximal direction through the upper airways.

Device 110 can also comprise multi-lumen endotracheal tube 180 having a conventional coupling collar 182 configured to be coupled to a source of ventilation (not shown). Suitable sources of ventilation include any device configured to introduce a non-toxic fluid (such as a gas) with oxygen in it. Examples of such sources include a manual ventilation bag or a mechanical ventilator that communicates with the primary lumen of tube 180. The primary lumen of tube 180 is in fluid communication with the lower airways and lungs. Endotracheal tube 180 includes a conventional distal cuff 184 that can be selectively inflated (e.g., after insertion) by introducing a fluid (e.g., a pressurized fluid, such as gas from a syringe) through a secondary lumen of tube 180 to secure the tube in place within the trachea 186, to provide an effective seal between tube 180 and the walls of the trachea (e.g., improving efficiency of ventilation), and to substantially prevent the entry of liquid from the upper airway into the lower airways and lungs.

Although the illustrated embodiment of endotracheal tube 180 in FIG. 3 includes cuff 184, the cuff is not always required to substantially seal the airway. For example, in small or pediatric subjects, the endotracheal tube itself may be large enough to effectively occlude passage of liquid between tube 180 and the walls of trachea 186. In still other embodiments, endotracheal tube 180 can be configured to prevent a patient's tongue from interfering with the cooling procedure. In the illustrated embodiment (FIG. 3), a suction port 188 is located on the side of tube 180 proximal to cuff 184. Port 188 communicates with a tertiary lumen in tube 180 and is coupled (e.g., connected) to a source of negative pressure source (not shown) that is configured to withdraw liquid from the trachea. The removed liquid can be recirculated into the reservoir of liquid 118 in container 112.

In use, head 114 of subject 116 in need of brain cooling is placed in container 112 by inserting head 114 through flexible seal 128. A thickened liquid-resistant emulsion or gel (such as petroleum jelly) can be applied externally in a continuous ring around the neck to enhance the liquid-resistant seal. A soft, liquid-resistant foam strip can also be placed around the neck and may be layered to achieve a desired thickness. Flexible seal 128 can be configured to provide a substantially liquid-tight seal without obstructing arterial or venous flow of blood through the neck. In some embodiments, a plastic liner (not shown) can also be placed in container 112 around head 114 to provide an additional barrier to loss of liquid from container 112.

The subject 116 may optionally be prepared for the brain cooling procedure by removing hair from the head, for example, by cutting the hair or shaving the head to improve conductive loss of heat externally from head 114 to surrounding cool liquid 118. If the subject is conscious, sedation may also be administered (for example, intravenously administering a benzodiazepine or narcotic) to lower the level of consciousness and/or induce transient amnesia. Once the subject's head 114 is positioned within container 112, open top face 124 of container 112 provides access to the interior of the container. Deep circulation tubes 150 and 156 can be positioned around head 114 with their outlets proximal to bottom wall 120. Superficial circulation tubes 152 and 154 can be positioned above head 114 with the outlets of tubes 152 and 154 directed at the subject 116 (e.g., at the face and scalp). Catheter 158 can be lubricated in a conventional fashion and can be inserted through a nostril into nasal cavity 160 (e.g., 3 to 6 cm, or such that the tip of catheter 158 is adjacent to (or near) the vascularized surfaces of the turbinate mucosa and near the cribiform plate of the ethmoid bone that supports the inferior surface of the cerebral cortex) with the outlet of catheter 158 directed at (or near) nasopharynx 161. Esophageal catheter 166 is inserted through the mouth (e.g., 25 to 30 cm) into the proximal esophagus 172. Cuff 174 can be inflated after esophageal catheter 166 is positioned appropriately. Further, endotracheal tube 180 can be inserted into trachea 186, and cuff 184 can be inflated. The tertiary lumen of endotracheal tube 180 is connected to a negative pressure source (e.g., a suction device) such that fluid can be removed from trachea 186.

Liquid pre-cooled to a desired temperature is introduced into container 112 until the liquid level 132 reaches a desired level (e.g., above the intake level of intake conduit 140). Liquid can be circulated by activating pump 142. Pump 142 is configured to remove liquid from container 112 through conduit 140 and into heat exchanger 144. Pump 142 can pass liquid to heat exchanger 144 under pressure (e.g., 20-60 cm $H_2O$). Liquid can then exit heat exchanger 144 through outlet conduit 146 and into distribution conduit 148. The liquid is then distributed among the outlets and respective conduits that lead to container 112. Forced flow can be induced in container 112 around the head by introduction of cool liquid through circulation tubes 150, 152, 154, and 156. This flow can enhance heat transfer from the surface of the head and/or face.

Pump 142 also circulates the cool liquid through tube 158 into the nasal cavity, through tube 162 into the oral cavity, and through tube 166 and out of port 176 into the proximal esophagus. The liquid introduced through the tubes merges with cool liquid that passively enters from container 112 to substantially fill the upper airways with a cool liquid that is in a substantially uninterrupted liquid continuum with the reservoir of cool liquid around head 114. A continuous recirculation of liquid occurs from the upper airways to the reservoir of liquid around the head and back into the upper airway. The liquid may also be continuously cooled to maintain a desired temperature that induces rapid cooling of the brain to a desired therapeutic temperature.

As previously noted, the neck of the subject rests in an opening in one wall of the container. The opening is provided with a sealing means, such as a circumferential flexible sealing material that circumscribes the neck to help enhance the liquid-tight seal. The liquid-tight seal around the neck can include a thickened liquid-resistant emulsion or gel (such as petroleum jelly) that is applied to the skin to make a continuous ring around the neck. A soft liquid-resistant foam strip may be placed around the entire circumference of the neck (for example, over the gel) and may be layered to achieve a desired thickness. Finally, the flexible sealing material can be tightened around the neck to a pressure sufficient to provide a substantially liquid-tight seal without obstructing arterial or venous blood flow in the neck.

In one embodiment, the neck-receiving opening is a "U"-shaped opening in the side wall 126 of container 112, and the width of the "U" is wider than the neck. Attached to the inner edges of the opening is a liquid-resistant flexible material (such as rubber or vinyl). At least 2 inches of free material extends from the inferior aspect of the defect and sufficient material extends from each lateral aspect of the defect to substantially extend to the other side of the opening. To finish the seal around the neck, the excess material superior to the anterior surface of the neck can be held together by a fastening device (e.g., clips). The excess material from both sides (if any) can be wrapped around each other before being temporarily fastened (e.g., clipped) together.

Figure 4:
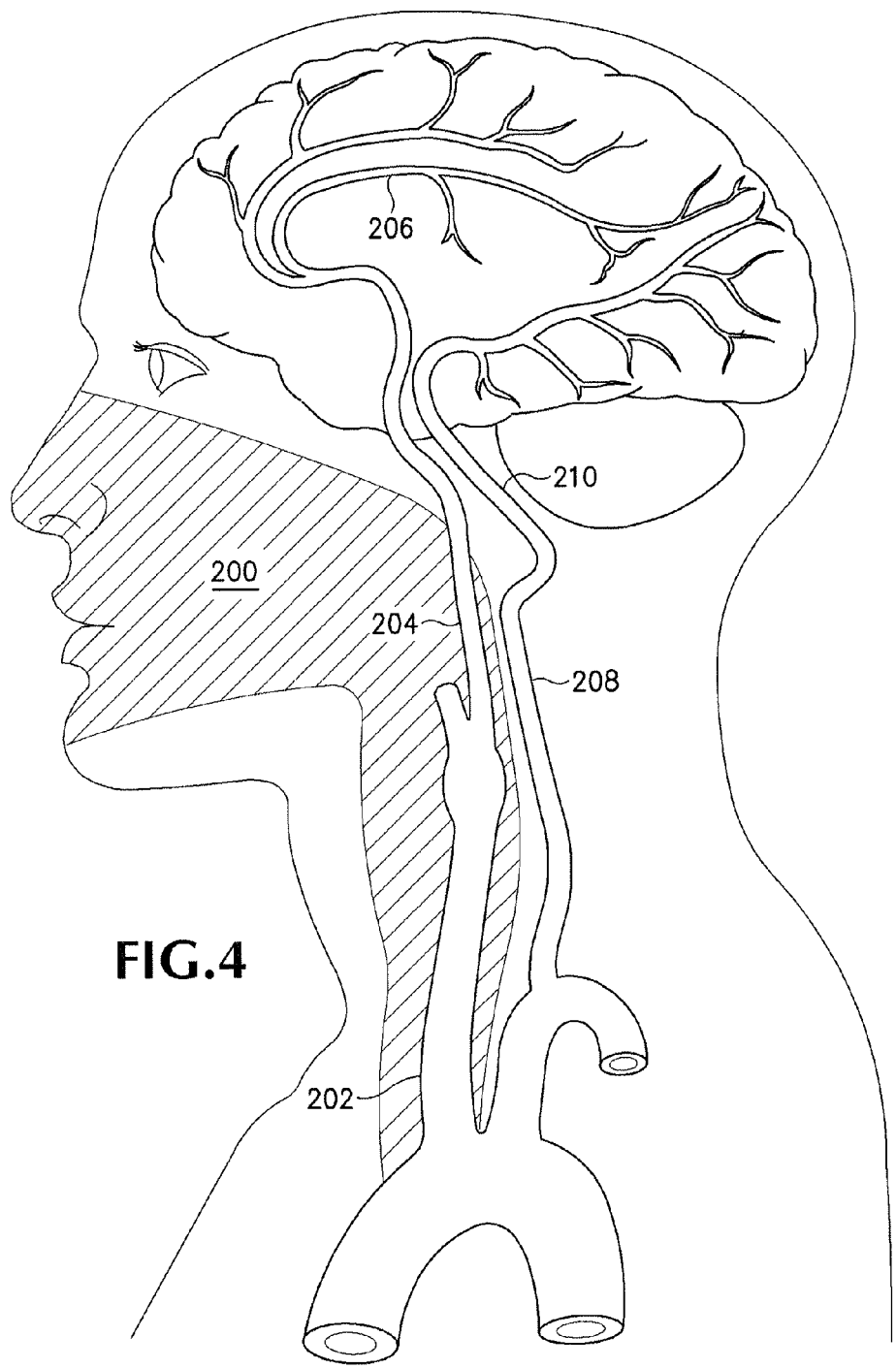
FIG. 4 is a schematic side view of the head, neck, and chest of a subject illustrating the upper airway and some of the blood vessels that can be cooled by circulating cool liquid through the aerodigestive tract during selective cooling of the brain.

FIG. 4 shows a shaded area that corresponds to the upper airway that can be filled with cool liquid as discussed in the present invention. The upper airway includes the nasal cavity, nasopharynx, oral cavity, oropharynx, and hypopharynx. The upper airway is defined by the walls of the pharynx that are laterally flanked in close association on either side by major blood vessels that perfuse the brain. As shown in FIG. 4, these blood vessels include common carotid artery 202 and internal carotid artery 204, which in turn supplies anterior cerebral artery (not shown) and middle cerebral artery 206. Another blood vessel in close anatomic association to the upper airway includes the vertebral artery 208, which is a branch of the subclavian artery and that in turn forms the basilar artery 210 that supplies blood to the vertebrobasilar system. The blood flowing through the arteries of the neck can be conductively cooled by close association with a cool liquid that fills the upper airway, and this cooled blood can quickly lower the temperature of the brain as the blood perfuses the brain.

Further cooling of the blood that perfuses the brain can be achieved by the introduction of cool liquid into the proximal esophagus where the cool liquid comes into closer contact with mediastinal and lower neck structures, including the common carotid artery 202.

In this novel therapy, cooling of the blood can start in the aortic arch if there is cold liquid flow in the esophagus and can continue throughout the length of the common and internal carotid arteries, which are in close proximity to the upper airway filled with circulating cold liquid. The posterior circulation (vertebral and basilar arteries) can also be cooled. Cooling can continue in the Circle of Willis, itself, which is separated from the upper airway by a thin layer of soft tissue and bone. In many cases, total carotid blood flow is approximately 0.8 L/minute. This blood is cooled by delivering sufficient cold liquid to fill the esophagus and upper airway to achieve a sufficiently large and/or rapid drop in peri-arterial tissue temperature. Blood moves very rapidly from the heart to the brain and does not spend significant time in contact with surrounding tissue. Nasal-based selective cooling strategies do not provide sufficient time for the blood to equilibrate with surround cool tissue as it passes from the heart to the brain. Irrigating the nose, pharynx, and esophagus creates a long cooling column of cold tissue with which the blood can equilibrate, leading to greater degrees of equilibration and cooling for the arterial blood. Direct cooling of the scalp and upper airway can complement hematogenous cooling, as it also results in a temperature gradient within the brain, with surface temperatures colder than deep in the brain. This gradient is offset by flowing blood since the cerebral arteries traverse long distances along the relatively cooler surface of the brain before delivering cooled blood to deeper brain structures.

Using the disclosed method, focal or isolated cooling of the head and/or brain is achieved without the adverse physiological and medical consequences or technical difficulties of cooling the entire body or large portions of it. Brain cooling can be applied continuously or intermittently for a sufficient period of time to avoid damage to the brain, and this period can extend for minutes, hours, days, or weeks. In some embodiments, the cooling continues for at least 3 hours, at least 4 hours, at least, 8 hours, at least 12 hours, at least 24 hours, at least 48 hours, at least one week, or longer. The period of time during which cooling is continued is determined by the condition of the patient and the clinical judgment of medical personnel. The temperature of the cool liquid can be changed over time in accordance with therapeutic needs. For example, the liquid may initially be cooled to 10° C. or less (for example, less than zero ° C.) to induce rapid brain cooling and inhibit the development of brain edema, adverse metabolic changes, or reperfusion injury. After the first few hours or even days of use, the temperature of the liquid can be increased, for example to 20-30° C., to cool the brain with a lesser risk of hypothermic damage to soft tissues.

This method can produce cerebral cooling, for example, in an estimated 5-15 minutes compared to 3-5 hours demonstrated in human studies with many other prior art hypothermic treatments. Therapy may be started in the field (outside a hospital setting) to accelerate the initiation of treatment and reduce the elapsed time to achieving the temperature goal following the onset of illness. The devices, systems, and methods can be used by someone having only basic emergency medical skills, such as the ability to place the catheters and insert an endotracheal tube. The simplicity of the method will also allow for rapid application of treatment in a broad array of clinical situations. The cool liquid can be—but is not required to be—significantly cooler than ice water used in previous human studies and most animal studies, thereby providing a large temperature gradient that promotes deeper and more rapid brain cooling.

Combining the scalp, upper airway, and cerebral blood cooling provides rapid and effective cerebral cooling. The method is particularly effective because it can optionally cool all of these structures using a common pool of circulating cold liquid. This method of aggressive local cooling is believed to be effective at rapidly cooling the brain even in the absence of spontaneous circulation, although circulating blood is believed to further accelerate the cooling. The disclosed method also permits deeper levels of hypothermia to be achieved, which may help to realize the possible benefits of "suspended animation." This treatment also leaves open the possibility of salvaging life and neurological function even in those who do not achieve restoration of spontaneous circulation in the field. After arrival at an appropriately equipped medical center, whole body and brain blood flow can be reinstituted using cardiopulmonary bypass while more aggressive and time consuming attempts to restore and maintain spontaneous circulation are explored. If the brain is cooled, greater neurological recovery can be achieved even if the restoration of circulation is significantly delayed.

The circulation of cool liquid around the head can also be effective, though it is not required. Factors that functionally insulate the scalp from local hypothermia treatment include scalp hair, the boundary layer effect, and layers of material and air between a cold helmet and the scalp. The direct contact of scalp structures with the circulating liquid helps avoid these problems.

Direct cooling of the inferior surface of the brain is believed to occur more rapidly than scalp cooling due to thinner protective layers of bone and soft tissue. Bone between the upper airway and the brain is approximately half as thick as bone in the scalp and the soft tissue layer is ¼ the thickness of the scalp.

Figures 5A, 5B, 5C:
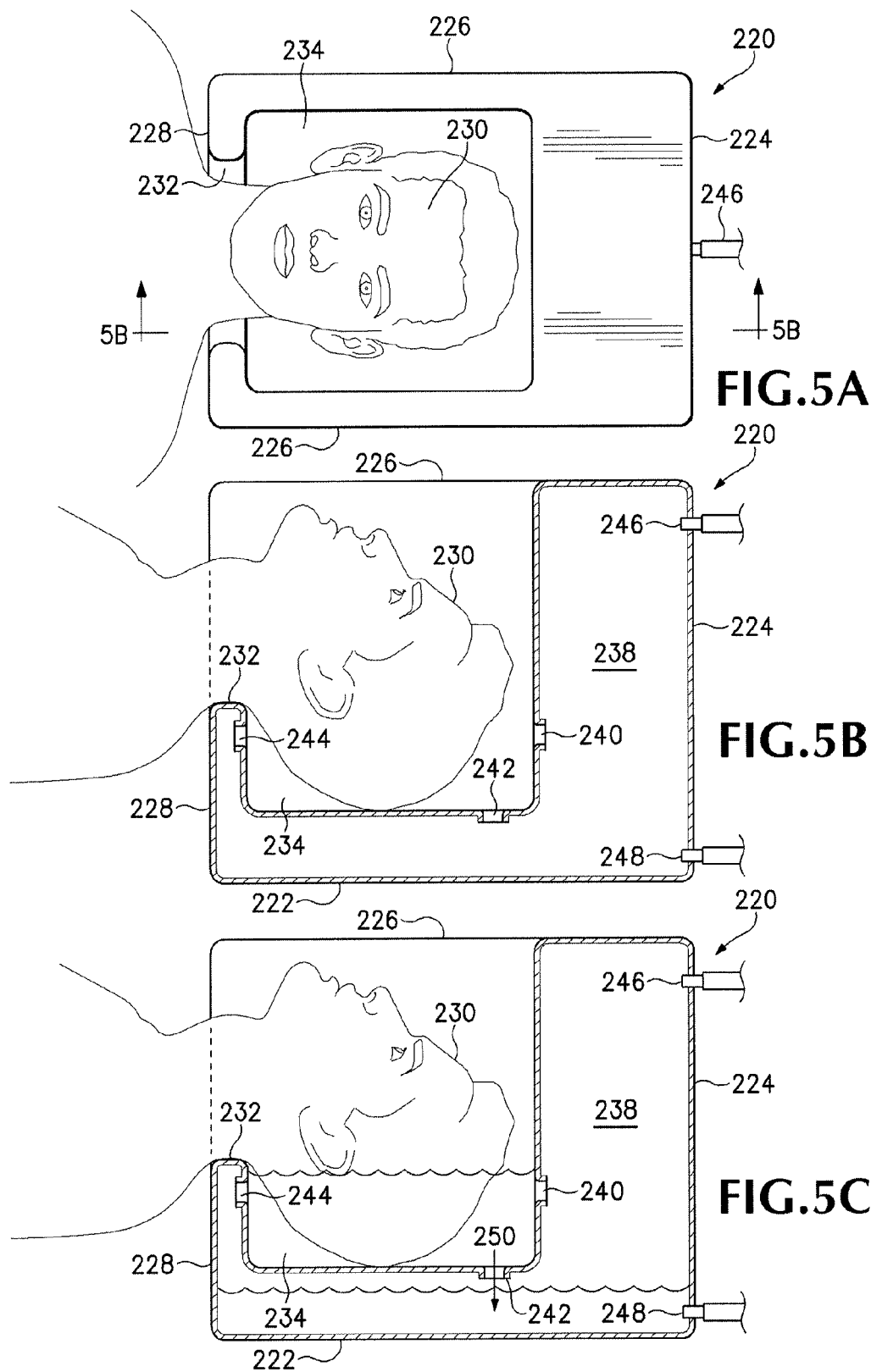
FIG. 5A is a top view of a head receptacle with a surrounding cooling liquid reservoir, with a head of a subject placed in the receptacle.
FIG. 5B is a side-view of FIG. 5A illustrating extension of the neck of the subject.
FIG. 5C shows the device in use, with cooling liquid filling the receptacle.

An additional example of a device suitable for use with either selective or non-selective cooling is shown in FIGS. 5A-5C. The device is a head cooling box 220 having a rectangular base 222, a rectangular rear wall 224, two opposing side walls 226, and a front wall 228. Each of walls 224 and 226 are sufficiently high to extend above the head 230 of a subject within the box, even when the head is tilted with the head in extension as in FIGS. 5A-5C. However, front wall 228 has a cut-out support portion 232 (FIG. 5A) for receiving the neck of the subject.

Spaced from and parallel to the outer walls of box 220 are a set of inner walls that form a head receptacle 234 that is sufficiently large to receive the head 230 as shown in FIGS. 5A-5C, with the neck of the subject resting on support portion 232. Between the head receptacle and the outer walls the box forms a reservoir 238 that partially or completely surrounds receptacle 234 for storing a sufficient volume of cool liquid to circulate through the subject and to be applied externally against the scalp. Reservoir 238 extends behind and below receptacle 234 and communicates with receptacle 234 via one or more openings that form drains 240, 242, and 244. In the illustrated embodiment, drain 240 is in a rear wall, drain 242 in a bottom wall, and drain 244 in a front wall of receptacle 234. An upper port 246 extends through rear wall 224 near the top of box 220, and a lower port 248 extends through rear wall 224 near base 222 of box 220.

In use, the head 230 of a subject in need of treatment can be placed in box 220 with the neck in cut-out portion 232 and the head tilted back in extension. Cool liquid is introduced into reservoir 238 to provide a large volume of cool liquid that can then be circulated though irrigation catheters (not shown) into the aerodigestive tract of the subject as described earlier. The cool liquid is initially delivered into reservoir 238 through upper port 246 and is subsequently withdrawn through lower port 248 and returned through drains 240 and/or 242 and/or 244 after coming into contact with the subject. As liquid is introduced into the aerodigestive tract, it flows into and through the aerodigestive tract until it eventually passively exits the mouth and nose of the subject without being suctioned or removed through a catheter or other tubing. As the liquid emerges from the mouth and nose, it collects in receptacle 234 around head 230 to further cool the head externally to lower brain temperature and drains into reservoir 238 via drains 240-244. The rate at which liquid can return from receptacle 234 to reservoir 238 through one of more of the drains is adjusted by the degree to which the drains are opened, and the position and number of open drains. In the illustrated embodiment of FIG. 5C, bottom drain 242 is open while side drains 240 and 244 are closed so that liquid in receptacle 234 passively flows under the influence of gravity into the underlying portion of the reservoir, as shown by the arrow 250. Adjusting the rate at which liquid drains from receptacle 234, relative to the rate at which liquid enters the receptacle, determines the level of liquid in receptacle 234.

In the illustrated embodiment of FIG. 5C, the liquid level in surrounding reservoir 230 is lower than the level of bottom drain 240, which permits drainage through bottom drain 242. However, in those instances in which a larger volume of cool liquid is provided in surrounding reservoir 238, the liquid is still maintained at a level below side drains 240 and 244 which are open (while bottom drain 242 is closed).

An alternative embodiment is shown in FIGS. 5D and 5E, in which corresponding parts from FIGS. 5A-5C are given like reference numbers for simplicity, but not by way of limitation. This embodiment differs from the prior version, however, in that the front wall 228 has a height adjustment member 252 that fits on front wall 228 and can be moved toward and away from base 222 to adjust the height of the support for the neck of a subject. Adjustment member 252 is capped with a cushion 254 for protection of the neck of the subject and allows for a variable amount of neck extension. The top of reservoir 238 is also covered by a lid 256 that pivots at hinge 258 to open and close reservoir 238. The reservoir may be opened, for example, to add ice or other cold objects to reservoir 238 when cooling of liquid within it is desired.

Figure 5F:
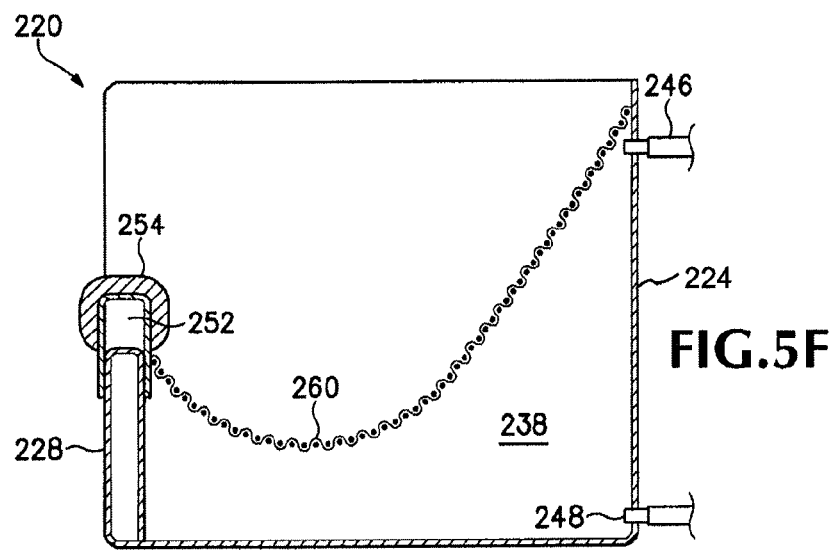
FIG. 5F is yet another embodiment of the head receptacle, in which a mesh net forms the receptacle that supports the head over the reservoir of cooling liquid, and forms a permeable barrier through which the liquid returns from the receptacle to the reservoir.

Yet another embodiment of the box is illustrated in FIG. 5F wherein the box 220 forms the reservoir for holding cold liquid, and the front wall of the box is of a reduced height or has a cut-out portion for receiving the head with the neck supported on cushion 254 of height adjustment member 252. However, the head receptacle is formed by a liquid permeable net 260 that covers receptacle 238 for holding the head of the subject during hypothermic treatment. Net 260 is secured along one edge to front wall 228 below the level of padding 254 and along an opposite edge to rear wall 224 at the top of box 220. Net 260 therefore forms a liquid permeable support sling for the head of a subject, so that as liquid flows through then out of the aerodigestive tract, the liquid spills on to and through net 260 to be returned to underlying reservoir 238.

Figure 6A:
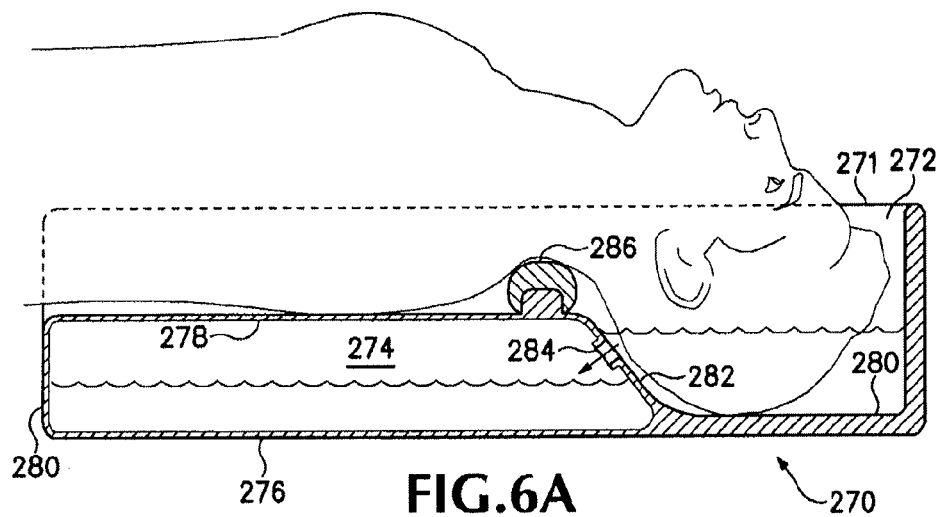
FIG. 6A is a side view showing in cross section a back support and head receptacle, wherein the back support serves as the reservoir of cooling liquid.

In the embodiment of FIG. 6A, the cooling device is in the form of a backboard 270 that contains both a head receptacle 272 and a reservoir 274 for holding a supply of cool liquid. Receptacle 272 and reservoir 274 are in a side-by-side relationship with one another instead of the reservoir surrounding the receptacle as in previously described embodiments. Backboard 270 has a flat rectangular base 276 that is large enough to accommodate the upper portion of a body, for example, from the waist or mid-thorax to the top of the head. A top surface of backboard 270 is formed by a flat body support 278 that is spaced from and held parallel to base 276 by opposing sidewalls 271 (only one of which is shown in phantom), an upright bottom wall 280, and an inclined top wall 282 that separates reservoir 274 from receptacle 272. Sidewalls 271 are of the same height as the top of receptacle 272 to thereby also form the sidewalls of receptacle 272.

Inclined wall 282 slopes from body support surface 278 down to bottom surface 280 of receptacle 272. A drain 284 is provided through inclined wall 282 near the junction of wall 282 with support surface 278 to drain liquid from receptacle 272 back into reservoir 274 when the level of liquid in receptacle 272 rises above the level of liquid in reservoir 274, as illustrated by the arrow through drain 284 in FIG. 6A. A cushioned neck support 286 is positioned on body support 278 near inclined wall 282 to protect and assist with the extension of the neck of a subject placed on backboard 270.

In use, a subject can be placed face-up on backboard 270 with the neck extended and the head in receptacle 272. The desired irrigation catheters are inserted in the aerodigestive tract of the subject (not shown) and liquid from reservoir 274 is pumped through the catheters into the aerodigestive tract for cooling the patient. The irrigation liquid then flows out of the nose and mouth of the subject and collects in reservoir 272 to be returned to reservoir 274 though drain 284. Backboard support 278 is preferably thermally conductive (for example made of metal) so that the cool liquid in the backboard also cools the body of the subject directly. This direct cooling of the subject's back is particularly advantageous for providing cooling of the spine in patients who may have incurred a spinal cord injury that could benefit from such cooling to reduce inflammation and swelling.

Another embodiment of the backboard cooling device is shown in FIG. 6B, which is similar to the embodiment of FIG. 6A, except that body support surface 278' is inclined upwardly to lift the shoulders and neck of the subject. Raising the upper torso in this fashion helps protect the airway and inhibit the entry of liquid into it. It also appropriately positions the head of the patient for intubation and introduction of the irrigation catheters in the aerodigestive tract. The backboard cooling device of FIG. 6B is also shown placed under the back of a patient who is lying face up on a stretcher 288, so that the cooling method can be performed on the subject either in a hospital on en route (for example, while in an ambulance or in transit to a hospital).

The embodiment of FIG. 7 illustrates an embodiment of the cooling device that is suitable for treating a subject who has sustained potential spine injuries and requires stabilization of the spine to avoid additional injury, such as damage to the spinal cord. This embodiment includes a large rectangular tub 290 that is longer and wider than a flat body support board 292 that is suspended above or within tub 290. Support board 292 has lateral extensions that form right and left arm support members 294 and 296 and a superior extension that forms a head support 298. In some embodiments, tub 290 is filled with liquid 300 that contains sufficient ice 302 to cool liquid 300 to a desired temperature. In other embodiments, tub 290 can be filled with cooled fluid from a chilling unit and continually refreshed with cooled recirculated liquid. Tub 290 therefore provides an underlying large reservoir of cool liquid for introduction through irrigation tubes (not shown) into the aerodigestive tract of a subject placed on support board 292. In some embodiments, a patient (not shown) can be positioned supine on support board 292 with the head turned to the side so that internally circulated liquid (and/or any liquid sprayed on the head) can return passively to tube 290 to be cooled there for recirculation to the patient. In other embodiments, as discussed in detail below, liquid can be actively removed (e.g., suctioned through at least one catheter) from the patient.

Figure 8:
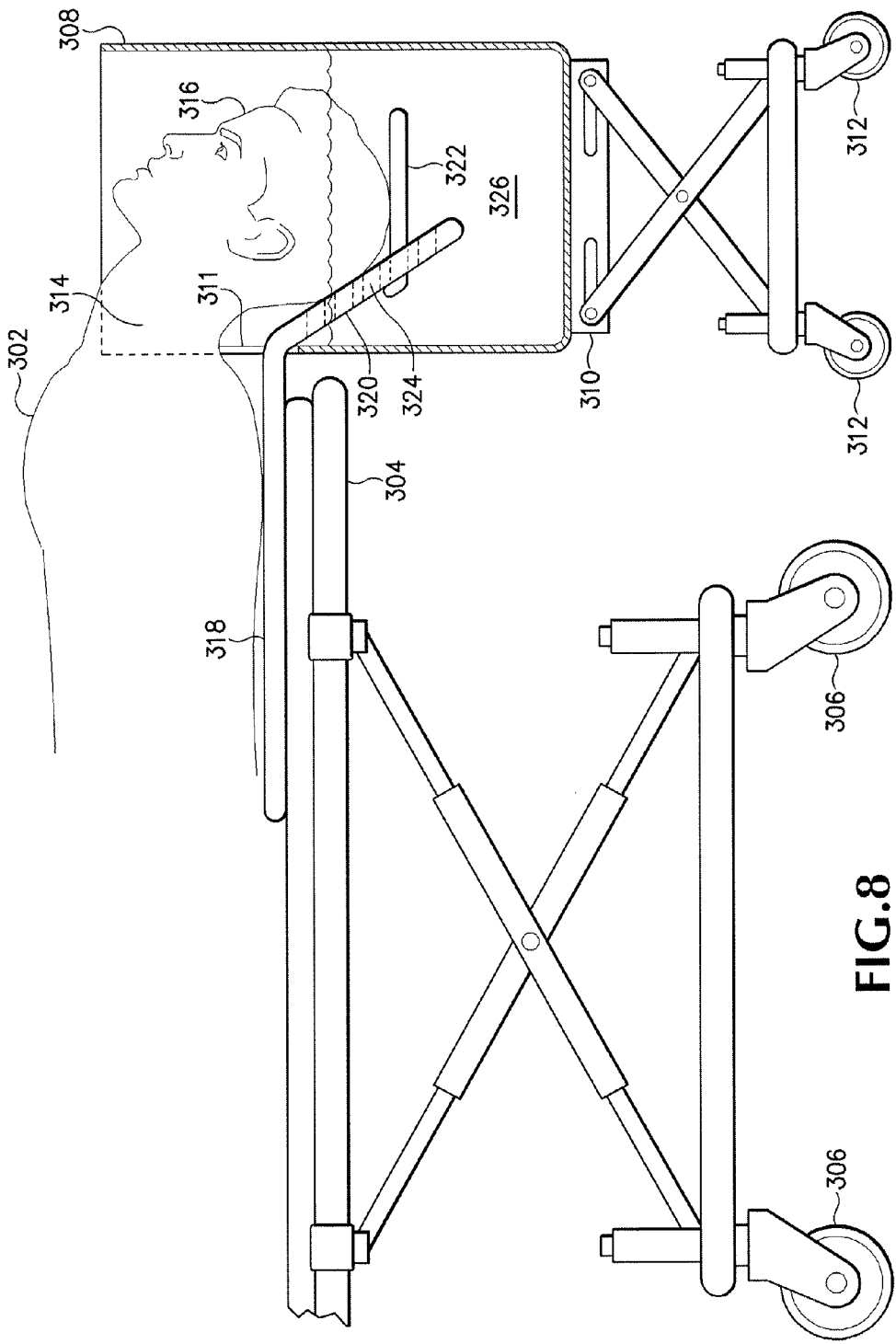
FIG. 8 is a side view of a patient being transported on a stretcher, with a head receptacle that also serves as the cooling liquid reservoir, and the head receptacle moves with the stretcher.

FIG. 8 illustrates a mobile version of the cooling device in which a subject 302 is lying supine on a stretcher 304 that is supported by wheels 306 for transportation of the subject on the stretcher. A separate reservoir 308 is supported on a cart 310 having an adjustable height, and which is also supported on wheels 312 for movement with the stretcher. Reservoir 308 is a large capacity tank that has a cut-out or reduced height portion 311 in which the neck 314 is placed so that the head 316 of the patient can be tilted back and into reservoir 308. A backboard is placed under the back of the patient to support the back and head. The backboard is an angled member that includes several sections: a flat back support 318 for horizontal placement on stretcher 304, an inclined neck support 320 that fits into reservoir 308 through the neck-receiving portion of the reservoir, and a flat head support 322 that is secured to neck support 320 and held substantially parallel to back support 318. Head support 322 mates with a series of ratchets or support grooves 324 on neck support 320 so that the position of head support 322 can be adjusted along neck support 320 while maintaining the substantially parallel relationship between head support 322 and back support 318.

In use, the subject 302 can be placed supine on stretcher 304 with back support 318 under the back of the subject, the neck positioned in cut-out portion 311, and head 316 tilted back over the top edge of stretcher 304 with head 316 in reservoir 308, which also serves as the receptacle for holding the head. The position of head support 322 is adjusted to support the crown of head 316 at a desired depth within reservoir 308. Reservoir 308 contains cool liquid 326 up to a level that covers the crown of head 316 to provide external cooling of the head (or below the head if scalp cooling is not desired). As described in connection with other embodiments, irrigation catheters (not shown) are inserted in the subject 302 and cooling liquid 326 is pumped from reservoir 308 into the aerodigestive tract of the subject to achieve the desired rate and degree of cooling. Since both the reservoir and stretcher are on wheels, they are transported in tandem to administer the hypothermia therapy to the subject during transport.

Additional details about the disclosed methods, systems, and device are provided in the following sections.

Temperature of the Liquid

Since permanent brain injury is a major cause of death and disability, more effective methods of brain cooling will benefit a subject's overall medical recovery even if these treatments risk transient damage to other tissue beds. While frostbite can sometimes occur at temperatures less than 0° C., perfluorocarbon (PFC) and other liquids at temperatures used herein are believed to be more beneficial than harmful in this method. For example, household freezers maintain their contents at −17° C. and food (such as ice cream) is consumed at this temperature without damage to the mouth or esophagus. Likewise, cold items from a freezer can be placed on damaged skin to reduce swelling (ice packs to traumatized areas) without unacceptable risk of tissue necrosis.

The esophagus and upper airway are resilient to a variety of damaging stimuli, such as acid reflux, toxic injections, radiation, and chemotherapy. The lungs, upper airways, and skin have been exposed to 0-4° C. water/saline in cold water drowning without significant sequela. A lung has been infused with sufficiently large volumes of 4° C. PFC without significant adverse effects, so cold biocompatible liquids that may inadvertently enter the lungs is unlikely to be harmful.

Beneficial results of brain cooling can be seen, for example, with cerebral cooling to approximately 33° C. However, the brain can tolerate much lower temperatures. Animals have had their brains cooled to 10-26° C. and subsequently recovered without significant neurological damage. Humans have been found at 26° C. and subsequently recovered without significant neurological damage. Based on this information, it is believed that the disclosed hypothermic treatment can be used with an acceptable therapeutic risk if the cooled liquid is at any temperature below about 30 or 32° C., and above −20° C., for example, above −10° C., zero ° C., 10° C., or 20° C. Brief skin and upper airway exposures to liquid with temperature between −30 to −20° C. may also carry an acceptable risk of soft tissue injury. Therapeutic risks of cold damage to soft tissue can also be reduced by inducing the hypothermic cooling at a lower temperature and then gradually increasing the temperature as the risk of soft tissue damage increases and the risk of permanent brain damage decreases.

Precooling the Brain

The disclosed brain cooling method has been described in connection with the treatment of cardiac arrest, stroke, brain injury, and other conditions. However, the method can also be used prophylactically, for example, to prepare a patient for cardiovascular surgery in which the patient is placed on a heart-lung bypass machine. Prior studies have shown good outcomes of cardiac surgery performed on humans externally cooled to 25° C. with ice baths. Such patients have had encouraging outcomes after circulatory arrest that lasted for 30 to 77 minutes that was not supported by heart-lung bypass or other means. Adverse neurological outcomes were observed only in 3.8% of surviving patients, predominantly in those with arrest times longer than 30 min. The brain cooling methods described herein can be substituted for the external cooling with ice baths during such procedures.

While "suspending" cerebral metabolism may explain some of the protective effect of hypothermia, the temperature of the brain at the time that cerebral blood flow is restored may also be an important variable. This hypothesis is consistent with reperfusion-injury theory. Neurological function may be better in patients who have perfusion reinstated after cerebral cooling rather than before cerebral cooling.

Clinical Indications

A variety of clinical conditions can be treated with the methods, systems, and devices disclosed herein. In some embodiments, the method involves determining whether a subject has a condition that would benefit from treatment with the cooling method and then treating the subject with the method once it has been determined that the subject has that condition. In addition, the method includes determining whether the condition would benefit from relatively selective cooling of the brain or non-selective cooling, then administering that type of cooling (or a combination thereof). Examples of such conditions, and a treatment that can be initiated in response to finding that condition, are shown in the following Table 1.

TABLE 1

Clinical Indications for Cooling, and Types of Cooling

Selective cooling (targets cooling primarily the head and brain)
    Anoxic encephalopathy
        Cardiac arrest
        Hemorrhagic shock
        Sepsis
    Neonatal anoxic encephalopathy
    Stroke
        Embolic
        Hemorrhagic
    Head trauma
        Closed
        Open
    Neurosurgery
        Cerebral aneurism repair
        Hematoma evacuation
        Resection of abnormal tissue or tumor
    Cardiovascular surgery
        CABG (Coronary Arterial Bypass Surgery)
        Valve surgery
        CEA (Carotid Endarterectomy)
        Aortic aneurism repair
        Pulmonary arterial embolectomy
    High risk general surgery
    Procedures with risk of diminished oxygen or blood flow to brain from Hypoxia
        Hypotension
        Systemic or cerebral embolization
        SIRS (systemic inflammatory response syndrome)
    Status epilepticus
    Fever associated with:
        Systemic infection
        Stroke
        Seizures
        Malignant hyperthermia
        Neuroleptic syndrome
    Encephalitis
        Infectious
        Toxic
        Metabolic
    Meningitis
    Prevention of hospital acquired pneumonia
Non-selective cooling (also targets cooling organs outside of the head)
    Early stage of brain cooling TABLE 1-continued Clinical Indications for Cooling, and Types of Cooling Spinal cord
    Injury
    Ischemia
Myocardial infarction
Cardiogenic shock
SIRS (systemic inflammatory response syndrome)
    Septic shock
    Hemorrhagic shock, large volume transfusion
    Anaphylactic shock
Acute lung injury
    ARDS (adult respiratory distress syndrome)
    Aspiration
    Pneumonia
    TRALI (transfusion related acute lung injury)

Treating Stroke:

Many animal studies have shown that cerebral cooling results in improved neurological function and reduced volume of infarct after stroke. Cerebral cooling appears to be beneficial even if initiated hours following the onset of the stroke; however, more benefit is obtained if therapeutically effective hypothermia is promptly induced and maintained in accordance with the methods disclosed herein. Cerebral cooling can be used as a primary therapy for stroke, and can also be used as a bridging therapy before attempting cerebral revascularization.

Cerebral revascularization is performed as a standard treatment for embolic strokes. Thrombolytics are routinely used to treat embolic stroke in patients who present to a medical center within 3 hours of initial symptoms. The mechanical removal of cerebral vascular embolism (embolectomy) has been shown to improve neurological function in humans after stroke even if revascularization is delayed until up to 8 hours after the onset of the stroke. Timely revascularization is also combined with the disclosed methods of rapid induction of cerebral cooling to significantly improve neurological outcome after stroke.

Fevers:

High fevers are commonly seen in infection, stroke, seizures, trauma, and adverse drug reactions. Fevers are associated with significantly worse neurological outcomes. Current methods of cooling are often not able to prevent or blunt fevers even when patients are closely monitored in intensive care settings. Fevers often present rapidly (spike) and often last for only 1-2 hours, and current methods of cooling are not able to lower temperatures significantly in this short amount of time, even when the brain is normothermic and would be expected to take even longer to cool the brain during fever. The methods disclosed herein are capable of reducing cerebral temperatures to <33° C. in 5-15 minutes even in the face of fever to rapidly blunt fevers and reduce damage to vulnerable organs such as the brain, lungs, and kidneys. Rapid interruption of fever spikes is also believed to improve outcomes in systemic inflammatory conditions, such as septic shock and acute lung injury.

Surgical Procedures:

Brain damage is also a risk associated with neurosurgical, cardiovascular, and other surgical procedures. Cognitive and behavioral changes are common after CABG (coronary arterial bypass surgery). Episodic hypotension and hypoxia are common occurrences in such high risk surgical procedures. Surgical interruption of cerebral blood flow is also required for cerebral aneurysm repair and CEA (carotid endarterectomy), which can induce transient or permanent neurological damage. Cerebral hypothermia is believed to reduce the effects of surgically-related brain damage from intraoperative hypotension, hypoxia, interruption of cerebral blood flow (emboli, vascular clamping), or inflammation. Brain cooling before injury results in better outcomes than if cooling is initiated after injury; therefore, to prevent or minimize surgery-related brain injury, cooling is preferably completed before the initiation of surgery, for example, between the induction of anesthesia and the beginning of surgery. Cooling can be maintained during surgery and the recovery period.

Myocardial Infarction and Ischemia:

The disclosed rapid induction of therapeutic hypothermia is also believed to be advantageous in subjects who have had a myocardial infarction (MI) whether or not blood flow is reestablished to the affected area. If perfusion is not reestablished, cooling is believed to limit the volume of dead tissue by salvaging the areas with collateral circulation and partial perfusion. Cooling the heart and systemic arterial blood before perfusion is reestablished is believed to decrease reperfusion injury, which may be the primary cause of permanent myocardial damage after MI. In some embodiments of the method, cooling is therefore initiated before revascularization and is continued during and after coronary instrumentation or thrombolysis. Rapidly induced hypothermia cools the heart in a clinically desirable amount of time while reperfusion efforts are underway. Rapid myocardial cooling occurs because cooled blood occupies all four chambers of the heart, cooled systemic arterial blood supplies the myocardium, and the outer surfaces of the heart are directly cooled by the cold liquid in the esophagus and/or the stomach.

The disclosed cooling methods are safe for use during treatment for acute MI. Cardiac arrythmias are common after MI, and systemic hypothermia increases the risk. It is therefore possible that electrical cardioversion will be required to offset such heart rhythm abnormalities; however, cardioversion can be performed safely since the chest and torso will be dry, and the device is electrically isolated.

Cooling of the Spinal Cord or Body to Diminish Inflammation:

The disclosed method can also be used for non-specific cooling of organs other than the brain. For example, irrigating the oropharyngeal cavities and esophagus with cool water can be used to cool the entire neck or back and adjacent structures, such as the spine and spinal cord (such as the cervical spine) in a trauma victim with a neck or back injury. Such cooling will diminish residual adverse neurological sequelae. Although the spinal cord is thinner than the brain, it is surrounded by more insulating tissue and bone. These insulating features can be overcome, however, by cooling the blood that is perfusing the spinal cord and its surrounding structures. The regioselective features of the disclosed method can be used to enhance treatment of particular types of injuries, or maximize the cooling of specifically affected areas.

Generalized cooling of the spinal cord can be achieved by rapid and significant cooling of the brain, which lowers the temperature of the cerebrospinal fluid (CSF) that circulates around the spinal cord. The introduction of cool liquid through the tubes in the mouth and esophagus will introduce a high rate of heat convective transfer as flow contacts tissues that are very near the brainstem, which can also be helpful in cases of basilar stroke or other injuries to the brainstem. In addition, the cooling of blood returning from the head (for example, via the jugular veins) in turn cools the blood in the heart that is subsequently pumped through the aorta and to the vertebral arteries that perfuse the spinal cord. Cooling of the mediastinum by introducing cool liquid into the esophagus and the stomach will cool the blood returning to the heart via the superior and inferior vena cava. This cooled blood will then be pumped to the spinal cord. The overall reduction in body temperature achieved by lowering the temperature of aortic blood also helps reduce the inflammatory response and minimize permanent neurological damage that may otherwise occur to neuron bodies from damage to its neurons.

Although regioselective cooling of the upper aerodigestive tract will target cooling directly to the cervical spine, more generalized cooling can be used to minimize systemic inflammatory effects of trauma to the brain or non-brain structures (such as spinal cord injury or other types of trauma, such as multiple fractures). Complete submersion of the head accompanied by cooling irrigation of the entire aerodigestive tract (but not the lungs) will maximize total body cooling and accelerate induction of protective cooling to minimize the inflammatory response. For example, placement of irrigation tubes into the nasopharynx, oropharynx, and esophagus (and optionally the stomach) will rapidly induce widespread body cooling.

In cases of potential spinal injury, care must of course be taken to stabilize the spine during the induction of rapid brain and/or body cooling. Devices and methods that avoid extension of the neck are preferred in such circumstances.

The disclosed methods cool the spinal cord at all levels relatively rapidly because the cord is thin and of low mass. Cooling of the upper cord is enhanced because it is bathed with cold cerebrospinal fluid (CSF) from the cranium and direct cooling from the upper airway. Cervical spine cooling is targeted for 33° C. within 15-30 or 15-20 minutes of initiating cooling.

Lung Cooling:

Inflammation associated with lung injury, such as the adult respiratory distress syndrome (ARDS) has been extremely difficult to prevent and treat. Broad anti-inflammatory modulation with steroids has had mixed results and is not recommended for early-stage ARDS. The only targeted anti-inflammatory therapy for sepsis that has come to market is so toxic that it is contraindicated in patient with isolated ARDS and no other organ failure; the morbidity and mortality associated with the drug is greater than that of ARDS alone. In contrast, systemic hypothermia causes less toxicity while demonstrating broad anti-inflammatory properties. Prior studies have shown that cooling in ARDS provides a 33% reduction in predicted mortality when body temperature is reduced to 33° C. in severe ARDS otherwise refractory to non-cooling treatments.

The lungs cool more quickly than most other organs (including the brain) when the non-selective cooling methods disclosed herein are used. The lungs have the greatest ratio of blood flow to organ mass in the body, and the full cardiac output runs through them. The lungs are also insulated by air in the airspaces, which compose the majority of the lung's volume, and have a low metabolic rate.

Avoiding Hospital Acquired Pneumonia:

Hospital acquired pneumonia, particularly for a patient receiving mechanical ventilation, is caused by translocation of bacteria from the upper airway to the lung. Currently, prevention of ventilator associated pneumonia relies on attempts to disinfect the upper airway using an antibacterial mouth wash applied twice daily in combination with frequent oral care. However, the disclosed cooling is believed to lower the incidence of ventilator associated pneumonia by reducing the number of viable bacteria in the upper airway by washing away bacteria with the large volume of cooling liquid that passes through the upper airway. The temperature of the cooling liquid renders the bacteria inert and can even kill many species. In addition, cooling liquid that contains propylene glycol further reduces the number of viable bacteria because propylene glycol has broad antibacterial properties.

Inhibiting Flow of Cool Liquid into Lungs

Maintaining the lungs free of the cooling liquid avoids loss of the liquid from the upper airway and helps maintain more effective gas transport in the lungs. A variety of techniques are disclosed as means for inhibiting the entry of the cool liquid into the lungs.

For example, the subject's head and neck may be extended unless contraindicated (for example, when cervical spine damage is suspected). Head and neck extension reduces the risk of cold liquid entering the lung by elevating the level of the entrance of the trachea (the larynx) compared to the level of the liquid.

Alternatively, the subject is placed in the Trendelenburg position with the head lower than the chest. This position reduces the risk of cold fluid entering the lung by elevating the level of the entire trachea and lungs compared to the level of the liquid.

Another possibility is to elevate the subject's chest on a firm (possibly padded) board approximately 10 to 30 cm thick. The chest elevation raises the level of the entire trachea and lungs compared to the level of the liquid. In some embodiments, the board will have a defect in the midline of the cephalad portion to allow the neck to hyperextend without impingement on the board. The board may also extend under the head at a thickness of 2 to 6 cm, positioned under the box to support the box. The board can be firm enough to support CPR.

As shown in the detailed embodiments of the method, a multi-lumen endotracheal tube with an inflatable balloon cuff (or for infants potentially without a cuff) may also function to keep cold liquid from entering the lungs. The endotracheal tube may also contain a third lumen with the distal opening immediately proximal (above) the inflatable balloon cuff and with the proximal end connected to suction. This third lumen can assist in removing liquid proximal to the balloon cuff, reducing the amount of liquid that would need to be blocked by the balloon cuff.

Liquid Flow and Temperature

The total amount of liquid introduced into the cool liquid reservoir (if one is used) can be varied according to the needs of the patient. As already noted, the cool liquid can be introduced at a depth that covers the entire head and face. Another option is to keep the liquid level below the level of the endotracheal balloon. The pump flow (from one or more pumps) can be adjusted to provide overall liquid flow in the range of 0.2 to 10 or L/minute to the internal catheters (not including the catheters provided for directing a flow of cooling liquid against the scalp of other structure that does not involve insertion of a catheter into the mouth or nose). In certain examples, this flow is at least 10 L/min, and in particular examples, a total flow of about or up to 20 or 30 L/min. The total flow is typically delivered through 1-6 (such as 2-6) or more catheters. The position of inflow and outflow catheters can be changed over time if needed to provide or maintain liquid flow over the scalp and in the upper airway.

In certain embodiments, flow can be adjusted to be 0.2-10 L/min into the upper airway and 1-20 L/min on the scalp for adults, less for children and infants. A particular reservoir (such as a box in which the head is partially or totally immersed) has a total volume of about 40 liters if the box is about 35 cm on all sides. In such particular embodiments, 1 to 15 or 20 total liters of cold fluid are present in the reservoir, for example, about 10 liters. The contents of the reservoir can be circulated about twice a minute, or more, to achieve a desired degree of convection that enhances head cooling. To maintain very high flow cooling at a low temperature, even larger reservoirs of cooled liquid can be employed, such as reservoirs that contain 20 or more liters (for example, at least 30 or 40 liters) of the cooling liquid at the desired temperature (for example, less than 5° C., 0° C., –5° C., or less).

To achieve optimal cooling, different flow rates of cooling liquid can be introduced through different catheters that are used in the method.

The temperature of the liquid in the container can be adjusted by various cooling means over time when a container is used. Similarly to flow rate, different cooling fluid temperatures can be introduced through different catheters. For example, any one or combination of the following methods may be used to adjust temperature:

- adding cold liquid to the reservoir to increase the volume of liquid in the box
- removing an aliquot of warmer liquid and replacing it with colder liquid
- placing inert cold objects within the reservoir
- placing frozen water (water ice) or CO2 (dry ice) within the reservoir (as used herein, "ice" refers generically to a solid phase of a non-metallic substance that is a liquid or gas at room temperature)
- placing a heat exchanger in series with the reservoir and the pump Additional air may be added to the balloons of the endotracheal tube and the esophageal catheter to compensate for volume loss in the balloon as the air within the balloon is cooled.

The initial temperature of the liquid is in the range of –30 to +30° C. Optimal temperature may vary during treatment but is believed to be in the range of –20 to +10° C.

The ideal cooling liquid is biologically compatible (for example nontoxic) and has a melting point in the range of –50 to +10° C. and a boiling point of greater than 50° C. Examples of liquids meeting these are listed in Example 12. Liquids can be combined or used in series during the treatment.

Multistage Cooling (Induction and Maintenance)

The cooling methods disclosed herein can be used for multi-stage treatments, for example using induction and maintenance regimens. In certain examples, the induction stage can take 15 minutes to an hour, followed by a maintenance phase that can last greater than 12 hours, for example, 12-48 hours, such as up to a week or more. It may be desirable to use different liquids and temperatures in the induction and maintenance phases of the treatment. For example, lower liquid temperatures will be used in the induction phase to achieve more rapid cooling, while higher liquid temperatures can be used in the maintenance phase. In one example, the temperature of the cooling liquid during the induction phase is –30 to 5° C., while the liquid temperature in the maintenance phase is 5 to 30° C. Liquid flow rates are also varied depending on the stage of treatment In one example, a liquid temperature below 0° C. is used for the induction phase to achieve more rapid cooling (for example during the first 30 minutes to one hour of cooling). Temperatures below 0° C. are achievable with liquids such as propylene glycol cooled with ice. After cooling induction, higher temperatures (above 0° C.) are used for maintenance. Such temperatures are readily achieved with cooled water.

Given the urgency of cooling the subject quickly to achieve maximal benefit from the procedure, less controlled conditions may be used during rapid induction, for example in the field (such as in an ambulance) before a subject is brought to a hospital. Hence the subject's head may be partially or completely immersed in a container of ice water by emergency medical technicians who have been sent to retrieve a patient who may benefit from the treatment. The liquid in the container can also be used to supply the irrigation fluid for the aerodigestive tract at a less controlled temperature than would be achieved in the more controlled in-patient setting (as in an intensive care unit).

Different body regions can also be cooled in different stages of the treatment. Portions of the head and aerodigestive tract that are suitable for irrigation with forced flow of cold liquid include external structures such as the scalp and face, and internal structures of the aerodigestive tract such as the naso-pharynx (through nose tubes), the oro-hypopharynx (through a mouth tube), the esophagus (through one or more esophageal tubes), and the stomach (through a stomach tube). During induction, when rapid cooling of the brain and/or body is desired, all regions may be used for cooling unless otherwise contraindicated. Alternatively, during induction catheters can be placed in all these locations except the stomach. During maintenance treatment, any combination of the external and internal structures can be used to achieve desired degrees of targeted or non-targeted cooling.

Selective and Non-Selective Cooling

The disclosed method and device can be used to preferentially or selectively cool the brain ("selective mode") or to cool the entire body ("non-selective mode").

In the selective mode, the aerodigestive regions to be cooled by applying cooling liquid are only the nasopharynx and oropharynx; in some embodiments the cooling liquid is also introduced into the upper esophagus. Liquid may optionally be inhibited from entering the lower esophagus and the stomach by placing an esophageal balloon that obstructs the lower esophagus. However, in some embodiments of selective cooling the esophagus is not mechanically obstructed.

In non-selective mode, the following regions are cooled: scalp, face, nasopharynx, oropharynx, and portions of the gastrointestinal tract, such as one or more or all of the upper esophagus, lower esophagus, and stomach.

Selective cooling allows for lower temperatures in the brain with less cooling of the body core and therefore less systemic toxicity. In animal models, brain temperatures of 15° C. have been shown to be very well tolerated and therapeutic, while core body temperatures of <30° C. are associated with increased risk of cardiac arrythmia, pneumonia and electrolyte shifts. However, even very deep cooling to temperatures as low as 25° C., or even 20° C., does not appear to have adverse effects in the brain. Benefits of cooling are likely a non-linear function of cooling depth because cooling decreases the metabolic rate of the cells, which in turn decreases both oxygen demand and heat production in the tissue, as well as reducing swelling and the rates of the other biochemical reactions associated with re-perfusion injury.

Non-selective cooling is used to reduce the effects of inflammation and ischemia throughout the body. Many diseases or conditions are driven by inflammation: reperfusion injury after organ ischemia, septic shock, trauma and allergic reactions. Cooling has a potent broad non-selective anti-inflammatory effect and is currently being studied as a treatment for some of these conditions.

Cooling outside of the cranium is accomplished by cooling the arterial blood supplying the organs or structures of interest, or the body in general. Experimental data from use of the disclosed device and method have demonstrated significant cooling of the aortic blood, at approximately the same rate and depth as that of the brain, even without cooling the lower esophagus or stomach. Arterial blood temperature (measured in the aorta) is decreased by profoundly cooling the blood returning to the heart from the head and neck. Cooling of the face and scalp cools the blood delivered to the extracranial structures of the head via the external carotid artery. In addition, cooling of the tissue surrounding the upper aerodigestive tract (above the esophagus) also cools the returning jugular venous blood. Cooling of every possible surface of the head and the entire upper airway provides effective non-selective cooling.

Cooling structures below the upper aerodigestive tract, such as the lower esophagus and stomach, increases the rate of systemic arterial blood cooling. Cooling of the entire mediastinum can be achieved by cooling the full length of the esophagus as well as the stomach. The proximity of the esophagus to the superior vena cava, right atrium and inferior vena cava allows for cooling of blood coming from all areas of the body. Therefore, cooling of the entire esophagus and the stomach allows for more rapid cooling of systemic arterial blood by cooling all venous blood as it returns to the heart.

Although some currently available hypothermia devices rely on non-selective cooling, they are unable to provide non-selective cooling at therapeutically beneficial rates. The methods and devices disclosed herein are optimally able to achieve a therapeutic target temperature in the brain within 5-10 minutes, but optimal cooling of most of the non-brain organs is expected to require more time. The rate and depth of cooling of an organ will depend on multiple factors, including the organ's mass, metabolic activity, rate of blood flow and cold induced vasoconstriction in addition to the temperature of the blood perfusing the organ. This amount of time is still much less than that required by state-of-the-art devices, which require 3-6 hours.

The methods and devices disclosed herein are also capable of delivering a rapid "burst" of hypothermia to affected organs (such as the brain) early in the course of treatment. Rapid induction of hypothermia allows for a more definitive reduction of inflammation at the beginning of the inflammatory cascade, which is believed to significantly enhance the effectiveness of treatment. Early temperatures in target organs could briefly be obtained that are far lower than what would be considered toxic if maintained throughout the body for a prolonged period of time. Such rapid cooling can comprise the introduction of cooling fluid for short durations at pre-determined temperatures to achieve desired treatment effects in much shorter periods of time (e.g., 6 hours, 5 hours, 4 hours, 3 hours, 2 hours, 1 hour, or less) than traditional devices.

Any "overshoot" of systemic cooling can be rapidly corrected. Since continuation of cooling requires continued use of the device, merely discontinuing or diminishing treatment will result in an increase in body temperature. This rapid reversibility contrasts to other state-of-the-art devices which require warming of the entire mass of the body if the core body temperature decreases to an unwanted level. Warming the entire mass of the body is a slow process. If still more rapid warming were desired, external warming could be applied.

In certain embodiments of the method, therapeutic hypothermia (e.g., to a core temperature range of approximately 33° C. or less) is induced non-selectively followed by selective cooling (for example, of the brain to result in very rapid cooling of the brain). Delivery of warm blood from the body via the carotid and vertebral arteries normally counteracts cerebral cooling. However non-selective cooling results in a rapid decrease in systemic arterial blood temperature, resulting in cooler blood entering the carotid and vertebral circulations in the upper chest and allowing for an even lower temperature of blood as it enters the brain. Non-selective cooling also decreases the minimum plateau temperature achieved in the brain. The minimum temperature of the brain is a balance between the amount of heat delivered to the head from the body and the amount of cold delivered by the device. Since non-selective cooling decreases systemic arterial blood temperature, less heat is delivered to the head and lower brain temperatures are possible, and are more rapidly achieved.

After the brain has reached its goal temperature (directly measured or predicted by non-invasive measurements) cooling can be switched from non-selective cooling to selective head cooling. This change helps avoid adverse reactions from body core hypothermia. After selective cooling is initiated, body warming can be initiated to slow or reverse the temperature decline for the body core. Warming can also be applied to the body core to hold the body at one temperature while cooling is used to drive the brain to a lower temperature.

Emergency Cooling with Rapid Induction

An advantage of the disclosed methods and devices is that they are capable of inducing rapid cooling of the brain and/or other organs and/or the entire body. Such rapid cooling has been found particularly beneficial in the avoidance of permanent tissue damage and the promotion of full functional recovery. Certain disclosed embodiments can therefore be useful in connection with emergency medical technicians (EMTs) in the field, for example, for use by EMTs in ambulances transporting patients to a hospital.

A cooling unit (such as a small freezer) may be placed in an ambulance, and the unit contains 5-50 liters of a cooling liquid (such as 20% propylene glycol in water). If the technicians find a subject who has a condition that would benefit from brain and or body cooling (as detailed in other sections of this specification), then rapid field-induction of brain or body cooling can be achieved by quickly immersing the head of the patient in cooling liquid. To simplify use of the device in the field, ice cubes can be placed in the liquid to maintain it at the desired temperature. The iced liquid in which the head is submerged also serves as a reservoir of cooling liquid that can be directed in a flow externally against the head, and/or used as an irrigating fluid for introduction into the aerodigestive tract. This simple version of the device will not require any electrical cooling devices, and cooling can be maintained by ice cooled liquid alone for the duration of transportation of the patient to the hospital.

When used in the field, and to simplify the technique for rapid induction and ease of transportation, the cooling of the aerodigestive tract may be carried out without external application of cooling liquid to the head, as would occur in partial or total immersion of the head. However, the cooling liquid may optionally be applied externally to the head to further accelerate rapidity of therapeutic hypothermic induction.

Pump Embodiments

Multiple pumps can be incorporated into the system. For example, a first pump can draw liquid 118 from the reservoir in container 112 through a first inlet conduit to the first pump and pump the liquid back through a first return conduit into container 112 externally over the head. A second pump can draw liquid from the same reservoir through a second inlet conduit to a second pump and pump the liquid back through a second return conduit to the upper airway catheters. An advantage of the separate pumps is that the flow of liquid can be separately regulated if external delivery around the head is desired and for internal delivery into the upper airway. This is a particular advantage when the caliber of the upper airway catheters is different than the conduit for external delivery of the liquid, and the internal resistance of the external and internal delivery systems differs.

In other embodiments of the method that use multiple catheters, each catheter can be associated with a separate pump. Alternatively, a separate pump can provide liquid flow to all catheters in particular anatomic regions, such as all the external catheters, all the internal catheters, all the catheters in the upper airway, all the catheters in the gastrointestinal tract (esophagus and/or stomach), etc.

Various types of pumps can be used with the present invention, such as, for example, peristaltic pumps (e.g., to permit pumping fluid without contacting the fluid), diaphragm pumps (e.g., with disposable heads), and/or gear pumps (e.g., with disposable heads).

The pump or pumps may be either manually operated or non-manually powered, for example by electricity. A hand or foot powered pump can be used for field operation outside a hospital or ambulance where a source of electricity may not be readily available. Once the patient is transported to an ambulance or hospital, the pump can be connected to a source of electrical energy and automated pumping initiated and continued for a sustained period of time.

Batteries can also be used to power the pump for field operation.

Esophageal Tubes

A variety of specialized single or multi-lumen esophageal tubes can be provided to deliver the high flow of cooling liquid to the aerodigestive tract in those embodiments that employ esophageal irrigation. For example, a single, double, triple, and/or quadruple lumen catheter may be employed.

With a triple-lumen catheter, the inner lumen, for example, can be the longest and can provide stomach access. In some instances, the lumen acts as a nasogastric tube hooked up to suction, for example, to remove cooling and other liquids from the stomach if desired. Alternatively, the long inner lumen can be used to deliver cooling liquid to the stomach. The middle lumen can, for example, deliver cooling liquid and can have multiple side ports for omni-directional delivery of the cooling liquids in multiple different directions and at different levels of the esophagus. In other embodiments, the middle lumen can be configured to permit air and/or liquid to pass to an inflatable member (e.g., a cuff) to permit inflation of the member. The outer lumen can selectively remove cooling liquid from the esophagus if desired (e.g., via a negative pressure device in fluid communication with the outer lumen). In other embodiments, similarly to the middle lumen described above, the outer lumen can be configured to permit air and/or liquid to pass to an inflatable member (e.g., a cuff) to permit inflation of the member. However, flow of returning liquid moving along the wall of the esophagus toward the mouth is helpful in achieving heat transfer to the liquid, hence suctioning of return liquid is not normally used absent special circumstances.

Alternatively, multiple parallel tubes of different lengths can be used to introduce flow into the esophagus. The longest tube can be positioned with its tip in (or near) the stomach and can serve to introduce cooling liquid to the stomach, suction cooling liquid from the stomach, and/or provide pressure relief from the stomach. This tube can have an inflatable balloon around the tube (e.g., about 10 cm from the distal end of the tube). The balloon can selectively be inflated in the lower esophagus if it is desired to isolate the stomach from the flow of liquid in the esophagus so that the cooling liquid is directed more selectively to the esophagus. The mid-length tube can be of a sufficient length to be positioned with its tip near the inflatable balloon (e.g., about 3 cm from the balloon on the first tube). In some embodiments, the mid-length tube can comprise one or more side ports for the delivery of the cooling liquid and/or suction of cooling liquid (e.g., depending on the embodiment). The short tube can be positioned with its tip in the hypopharynx, and, similarly to the mid-length tube, can have one or more side ports along its length for delivery and/or removal of cooling liquid in the hypopharynx. Endotracheal catheters can comprise similar features to the esophageal catheters described above while being configured to be disposed in a patient's trachea.

Mouth and/or Nose Drainage

An advantage of certain embodiments of the device and method is that the cooling liquid is capable of draining passively through the mouth and/or nose without application of suction. Removal of liquid through the mouth and/or nose avoids removal through suction tubes placed in the aerodigestive tract, and therefore provides flow of the cool return liquid over the large surface area of the tissues of the aerodigestive tract to maximize heat exchange between the tissues and the liquid. Drainage of the liquid through the mouth and/or nose can be achieved with the head entirely submerged in the cooling liquid, partially submerged in it, or not submerged at all.

In some illustrated embodiments, liquid that drains out of the mouth collects in a reservoir around the head. However, the draining liquid can also collect in a reservoir that is below or beside the head. For example, the head may be supported by a permeable support surface having an opening or openings through which liquid returns to the reservoir. The draining liquid can then be cooled and returned to the aerodigestive tract for continued cooling of the tissues.

In one example, the head may be turned to the side so that liquid will pour out one side of mouth, which will help avoid contacting the cool liquid with the face and help keep liquid out of the lungs by lowering the level of liquid in the upper airway. The head can be gently restrained to keep the head turned to its side, and the corner of the mouth may be pulled down to encourage egress of liquid from the mouth. In some embodiments a drainage tube can be place in the mouth to further reduce the level of liquid in the mouth. Or the liquid can be primarily withdrawn by suction (e.g., via a negative pressure device through one or more endotracheal and/or esophageal tubes), in this case the open mouth and nose serve as a "safety outlet" preventing any increase in pressure.

Cooling Liquids

A variety of biologically compatible cooling liquids can be used, either alone or in combination, in the disclosed methods and devices. A biologically compatible liquid is one that is either non-toxic, or that has levels of toxicity that are acceptable in view of the problem being treated. Some toxicities are minor (such as skin irritation that can be caused by glycerol), and others are more significant (such as causing electrolyte abnormalities) but can be medically managed. As long as the toxicity presented by use of the liquid is acceptable in the clinical circumstances in which it is used, the liquid is considered biologically compatible. Any liquid that causes a severe permanent injury or is incompatible with life is not considered biologically compatible. Liquids that may not be biologically compatible at high concentrations can in some instances be made biologically compatible by adding a diluent (such as water).

Examples of biologically compatible liquids are listed in Table 2.

Cooling liquids particularly useful in the methods disclosed herein have high heat capacity and thermal conductivity. Gases are not suitable for this purpose because they do not transfer heat at the rate envisioned by the disclosed methods. The optimal temperature for a particular liquid is often the lowest temperature that can be achieved without freezing, and with an acceptable degree of viscosity.

Colder cooling liquids increase the rate of brain and/or body cooling, however the rate of cooling is balanced with the potential tissue damaging effect of the cold liquid. However, animal (including human) tissue can tolerate surprisingly low temperatures, at least for limited periods of time. Items from food freezers (−17° C.) are routinely placed on skin after trauma to reduce swelling, which illustrates the ability of skin to tolerate such low temperatures. The mucous membranes (such as those found in the aerodigestive tract) also tolerate low temperatures, as illustrated by the fact that items from food freezers (−17° C.) are routinely eaten.

Mixtures of liquids are particularly contemplated as useful in the disclosed methods. For example, mixtures that take advantage of interactions with water can be used. A water/propylene glycol mixture is a preferred liquid for induction because it can be cooled to temperatures below 0° C. A water/saline cooling liquid will likely be used as maintenance liquid to maintain a temperature above 0° C. for 12-48 hours because of its low toxicity. Saline solution has a lowered freezing point, and is easily washed off the patient, staff and equipment.

Examples of cooling liquids include those shown in Table 2.

TABLE 2

Cooling Liquids

Water-based
    Propylene glycol (5-25% in water)
    Ethanol (5-25% in water)
    Glycerol/glycerine (5-25% in water)
    Dextrose (5-25% in water)
    Sodium chloride (1 to 5% in water)
    Calcium chloride (1-25% in water)
Oils
    High-oleic safflower oil
    Corn oil
    Castor oil
Perfluorocarbons
    Perfluorohexane
    Perfluoroheptane
    Perfluorooctane
Additives (optional)
    Detergents (trace)

Trace quantities of detergents such as sodium laurel sulfate, sodium laureth sulfate, etc can be added to the cooling liquid to solubilize debris and bodily fluids (blood, mucus, hair, sweat) and inhibit pump/tubing obstructions.

As mentioned above, a particularly preferred cooling liquid for the induction phase is propylene glycol (PG) and mixtures of PG in water. The PG is cooled to −10 to −20° C., and is used during induction for 30-60 minutes. This temperature is achievable because PG 40% in water has freezing point of −22° C. PG is in an FDA classification of "generally recognized as safe" and has very low ingestion toxicity. For example, PG is found in high concentrations in foods and cosmetics; the average adult in the United States consumes 2.5 grams/day of PG in food. PG is a common ingredient in mouthwash, and is the main ingredient in many oral and intravenous medications. It causes minimal skin and eye irritation, and is used in many topical medications and personal care products. PG has been nebulized and inhaled for treatment of chronic lung disease. It is easily flushed off mucous membranes and skin by water or saline, so this induction liquid can easily be removed by flushing with saline, water of other liquid that is used in a subsequent maintenance phase of treatment.

Other characteristics of PG that make it very suitable as a cooling liquid are its high specific heat (which is close to water and better than ethylene glycol), a viscosity only slightly higher than water, a surface tension lower than water (when mixed with water), compatibility with many types of flexible tubing and pumps, very low flammability, and no special disposal needs.

A particularly suitable cooling liquid for maintenance of hypothermia is saline solution, such as 0.9% saline solution. An optimal temperature range for maintenance liquid is +5 to +20° C., and an example of a maintenance period would be 12-48 hours. Use of saline maintenance solution for this sustained period of time is particularly suitable because it is considered a "physiologic" fluid. Saline solution during maintenance therapy also avoids dermal and enteral absorption of propylene glycol during long-term use. Saline solution can be adjusted such that it is osmotically neutral with the tissues surrounding the aerodigestive tract.

Glycerol can be a particularly useful cooling liquid component, because when added to water it has a low surface tension. Salt in water (saline solution) has no effect on viscosity and does not decrease surface tension. Sugar solution increase viscosity of the liquid, while ethanol decreases surface tension (but must be treated with caution because of its flammability). Calcium chloride slightly increases the viscosity of a solution, and it used in low concentrations because it can be an irritant at very high concentrations.

Comparative Data

Comparative studies have been performed to compare cooling induced by the method as described by Brown et al., Profound Selective Cerebral Hypothermia in Dogs by Naso-Oral Perfusion and Head Immersion, Surgical Forum 15:413-415, 1964 (Trial 1); improved cooling with liquid at 0° C. and scalp, nasal, oral and upper esophageal cooling (Trial 2); cooling liquid at −15° C. using scalp nasal and oral cooling (Trial 3).

Surgical Preparation of the Animal

A 98 kg adult female sheep was maintained under surgical plane anesthesia until euthanized. The sheep was subjected to 3 methods of cerebral hypothermia and outcome was measured by the rate and magnitude of cooling of the superficial cortex of the brain and of the systemic arterial blood. Temperatures were recorded every minute in superficial cerebral cortex, in arterial blood in the abdominal aorta, in the peri-carotid tissue of the neck, in the rectum (core temperature), and in the device reservoir. Monitoring was performed by continuous ECG, continuous pulse oxymetry, continuous arterial blood pressure, and continuous end-tidal CO2.

During surgical preparation, the sheep was intubated orally with a standard cuffed endotracheal tube (ETT) and mechanically ventilated with 100% oxygen and minute ventilation titrated to an end-tidal CO2 of 35 Torr. Tracheostomy was performed and a cuffed tube was placed with the tip in the lower trachea. Esophagostomy was performed and a cuffed tube was placed with the tip in the mid esophagus and the proximal end to gravity. Arterial and venous catheters were placed in the right groin.

The left mid neck was dissected, a temperature probe was placed lateral to the carotid artery and the site closed at the levels of the fascia and the skin. The scalp was dissected in the left upper parietal region, and a 10 mm burr hole was created through 22 mm of skull. The dura and superficial brain were incised and a temperature probe was placed with tip 7 mm below the surface of the cerebral cortex. The burr hole was sealed with dental cement. The site was closed at the levels of the fascia and the skin and covered with petroleum jelly.

Catheters were obtained for use in the following examples. The catheters had the following inner diameter (ID) and outer diameter (OD):

intake tubes—from reservoir to each of the 3 pumps
ID=½ inch
OD=¾ inch
scalp tubes
ID=½ inch
OD=¾ inch
nasal and oral and esophageal tubes
ID=5/16 inch
OD=7/16 inch Trial 1—Selective Cooling with Low Flow Cooling Liquid from Catheters Inserted Only Into Nostrils (Brown et al. Method)

One tube was placed in each nasal cavity by inserting the tip of the tube 5 cm beyond each nares.

A box open at the top acted as a reservoir for cooling liquid. The reservoir was filled with water with ice at 0° C. A pump withdrew liquid from the reservoir at 1.8 L/min, introduced it through the tubes into the nasal cavities. The liquid returned passively back to the reservoir via the nose and mouth. At the start of cooling the head was submerged in the reservoir by tilting the surgical table head-down, removing the headrest from the table and extending the neck. At the same time the nasal tubes were connected to the outflow tube of the pump. Cooling was discontinued after 30 minutes, the pump stopped, the head removed from the reservoir and the sheep rewarmed using a warm saline IV infusion and external warming of the trunk. Nasal tubes were left in place and disconnected from the pump.

Cooling was performed for 31 minutes, then rewarming was initiated. The data that was obtained is shown in Table 3.

TABLE 3

Selective Cooling with Low Flow Cooling Liquid only into Nasopharynx

| | Temperature (deg C.) | | | | |
|---|---|---|---|---|---|
| Time (min) | Brain | Peri-carotid | Aorta | Bath | Core |
| 0 | 38.1 | 37.8 | 37.7 | 1.3 | 38.1 |
| 1 | 38.1 | 37.8 | 37.6 | 1.2 | 38.1 |
| 2 | 37.8 | 37.7 | 37.1 | 1.5 | 38.1 |
| 3 | 37.4 | 37.7 | 36.8 | 1.7 | 38 |
| 4 | 37.1 | 37.7 | 36.6 | 2.1 | 37.9 |
| 5 | 36.7 | 37.4 | 36.3 | 2.2 | 37.8 |
| 6 | 36.3 | 37.4 | 36.2 | 2.5 | 37.8 |
| 7 | 35.9 | 37.1 | 35.9 | 2.5 | 37.7 |
| 8 | 35.9 | 36.8 | 35.9 | 2.7 | 37.5 |
| 9 | 35.9 | 36.8 | 35.4 | 2.8 | 37.4 |
| 10 | 35.6 | 36.5 | 35.3 | 2.9 | 37.3 |
| 11 | 35.3 | 36.4 | 35.3 | 3 | 37.2 |
| 12 | 35.3 | 36.2 | 35.3 | 3.1 | 37.1 |
| 13 | 35 | 36.2 | 35.4 | 3.2 | 37.1 |
| 14 | 35 | 35.9 | 35.4 | 3.2 | 37.1 |
| 15 | 34.8 | 35.9 | 35.3 | 3.4 | 37 |
| 16 | 34.8 | 35.9 | 35.1 | 3.4 | 36.9 |
| 17 | 34.8 | 35.7 | 35 | 3.7 | 36.8 |
| 18 | 34.6 | 35.7 | 34.5 | 3.7 | 36.8 |
| 19 | 34.3 | 35.4 | 34.5 | 3.7 | 36.6 |
| 20 | 34.3 | 35.4 | 34.7 | 3.8 | 36.5 |
| 21 | 33.9 | 35.4 | 34.7 | 3.9 | 36.5 |
| 22 | 33.9 | 35.3 | 34.6 | 4 | 36.4 |
| 23 | 33.9 | 35.3 | 34.1 | 4.2 | 36.4 |
| 24 | 33.9 | 35.1 | 34.1 | 4.2 | 36.3 |
| 25 | 33.9 | 35.1 | 34.1 | 4.4 | 36.2 |
| 26 | 33.7 | 35.1 | 34.1 | 4.5 | 36.1 |
| 27 | 33.4 | 34.9 | 34 | 4.5 | 36 |
| 28 | 33.4 | 34.9 | 34.1 | 4.7 | 35.9 |
| 29 | 33.4 | 34.7 | 34.1 | 4.8 | 35.8 |
| 30 | 33.4 | 34.7 | 34.2 | 4.8 | 35.8 |

Trial 2—Selective Brain Cooling

After rewarming the animal from the trial described in Trial 1, an oral tube was placed with the tip at the base of the tongue and an esophageal tube was placed with the tip in the upper esophagus. Two additional tubes were placed in the liquid reservoir. When the head was submerged in the reservoir their tips were 4 cm from and pointed towards the right and left parietal scalp. A box open at the top acted as a reservoir for cooling liquid. The reservoir was filled with water with ice at 0° C. At the start of cooling the head was submerged by tilting the surgical table head-down, removing the headrest from the table and extending the neck. Three pumps (1, 2, and 3) were used. The two nasal tubes were connected to the outflow tube of pump 1, oral tube to pump 2, esophageal tube to pump 2 and the two scalp tubes to pump 3. Pumps withdrew cool liquid from the reservoir at 6 L/min for pump 1, and 12 L/min each for pumps 2 and 3. Cooling was discontinued after 21 minutes, the pumps stopped, the head removed from the reservoir and the sheep rewarmed using a warm saline IV infusion and external warming of the trunk.

Data obtained from the method is shown in Table 4.

TABLE 4

Selective Brain Cooling

| | Temperature (deg C.) | | | | |
|---|---|---|---|---|---|
| Time (min) | Brain | Peri-carotid | Aorta | Bath | Core |
| 0 | 36.8 | 36.4 | 35.5 | 1.2 | 36.2 |
| 1 | 35.8 | 36.4 | 35.6 | 1.3 | 36.2 |
| 2 | | | | | |
| 3 | | | | | |
| 4 | 35.9 | 27.2 | 34.1 | 3.4 | 36 |
| 5 | 35.5 | 24 | 33.7 | 3.8 | 35.9 |
| 6 | 34.8 | 21.9 | 33.2 | 3.9 | 35.7 |
| 7 | 34.4 | 20.7 | 32.8 | 3.9 | 35.5 |
| 8 | 33.6 | 19.8 | 32.5 | 4 | 35.3 |
| 9 | 33.3 | 21.1 | 32.4 | 4.2 | 35.2 |
| 10 | 32.9 | 22 | 32.2 | 4.6 | 35 |
| 11 | 32.3 | 21.2 | 31.9 | 4.8 | 34.8 |
| 12 | 32 | 20.2 | 31.6 | 5 | 34.7 |
| 13 | 31.7 | 19.7 | 31.3 | 5.3 | 34.5 |
| 14 | 31.3 | 19.3 | 31.1 | 5.6 | 34.3 |
| 15 | 31.3 | 19.3 | 30.9 | 5.7 | 34.1 |
| 16 | 30.9 | 18.9 | 30.7 | 5.9 | 33.9 |
| 17 | | | | | |
| 18 | | | | | |
| 19 | 30.3 | 22.3 | 30.5 | 6.7 | 33.5 |
| 20 | 30 | 20.1 | 30.4 | 7.1 | 33.3 |
| 21 | 30 | 19.6 | 30.2 | 7.3 | 33.2 |

Trial 3—Propylene Glycol as Cooling Liquid (Trial 3) Continued Cooling after Animal Euthanized (Trial 4)

After rewarming the animal from Trial 2, the esophageal tube was withdrawn and replaced with a second oral tube, so that there were two oral tubes both having their tips positioned at the base of the tongue. Both nasal and both scalp tubes remained in place. A box open at the top acted as a reservoir for cooling liquid. The reservoir was filled with a 1:1 mixture of propylene glycol and water at −15° C. Pumps withdrew fluid from the reservoir at 1 L/min for pump 1, and 3 L/min for pump 2 and 5 L/min for pump 3 for a total of 9 L/min through the internally placed catheters. At the start of cooling the head was submerged by tilting the surgical table head-down, removing the headrest from the table and extending the neck. At the same time the nasal tubes were connected to the outflow tube of pump 1, oral tubes to pump 2, and the scalp tubes to pump 3. Pumps withdrew liquid from the reservoir at 1 L/min for pump 1, at 3 L/min for pump 2 and 5 L/min for pump 3 for a total of 4 L/min through the internally placed catheters and 5 L/min of liquid was directed at the scalp.

The sheep was euthanized after 14 minutes and cooling proceeded for another 22 minutes.

The results of the cooling with propylene glycol are shown in the Table 5. Measurements after death are presented in bold italics.

TABLE 5

Propylene Glycol as Cooling Liquid with Continued Cooling after Animal Death

| | Temperature (deg C.) | | | | |
|---|---|---|---|---|---|
| Time (min) | Brain | Peri-carotid | Aorta | Bath | Core |
| 0 | 34.6 | 34.7 | 33.9 | −12.9 | 34.2 |
| 1 | 34.6 | 34.7 | 33.9 | −11.6 | 34.2 |
| 2 | 34.3 | 31.7 | 33.2 | −11.1 | 34.1 |
| 3 | 33.9 | 27.6 | 32.7 | −9.3 | 34 |
| 4 | 33.4 | 25.4 | 32.4 | −7.8 | 33.8 |
| 5 | 33.1 | 24.7 | 32.1 | −5.9 | 33.6 |
| 6 | 32.6 | 25.1 | 31.8 | −3.8 | 33.4 |
| 7 | 32.2 | 22.5 | 31.3 | −2 | 33.2 |
| 8 | 31.8 | 23.1 | 31.3 | 0 | 32.9 |
| 9 | 31.8 | 22.4 | 31.1 | 0 | 32.7 |
| 10 | 31.4 | 21.9 | 31 | 0 | 32.5 |
| 11 | 31.1 | 21.6 | 31 | 1 | 32.3 |
| 12 | 31.1 | 21.6 | 30.9 | 1.4 | 32.3 |
| 13 | 30.8 | 21.4 | 30.8 | 2.3 | 32 |
| 14 | 30.8 | 21.5 | 30 | 2.8 | 31.9 |
| *15* | *30.5* | *21.5* | *31.1* | *3* | *31.9* |
| *16* | *30.5* | *20.4* | *31.2* | *2.5* | *31.9* |
| *17* | *30.5* | *19.4* | *31.2* | *3.5* | *31.9* |
| *18* | *30.2* | *18.7* | *31.3* | *3.3* | *32* |
| *19* | *30.2* | *18.1* | *31.3* | *3* | *32* |
| *20* | *30* | *17.8* | *31.4* | *3* | *32.1* |
| *21* | *30* | *17.3* | *31.4* | *3* | *32.1* |
| *22* | *29.7* | *16.9* | *31.5* | *3.4* | *32.1* |
| *23* | *29.7* | *16.5* | *31.5* | *3* | *32.2* |
| *24* | *29.4* | *16.1* | *31.6* | *3.1* | *32.2* |
| *25* | *29.4* | *15.8* | *31.6* | *3.2* | *32.2* |
| *26* | *29* | *15.4* | *31.5* | *3.5* | *32.3* |
| *28* | *28.7* | *14.8* | *31.6* | *3.8* | *32.4* |
| *32* | *28* | *14.2* | *31.8* | *4.5* | *32.5* |
| *36* | *27.1* | *13.7* | *32.1* | *5.3* | *32.6* |

Comparison of Aortic Blood Cooling using Nasal vs. Aerodigestive Cooling

Aortic blood temperature data in the following table illustrates the superior rate of systemic blood cooling achieved by introducing the higher flow of liquid into multiple sites along the aerodigestive tract and the scalp. Cooling would be accelerated even more if lower esophageal and stomach catheters were added, and cooling liquid introduced into the aerodigestive tract through them as well. Cooling liquid is also accelerated by using cooling liquid colder than 0° C.

TABLE 6

Aortic Blood Temperature

| time (min) | nasal + oral + upper esophageal + scalp | nasal + scalp |
|---|---|---|
| 0 | 35.5 | 37.7 |
| 1 | 35.6 | 37.6 |
| 2 | | 37.1 |
| 3 | | 36.8 |
| 4 | 34.1 | 36.6 |
| 5 | 33.7 | 36.3 |
| 6 | 33.2 | 36.2 |
| 7 | 32.8 | 35.9 |
| 8 | 32.5 | 35.9 |
| 9 | 32.4 | 35.4 |
| 10 | 32.2 | 35.3 |
| 11 | 31.9 | 35.3 |
| 12 | 31.6 | 35.3 |
| 13 | 31.3 | 35.4 |
| 14 | 31.1 | 35.4 |
| 15 | 30.9 | 35.3 |
| 16 | 30.7 | 35.1 |
| 17 | | 35 |
| 18 | | 34.5 |
| 19 | 30.5 | 34.5 |
| 20 | 30.4 | 34.7 |
| 21 | 30.2 | 34.7 |
| 22 | | 34.6 |
| 23 | | 34.1 |
| 24 | | 34.1 |
| 25 | | 34.1 |
| 26 | | 34.1 |
| 27 | | 34 |
| 28 | | 34.1 |
| 29 | | 34.1 |
| 30 | | 34.2 |

With regard to Trials 1-3, using pure water as the cooling liquid, the addition of esophageal, oral irrigation, and scalp flow to nasal irrigation more than doubled the rate of cerebral temperature drop from 30 min to 13 min for a 5° C. drop in brain temp. A temperature drop of 5° C. in 13 minutes is a remarkable rate of cooling. Head cooling still has an effect even without a pulse. After death of the animal, the core body and aortic temperature actually increased but brain temp continued to decrease. Hence the cooling liquid has a direct effect on the brain, in addition to the effect of cooling blood in the vessels that perfuse the brain.

Brain temperature also decreased significantly in Trial 3 despite two departures from optimal operating conditions. First, the esophageal tube was not optimally placed because the tip remained in the oropharynx in Trial 3 and served as a second oral tube. Second, the high viscosity of the 50% propylene glycol in water cooling liquid resulted in decreased flow rates of liquid into the aerodigestive tract. A much deeper and more rapid temperature drop would be expected with 20% PG and bath temperature of −10° C. because the viscosity would be lower and the flow rates of the liquid in the aerodigestive tract would be greater.

Nonetheless, the blood temperature achieved by adding aerodigestive cooling to scalp cooling is substantially lower than cooling merely the nasal cavity and scalp. Nasal+scalp cooling reached a minimum temperature of only 34° C. and equilibrated, while the addition of aerodigestive cooling achieved a blood temperature of 30° C. and was still decreasing when the experiment ended. This is a substantial difference; without aerodigestive cooling the total temperature drop was 4.7° C., while with aerodigestive cooling the temperature was 3.4° C. cooler in less time and had still not equilibrated.

In Trial 3 with propylene glycol, brain temperature reached a brain temperature of about 28° C. in 32 minutes, even though the experimental subject had been dead for about half that cooling time. Previously published reports have reported reaching temperatures of only about 33.4° C. in 30 minutes. Hence the aerodigestive cooling method is capable to cooling about twice as quickly in the critical first 30 minutes during which therapeutic hypothermia is being initiated.

The addition of esophageal flow helped increase the rate and depth of cooling. There did not appear to be any significant loss of cooling liquid into the stomach from the tube placed in the esophagus. Greater esophageal distension from even higher esophageal flow rates would be expected to increase the surface area of the esophagus, and provide a greater esophageal surface area for heat transfer to occur.

Since the sheep (98 kg) was larger than a typical human adult (60-70 kg), had a skull much thicker than a human skull, and possessed an effective boundary of fur despite close shearing, the rate and depth of direct brain cooling provided by scalp cooling is expected to be greater in humans. However, the inventor has demonstrated a much more rapid rate of cooling is possible using aerodigestive cooling as opposed to nasal cooling alone.

In some embodiments of the method in which more focal hypothermia is desired (for example, selective cooling of the brain) the body can be warmed, for example by wrapping the trunk and extremities in heating blankets. The cooling methods disclosed herein cool much more rapidly and deeply than previous methods by cooling a combination of surfaces, and/or using very high rates of flow of cooling liquid. The method is also versatile in that it can be used for substantially specific cooling of the brain alone or less specific cooling of the brain and other organs, either in or remote from a hospital setting or in transit between those sites. The method is capable of deeply cooling about 15% of cardiac blood flow (the blood flow to the head), is non-invasive to the extent that liquid is only introduced into the aerodigestive tract, and can combine internal and external cooling.

All regions cooled are integrated by combining all return liquid from the body, mixing and redelivering liquid to the body. The return of cooling liquid from the body in the experiments was passive, which allows for much higher flow of cooling liquid out of the nose and mouth, and in turn provides more rapid cooling. The simplicity of the equipment for carrying out the method allows for rapid implementation and broad applicability, so that more people can benefit from the simple sophistication of the approach. The simplicity of design, in which the method can be performed without inserting catheters into organs (such as the brain) leaves vital organs intact and allows more people to benefit from its use. The method and device can be used inside or outside a medical facility so that patients do not have to wait until they reach the emergency room to be treated. The method is suitable for use by less trained medical personnel (such as EMTs) without having to wait for a surgeon to arrive to perform invasive surgical maneuvers (such as introducing cooling catheters into the brain or blood vessels).

The brain can also be maintained significantly colder than the rest of the body during selective cooling, which maximizing brain benefit and minimizes body side effects. Rapid cooling can be induced much faster and attain much lower brain temperatures than with conventional induction of therapeutic hypothermia using prior art methods. In some examples, the temperature in the cerebral cortex is lowered to 33° C. in 5-15 minutes, or 28° C. in 10-20 minutes, or 25° C. in 15-30 minutes. In other examples, the temperature in systemic arterial blood is lowered to 33° C. in 5-15 minutes, to 28° C. in 15-30 minutes, or to 25° C. in 20-40 minutes.

A variety of different catheters/tubes can be used in the devices. Specific, non-limiting examples of particular catheter sizes are described above in relation to Trials 1-3. Examples of ranges of catheter sizes are $5/16$ to $1/2$ inches ID for the scalp tube, $3/16$ to $6/16^{th}$ inches for the esophageal and stomach tubes, $3/16$ to $1/2$ inches for the mouth tube, and $2/16$ to $6/16^{th}$ inches for the nose tubes.

The method is also capable of rapidly inducing cooling by using "stored cold" for the induction phase in the form of ice water or pre-cooled liquids that are available for emergency use, for example during the first 30 minutes of cooling. The temperature of the cooling liquid is also quite low, and using cooling liquids that are available at sub-zero temperatures to increase the rate and depth of cooling. The volumes of cool liquid available in the reservoir help maintain a sufficient supply for continued high volume flow of cooling liquid.

Organs are cooled by cooling the blood that supplies the organs, so that the disclosed methods do not require total body or even regional cooling to be effective. For example, if cooling of the cervical spinal cord is desired, this low mass region is rapidly cooled without waiting for the much more massive contents of the abdomen to be cooled.

The disclosed methods cool the head, neck and mediastinum using simple but effective techniques to maximize heat transfer. Selective cooling rapidly and deeply cools arterial blood delivered to the brain via the carotid and vertebral arteries. Non-selective cooling is capable of cooling venous blood returning to the heart, and therefore the systemic arterial blood. The venous blood is cooled in two regions, the neck and the mediastinum. The temperature of the blood draining from the neck is very low, in time approaching the temperature of the cold liquid bath that bathes it. This is due to cooling of the blood in the head and neck at the capillary level (most profound in the tissue beds in proximity to the skin and mucus membranes that are in direct contact with the cooling fluid) in addition to cooling of the blood in the jugular veins via cold fluid in the upper airway. About 15% of the cardiac output will be cooled in this very efficient manner.

The esophagus traverses the entire mediastinum and is in close proximity to the inferior vena cava, superior vena cava and the heart. The vena cava carries the entire cardiac output back to the heart. It is thin walled and lies in very close proximity to the esophagus, allowing for very efficient heat transfer with the esophagus. The stomach is in close proximity to the inferior vena cava as well as the inferior surface of the heart.

Direct contact of cooling liquids with the aerodigestive tract (as opposed to placing the liquid in a container within the tract) allows for the full surface area of the aerodigestive tract (from nares to pyloris) to be used for heat exchange. The cooling liquid enters irregular areas of the surface that balloons or rigid devices would not reach. Examples of such irregular surfaces that are bathed with the cooling liquid are the nasal trabeculae, tonsils, and larynx.

In addition to the convection due to flow of cool liquid through the aerodigestive tract, forced flow of the cooling liquid (both externally against the face and scalp and internally in the aerodigestive tract) contributes to convective heat exchange. For example, a thick layer of stagnant liquid at the outer aspects of the esophageal lumen could cause the flow of cool liquid to flow down only a central core that reduces heat exchange. Mixing can be increased by having multiple points of liquid delivery (multiple catheters and each catheter can have side holes), high flow rates, crossed currents of liquid flow (liquid is pushed into the body and generally directed towards the feet but changes direction and is expelled out the mouth and nose), encountering irregular surfaces in the aerodigestive tract (not smoothed over by a bag or balloon) and the presence of multiple delivery tubes along the path of liquid exit.

Another advantage of the method is that it is capable of providing the internal delivery of the cool liquid to the aerodigestive tract without immersing other parts of the body (such as the chest, extremeties or even in the head in some embodiments) in cooling liquid. Hence it is possible to perform other interventions on the patient that would not be possible in other types of induced hypothermia. Examples of such interventions include electrical cardioversion (applying electrical energy to the heart to change or initiate its rhythm), electrocardiography (obtaining diagnostic signals from the heart by applying external electrodes to the body, including the thorax), or performing cardiac or neurovascular surgery (such as angioplasty or stenting).

Temperature management devices and methods can be provided to achieve more rapid cooling, more brain selective cooling, and independent manipulation of brain and body temperature. The temperature management devices and methods described herein include methods of inducing and maintaining brain selective, systemic, and combined brain selective and systemic temperature management (e.g., cooling and warming).

The systems and methods described herein can generally be used in connection with one or more of the following activities:

1. Rapid Lowering of Brain Temperature, without Control of Core Temperature.

Possible clinical uses of this include, for example, treatment of cardiac arrest, MI, intraoperative organ protection, head trauma, stroke, hemorrhagic shock, fever.

2. Maintaining Brain Temperature Below Core Temperature while Maintaining Core Temperature Near Normal.

Possible clinical uses of this can include, for example, treatment of cardiac arrest, MI, intraoperative organ protection, head trauma, stroke, and hemorrhagic shock.

3. Maintaining Brain Temperature Below Core Temperature while Maintaining Core Temperature Below Normal.

Possible clinical uses of this include, for example, treatment of cardiac arrest, MI, intraoperative organ protection, head trauma, stroke, and hemorrhagic shock. This arrangement could be used to cool the brain very deeply while keeping the body core just above the temperature roughly 33-34 C where complications begin to appear. A neck wrap cooled by circulating cold fluid could be applied to deepen cooling. Counter warming—discussed in detail below—by heated blanket, on the body core or extremities or by surface warming of the scalp, or face could be applied to balance the "spillover" cooling—that is the cooling of venous blood due to the cold zone created in and around the aerodigestive tract. Warming of the neck surface could also be employed if care is taken to avoid the areas closest to the carotid arteries 4. Rapid Lowering of Core Temperature Especially Near the Spinal Cord, without Control of Brain Temperature.

Possible clinical uses can include, for example, treatment of spinal cord injury, MI, intraoperative organ protection, fever.

5. Rapid Elevation of Core Temperature, without Control of Brain Temperature.

Possible clinical uses of this include, for example, treatment of accidental hypothermia/exposure.

6. Controlled Elevation of Brain Temperature, with Control of Core Temperature.

Possible clinical uses of this can include, for example, rewarming after induced hypothermia.

7. Controlled Elevation of Brain Temperature, without Control of Core Temperature.

Possible clinical uses of this can include, for example, rewarming after induced hypothermia.

At least some of the disclosed systems and methods described herein allow rapid achievement and maintenance of a significantly lowered brain temperature (e.g., 35° C., 30° C., 25° C. or 20° C.) while optionally keeping body temperature in the vicinity of about 32° C.-38° C. This capability can be useful, for example, when treating cardiac arrest, stroke, traumatic brain injury, and other such events. This capability can also useful to provide perioperative neuroprotection during such procedures as aneurism clipping and coilings, and coronary artery bypass grafts (CABG). Also, this capability can be well-suited for addressing fever spikes that are commonly associated with brain injury with minimal disturbance of the patient's core temperature. The systems and methods described herein can also, in at least some examples, (1) reduce intracranial pressure after brain injury, (2) reduce the risk of pneumonia commonly associated with cooling therapy, and/or (3) provide a means of controlled re-warming, whereby the brain is returned to equilibrium with the body by reducing the brain focused cooling or using brain focused and/or body focused warming.

In some examples, a warming function can be provided to further improve the selectivity of the device. The system can also include an interface kit that contacts the patient and a base unit that does not contact the patient or fluids going into or out of the patient. The base unit can be reusable because it is generally maintained separate from the patient. In some examples, the systems and methods discussed herein can also include a single use heat exchanger that can be interfaced with the re-usable base unit.

An interface system (or kit) can comprise a fluid path and, if desired, associated protective equipment. The fluid path can be configured for a single use. Accordingly, in some examples, the fluid path is referred to as a single use fluid path. However, it should be understood that the fluid path can alternatively be configured to be sterilized for reuse.

As discussed in more detail below, the interface system can comprise one or more of the following components: nasal catheter(s), esophageal catheter(s), tracheal catheter(s), oral catheter(s), return manifold(s), switching valve(s) or clamp(s), filter module(s), waste reservoir(s), connecting line(s), recirculation reservoir(s), vent(s) for reservoir(s), heat exchanger(s), manifold(s) associated with the heat exchanger(s), and straps and/or adhesives to secure one or more of the catheters of the system as desired. As will be understood by one of ordinary skill in the art, various combinations of these and other features described herein are possible in connection with providing a novel interface system in accordance with the disclosed embodiments.

Associated protective equipment can include, for example, disposable covers for temperature probes that contact the patient or disposable temperature probes.

A single use fluid path can comprise one or more nasal, esophageal, tracheal, and oral catheters. For example, two single or multi-lumen nasal catheters can be configured to be introduced through the nostrils of the patient. The tip of each catheter can be inserted to a depth of 1 to 15 cm from the nares. The lumens of the catheters enable fluid communication of the nasopharynx with a source of fluid, which can be, for example, between −20° C. and 37° C. Clamps, straps, adhesive, or other means of affixing the catheters to the patient can be included. These catheters can include foam or other such flow restricting members to prevent fluid introduced into the nasopharynx from leaking back out the nose. In other embodiments, an apparatus can be configured to enclose the nose. These catheters can also include multiple ports to direct fluid flow toward key structures in the pharynx such as the turbinates or the orifices of the sinuses. If desired, these catheters can be notched, marked or color coded to indicate depth of insertion. Clamps or valves can also be used to adjust flow rates in the catheters.

An esophageal catheter can also be included with the interface system. The esophageal catheter can comprise a multi-lumen catheter. The tip of the catheter can be inserted so that the distal tip lies within the esophagus. A primary lumen (preferably larger than one or more secondary lumina) can extend from a proximal end of the catheter to a distal end, providing access to the stomach and/or a means for emesis to leave the stomach. A secondary lumen can extend from the proximal end and terminate inside a flexible balloon located near the distal end. The balloon can be inflated to reduce or prevent entry of fluid into the stomach from the esophagus. Another (e.g., a third) lumen can extend from the proximal end to a port proximal to the balloon to provide fluidic communication between the port and a source of fluid (e.g., fluid at a temperature between $-20°$ C. and $37°$ C.) or a source of negative pressure. This third lumen can be used to irrigate the esophagus with cold fluid or to remove fluid from the esophagus proximal to the balloon. Additional lumens can be provided to facilitate the above or other purposes, such as to provide an additional balloon, additional fluidic communication between the proximal portion of the esophagus and the outside of the body environment, fiber optic devices, and/or pressure measurement or temperature measurement probes.

FIGS. 18A-C and 19A-D illustrate various esophageal catheters that can be used in connection with the cooling and temperature management systems described herein. FIGS. 18A-C illustrate various multi-function esophageal catheters; however, many other embodiments are possible by, for example, added lumens for access of additional instruments, added irrigation lumens, etc. One example would be adding lumens to accommodate thermocouples or optical temperature sensors to measure esophageal temperature above and below the esophageal balloon. Comparison of the "dry" and "wet" esophageal temperatures can provide information on cooling rate and serve as a macroscopic leak detector. Also, similar functionality can be created, for example, by affixing a bundle of tubes together, or one or more tubes to the outside of a standard esophageal catheter. The multi-functional esophageal catheter may also include grooves, fins, or side (non-annular) balloons for the purposes of promoting even flow of cooling fluid, or distending the esophagus in a manner favorable for heat transfer (such as increasing surface area or reducing distance to key arteries). Catheters of the present invention can also comprise non-circular channels (e.g., depending on a desired pressure within the system (e.g., the catheter or the cuff), a desired flexibility of the catheter, etc.). Flow in lumens can also be reversed when it is desired to remove fluid form the patient.

FIGS. 19A-D illustrate a "double section" balloon esophageal catheter that can be used in embodiments of the cooling and temperature management system disclosed herein. A suction lumen can be positioned between the balloons to create a small zone of low pressure when suctioned to help prevent fluid migration beyond the "lower" cuff, which governs entry of fluid to the stomach. An alternative configuration includes an optional second balloon line, allowing separate inflation of balloons. This has the added advantage that the compressed area of the esophagus can be changed from time to time.

A tracheal catheter can also be included with the interface system. The tracheal catheter can comprise a multi-lumen catheter. The tip of the catheter can inserted so that a distal tip is positioned within the trachea. A primary (preferably larger) lumen can extend from a proximal end to a distal end, providing access to the large airways of the lung for the passage of air, respiratory gases, medications, and/or instruments. A second lumen can extend from the proximal end and terminate at (e.g., inside) a flexible balloon located near the distal end. The balloon can be inflated to reduce or prevent entry of fluid into the lungs from the trachea proximal to the balloon (subglottic space). A third lumen can be provided to extend from the proximal end to one or more ports near the distal end but proximal to the balloon to provide fluidic communication between the port(s) and a source of fluid or vacuum. The third lumen can be used to allow the removal or delivery of fluid to the subglottic space.

FIGS. 20A-C illustrate exemplary embodiments of a multi-lumen tracheal catheter for use with the cooling and temperature management system disclosed herein. Many other embodiments are possible, including added lumens for access of additional instruments, added irrigation lumens, etc. Also, similar functionality can be created by affixing a bundle of tubes together, or one or more tubes to the outside of a standard endotracheal tube. Flow in lumens can also be reversed when it is desired to remove fluid from the patient. The balloon can be inflated to shield the lungs from fluid in the trachea.

FIGS. 21A-D illustrate exemplary embodiments of a "double section" balloon tracheal catheter that can be used in embodiments of the cooling and temperature management systems disclosed herein. A suction lumen is positioned between the balloons to create a small zone of low pressure when suctioned. This prevents fluid migration beyond the "lower" cuff governing entry of fluid to the lower trachea. The balloons can be inflated to shield the lungs from fluid in the trachea. The shielding effect can be increased by connecting the lung access lumen to a ventilator and adding a slight positive pressure to the lungs. This shielding effect is synergistic with the effect created by low pressure zone between the balloons. An alternative configuration includes an optional second balloon line, allowing separate inflation of balloons. This has the added advantage that the compressed area of the trachea can be changed from time to time.

One or more oral catheters can also be included with the interface system. The oral catheter(s) can be inserted to the back of the mouth to remove irrigation fluid from the patient and/or deliver irrigation fluid to the pharynx. The catheter can be in fluidic communication with a return manifold and/or a delivery manifold. The fluid in the oral catheter can be moved by pump or vacuum. In some cases, the oral catheter can be a lumen of the tracheal tube and/or the esophageal tube, or it can be a dedicated line that suctions liquid from the mouth area. The suctioned fluid can be discarded, or filtered and then re-circulated. A key point is that the flow rate entering the oral catheter can be adjusted independently of the fluid delivery rate, thus allowing control of the liquid level in the patient's mouth. For example, the oral catheter can be manually adjusted to alter the height of the fluid column within the pharynx. The oral catheter can comprise one or more ports in the catheter wall that can be used to adjust the height of the fluid column within the pharynx. The oral catheter ports can also be encased in a mesh or filter that would prevent adherence of the catheter to the mucosa when suction is active.

As noted above a return manifold can be provided in fluidic communication with the oral catheter to allow fluid in the oral catheter to be discarded or re-circulated. A switching valve or clamp can also be provided to allow a user to route fluid leaving the patient to the recirculation reservoir or the discard reservoir. The valve can be disposable and interfaced with external automation. Alternatively, the valve can be manually operable.

A filter module can also be provided. The filter can be configured to accept fluid to be re-circulated. The filter removes bacteria and particles greater than 0.1 micron or greater than 0.5 micron or greater than 1 micron or greater than 5 microns or greater than 10 microns in size. A series of filters of varied size can also be utilized.

A waste reservoir can be provided to receive fluid that is to be discarded. The waste reservoir can have a capacity between about 1 and 20 liters. The reservoir can have at least one inlet and, if desired, can be at or below atmospheric pressure to facilitate waste removal. Waste reservoirs and recirculation reservoirs can comprise a sleeve and/or bag configured to hold fluid and configured to be removed and replaced at the end of the procedure.

Additional features can include a line for connecting the waste reservoir to a vacuum source, and a vent for the waste reservoir. The vent can be configured so that it can be opened or closed as desired.

In some examples, a recirculation reservoir can also be provided. The recirculation reservoir can receive and hold fluid for recirculation. If the fluid is to be filtered, the fluid can be filtered before entering or after leaving the recirculation reservoir. The recirculation reservoir can also accept an initial charge of fluid. The recirculation reservoir is at or below atmospheric pressure. The reservoir can have a capacity of 1-20 liters. In some cases the reservoir can be incorporated into the heat exchanger, with the "hold up" volume of the heat exchanger replacing all or part of the reservoir volume. At the start of cooling, the reservoir can be charged an initial charge of cooling fluid, which may be, for example, about 2 L of 0.9M saline; however, other concentrations and formulations of fluid may be used as disclosed herein. The reservoir can also accept additional fluid volumes during therapy to compensate for any fluid lost due intentional discard, leaking, spillage, etc.

A line can be provided for connecting the recirculation reservoir to a vacuum source. One or more vents can be associated with the recirculation reservoir and the vents can be operable between and open and a closed position, either in a manual or automated manner.

The systems of the present invention can comprise one or more heat exchanger (e.g., plate-type heat exhcanges, shell exchangers, tube exchangers, etc.). In some examples, the heat exchanger comprises a single use heat exchanger in fluid communication with the recirculation reservoir. The heat exchanger can be configured to exchange thermal energy with a reusable cooling unit. The heat exchanger can, in some examples, be in thermal contact but not fluidic contact with the cooling unit. In other embodiments, the heat exchanger can be in fluidic contact with the cooling unit, but provide two or more distinct fluid paths. The heat exchanger can be made of relatively high conductivity materials, such as various metals including, for example, copper, aluminum, and/or steel. The heat exchanger can, in some examples, be configured to allow between 100 and 2000 watts of heat exchange, and can be configured to accommodate flow rates between, for example, 0.2 and 5 L per minute (e.g., having a pressure drop of less than 15 PSI). The heat exchanger can be configured to provide a fluid path with a high surface area of up to 1 m$^2$ and interface with the base unit as described in more detail herein. Of particular interest are cases where fluid path through the heat exchanger is "very long" such that the temperature of cooling fluid is nearly completely equilibrated with that of the exchanger walls. For a rectangular channel geometry, this equilibration will occur when the dimensionless length of the channel is greater than about 1.2, with values above 2.0 being especially desirable (see Middleman, S An Introduction to Heat and Mass Transfer, p 458) Thus the temperature of the cooling fluid entering the patient is readily inferred from that of the heat exchanger and/or base unit platens, and thus controlled. The portions of the heat exchanger that are not in direct physical contact with the cooling elements of the base unit can be insulated to reduce heat exchange with ambient air. It is understood that some condensation occur even on the insulated sides, for this reason the sides are shaped to direct condensate into a drain or waste container.

A manifold in fluidic communication with the heat exchanger can also be provided. The manifold can divide the flow of cold fluid, as desired, between the esophageal catheter and the nasal catheters.

Various straps and/or adhesives can also be provided to hold or maintain one or more of the catheters in a desired position.

In some examples, a tracheal tube can be in place in a patient prior to implementation of one or more components of the interface kit. In such cases, in can be desirable to leave the preexisting tracheal tube in place rather than disrupt the airway. Thus, it might not be desirable to insert a new or additional tracheal tube, such as those described herein, until it is safe to do so. Nevertheless, cooling could still be accomplished without the tracheal suction.

An optional warming functionality may also be included. A warming device can provide warmth to the body core to counteract the cooling of the core caused by venous blood returning from the cooled brain through the cooling zone along the aerodigestive tract. Warming can be provided by hematogeneous and or surface warming strategies. For example, a warming device can comprise one or more heated blanket or pads that can be positioned on or around the patient. Warming of the scalp or face is another possible strategy.

Thermal energy can be supplied to one or more warming devices by recirculating warm fluid, forced warm air, or direct resistive heating. In some embodiments, where an array of thermoelectric cooling devices is used, an additional "hot side" heat exchanger can be provided to remove heat from the hot side or heat sink of the thermo electric devices. This has the advantage of improving the efficiency of the thermoelectric device while avoiding the need for cooling fans. A further advantage is that the use of this recaptured heat allows for a smaller and potentially safer heating system.

One or more temperature probes can be provided to monitor the temperature of the warming device and/or skin temperature of the patient. This measurement can be used, for example, to monitor the warming device to reduce a risk that the warming device gets the skin too hot (e.g., beyond about 42° C.), thereby delivering too much heat to the patient and possibly harming the patient's skin.

The power supplied to the warming device can be modulated as a function of the rate of energy removal, measurements of patient temperature, especially rectal temperature, bladder temperature, brain temperature, venous blood temperature, and/or the total energy removed from the patient by the cooling device. The warming device can be used to maintain the body near normothermic temperature of 37° C. as measured by rectal or other temperature probe, while the brain is maintained at a lower temperature. In this way, the neuroprotective advantages of cooling the brain can be achieved and the occurrence of complications associated with cooling the body can be reduced and/or substantially eliminated.

The warming device can also be used to maintain the body near a lowered temperature set point of about 32° C.-36° C. as measured by rectal, bladder or other temperature probe, while the brain is maintained at a still lower temperature. In this way, the neuroprotective advantages of deep cooling the brain can be achieved and the occurrence of complications associated with cooling the body can be held at a controlled, acceptable level.

If the temperature probes that are used are not disposable in their entirety, disposable covers can be provided for contact with the patient and with fluids contacting the patient. In some examples, the covers are thin conductive plastic and/or rubber.

A base unit can be provided to interface with the patient interface system/kit described herein. The base unit can comprise one or more of the following components: reusable and/or disposable temperature probe(s), fluid temperature measuring device(s), processor and/or data acquisition system(s), reusable cooling unit(s), heat removal device(s), pump(s), pump control unit(s), and/or cooling unit(s). As will be understood by one of ordinary skill in the art, various combinations of these and other features described herein are possible in connection with providing a novel interface system in accordance with the disclosed embodiments.

In some examples, the base unit can be configured to enable the user to measure data from the patient. For example, the base unit can be configured (e.g., by placement of temperature sensors) to receive, obtain, and/or display a temperature of the patient at certain locations (e.g., brain, rectal, tympanic, axillia, skin, central venous, temporalis muscle, distal to an esophageal and/or tracheal cuff, proximal to an esophageal and/or tracheal cuff, external ear, toe, finger, exhaled gas, etc.). Not all possible measurement locations need be obtained. In some examples, a simple rectal temperature measurement is sufficient. However, brain temperature can be critical. For example, in some embodiments, a temperature sensor can be disposed exterior or interior to entrance catheters (catheters through which the cooling fluid can enter the aerodigestive tract) and exit catheters (e.g., catheters through which cooling fluid can be actively removed from the aerodigestive tract). These temperature sensors can be coupled to the base unit and configured such that the base unit can measure a temperature difference (e.g., to provide a user with at least some information regarding brain temperature).

Other temperature monitoring methods and/or devices can be used to help accurately determine brain temperature. For example, an invasive method can comprise disposing a bolt in a subject's brain (e.g., in the event that cranial pressure should be released and/or an accurate temperature reading should be obtained). As another example, temperature sensors can be coupled to a line and inserted intravenously (e.g., in a jugular) and positioned near to the brain. As yet another example, a non-invasive method can comprise exposing a subject to an MRI during a procedure to obtain one or more temperature readings.

The base unit can also be configured to receive, obtain, and/or display measurements of pressures in the patient, including, for example, pressures in the trachea, esophagus, and/or intracranial areas of the patient. For example, an esophageal and/or endotracheal cuff can be configured (e.g., with a pressure sensor) to detect and/or measure a pressure (e.g., a pressure inside the cuff). A base unit can be coupled to the pressure sensor (e.g., via an electrical connection running within a catheter) such that the base unit can receive and/or obtain detections and/or measurements from the pressure sensor. A base unit can further be configured such that when a threshold pressure is met or exceeded, an alert (e.g., audio, visual, etc.) occurs. In some embodiments, the threshold pressure can be adjusted by a user. The threshold pressure can also be pre-determined (e.g., based on the anatomical deployment of the cuff, a cuff material, and the like). In other embodiments, a pressure within a cuff can be automatically adjustable based on pressure detections and/or measurements from the pressure sensor, a desired pressure, anatomical deployment of the cuff, a rupture pressure, and the like.

In other embodiments, the base unit can further be configured to measure flow rate of the cooling liquid. A flow sensor can be positioned (e.g., within the base unit, along a length of one or more catheters (e.g., interior or exterior), within a cuff, and the like) such that the flow rate of the cooling fluid can be measured going into and out of (e.g., in the case of active removal of the liquid) the subject.

Other sensors and/or measurement devices can be configured to interface with the base unit such that the base unit can receive information (e.g., an IV unit can send and/or permit the base unit to obtain information regarding fluids delivered by the IV unit to a subject).

In some examples, the base unit can be configured to provide motive force to move fluid into or out of the patient, add or remove heat from the fluid entering the patient, and/or display certain data on the patient's condition (including, for example, the temperature and/or pressure readings described above). The base unit can provide a simple closed loop feedback control of a single temperature, or in more sophisticated embodiments can allow the user to program certain time courses for patient temperatures, such as approaching a given temperature set point at a specified rate, holding the patient near a specified temperature for a specified period of time, and re-warming the patient at a specified rate.

The base unit can comprise a re-usable or disposable temperature probe for use in monitoring patient temperature in communication with a temperature display. More than one temperature probe may also be used. In some examples, there can be at least a measurement of rectal temperature of the patient. Optional temperature probe(s) can be used to measure temperature of liquid entering and returning from the patient. In some examples, the temperature probes can be isolated from the fluid by a disposable but highly thermally conductive material such as a thin aluminum or plastic sleeve. In some examples, a thermally conductive grease or gel can be used to enhance thermal contact between the probe sending element and the sleeve. A processor and/or data acquisition system can be provided and configured to communicate with and/or receive information from the temperature probe or probes. A display screen or other such device can be provided to display the information received from the one or more temperature probes.

A reusable cooling unit can be provided and configured to accept a heat exchanger. In some examples, the heat exchanger comprises one or more e cartridge with a rectangular "box" geometry. The cartridges can be—but are not required to be—removable and/or disposable. The cartridges can comprise an inlet and outlet port on the same or different sides of the cartridge. The cooling unit can be configured to close to bring one or both sides of the cartridge into thermal contact with the cooling elements. In this manner, heat can be transferred by conduction without the cooling elements being in fluidic contact with the cartridge. The contact with the cartridge can be established with one or two smooth and/or featured conduction surfaces constructed of a thermally conductive material such as, for example, aluminum, steel, or copper. In some examples, the conduction surfaces can also be in contact with an array of thermoelectric cooling devices (described in more detail below) that pump heat away from the surfaces, reducing their temperature.

In some examples, one or more devices to remove heat from the "hot" side of the thermoelectric devices can be provided. Removal of heat can be by free convection or enhanced by use of fins, fans, or by attaching a "heat pipe", a heat pipe being a reservoir of fluid that is warmed or boiled by waste heat from the thermoelectric devices. The warmed fluid can move via capillary action, or by gravity. In the gravity driven case, he fluid vapor can rise to another part of the reservoir in thermal contact with the ambient environment, and condense there dissipating heat to the environment. The fluid can then fall back into the reservoir after condensing. Alternatively, the fluid can be pumped to a cool part of the reservoir or a cooling coil.

In some examples, at least one pump can be positioned before or after the heat exchanger to propel fluid into the patient. The pumps can be peristaltic pumps to prevent fluid contact with the pumping mechanism. In some examples, however, diaphragm pumps and other types of pumps such as a rotary pump can be suitable. If desired, a disposable fluid contact section can be provided with the diaphragm or rotary pump.

The pump(s) can deliver up to 0.2 l/min, between 0.2 and 2 l/min, up to 2 l/min, between 0.5 to 10 l/min, between 10 and 20 L/min or in some examples, up to 20 l/min. Depending on a desired startup speed, intermittent pump timing and pre-cooled liquid can be considered. In some examples, two peristaltic pumps can be provided to propel fluid into the patient, with one pump governing the flow rate into one or more esophageal catheters and the other governing flow rate into one or more nasal catheters. A control unit can be provided to allow the user to control the speed of pumping and/or to turn the pump(s) on or off.

One or more cooling units can be provided to interface with the heat exchanger, a user interface, and/or the data acquisition system. The cooling unit can use one or more thermoelectric devices (e.g., to permit modulation of cooling output). In other embodiments, other types of cooling can also be used, such as an ice bath or a conventional refrigeration unit. In other embodiments, recirculating chillers (e.g., thermoelectric or conventional refrigeration) can be used to permit cooled fluid to enter one side of a heat exchanger, where another side of the heat exchanger comprises fluid to be introduced to a patient. The recirculating chillers can be adjusted to permit modulation of the cooled fluid. Recirculating chillers can comprise 1000-2000 watts of cooling capacity at 0° C.

The data acquisition system can be configured to interface with the control unit and the temperature probes that come in contact with the patient. A module associated with the data acquisition system can be configured to acquire data on the temperature of the liquid streams entering and returning from the patient. The module may acquire intracranial pressure data (ICP) in some cases.

In some examples, cooling unit can comprise a system with a dry interface with the heat exchanger. Thus, the heat exchanger can be in thermal contact with the interface, but not fluidic contact with the cooling/heating elements of the base unit. In some examples, the interface can be a two-sided interface that allows for maximum cooling of the working fluid with minimal residence time.

A variety of heat sink strategies can be used to dissipate heat from the "hot" side of the thermoelectric device as rapidly as possible. For example, fans can be used to force air over a finned heat exchanger. Alternatively, and preferably in many cases, the hot side of the thermoelectric device can be put in contact with a circulating liquid and the liquid used to simply dump the waste heat or even to warm the patient. Another possible heat sink strategy employs one or more reservoirs of liquid with significant head space being in thermal contact with the hot side of the heat exchanger. When the thermoelectric devices are cooling the patient, they are simultaneously boiling the liquid in the reservoirs the liquid will condense on the interior surfaces of the reservoir, which will result in the heat being conducted away to the environment. In some examples, the thermoelectric elements can be used to warm the fluid going into the patient by, for example, conducting heat from the environment into the "cold" side of a thermoelectric device. This arrangement has the advantage of reduced complexity compared to forced air cooling/warming. The concept is similar to that of a reflux condenser.

The term "heat sink" as used herein also includes heat pipes. Various working fluids can be utilized in such heat pipes, including, for example, water, ethanol, methanol, fluorocarbons, and any mixtures of those. The temperature at which the pipe operates is determined by the pressure inside the reservoir. In one example, the temperature of heat pipe operation can be between 45° C. and 55° C., which is generally warm to the touch but not a burn hazard.

In some examples, the heat pipe can be a gravity heat pipe. In other examples, the heat pipe can be operable using capillary action, such as conventionally used in high performance computers. Heat pipes can provide several advantages over the use of conventional fan and fin systems to dissipate heat. For example, fan and fin system can be more difficult to clean. In other embodiments, as described above, a heat exchanger (e.g., a plate heat exchanger) can be in fluid communication with a cooling unit (e.g., configured to cool fluid directly entering a patient or indirectly through a heat exchanger).

Management of a given patient's temperature can comprise three basic phases. An initial cooling or "induction" phase can be performed to bring the patient to a hypothermic or normothermic state. This phase can be followed by a "maintenance" phase where the patient's brain and body temperatures are maintained at their respective goal temperatures as determined by the physician for a period of time ranging from a few hours to several days. Finally a "re-warming" phase can be provided in which the brain and body are returned to their normal temperatures in a controlled fashion.

Figure 11:
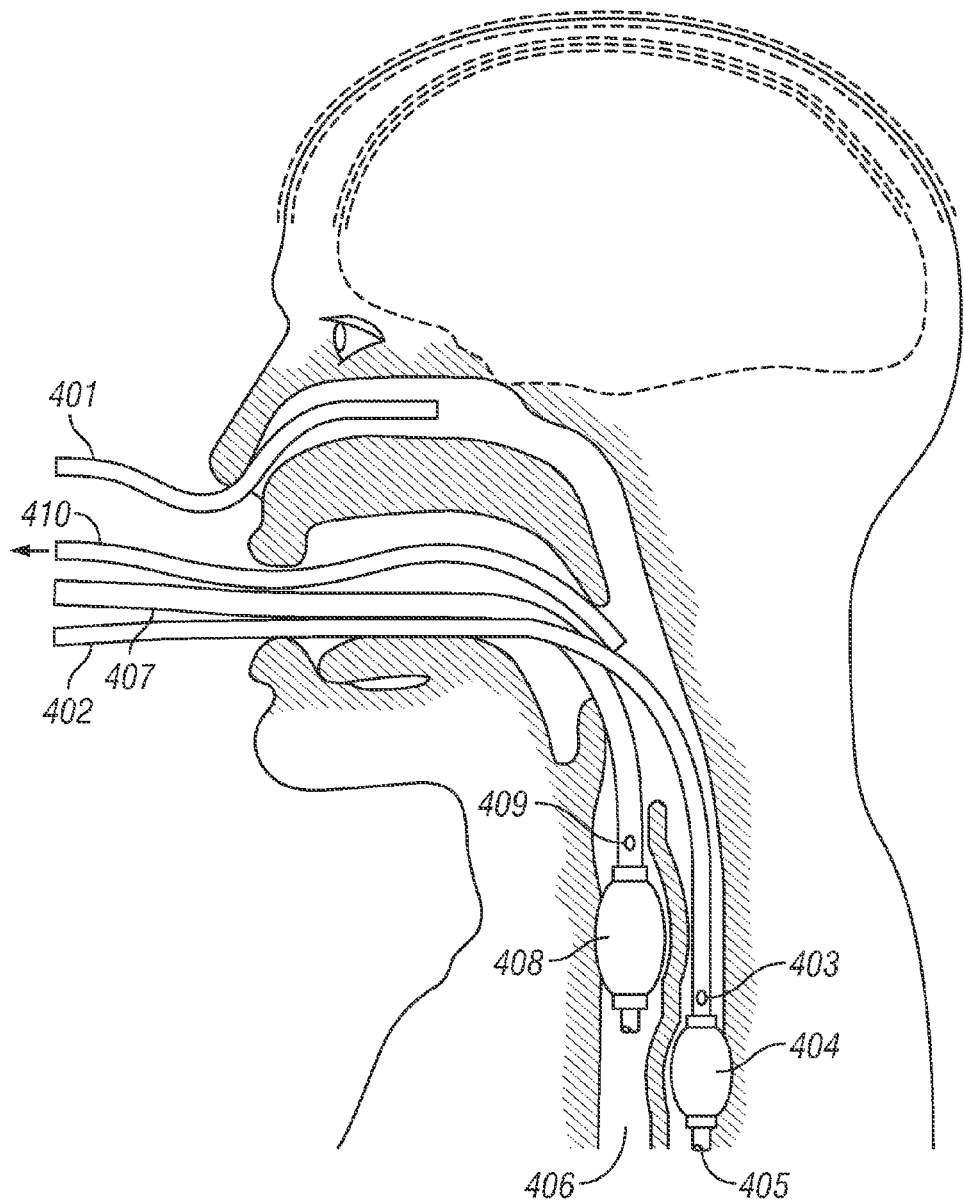
FIG. 11 illustrates one configuration of a "long column" cooling strategy and the resulting fluid flow field. Long column cooling methods can, for example, permit faster and/or deeper cooling. As another example, long column cooling methods can allow for and maintain a larger steady state gradient between brain temperature and body temperature than other methods. In some embodiments, the physical length of the column can be lengthened or shortened depending on a given regime of medications, anesthetics, and/or agents administered during a procedure, as discussed in detail below (e.g., the physical length of the column can be shortened when an intensive anesthetic regime is used).

FIG. 11 illustrates an exemplary "long column" cooling strategy and can be used to describe the resulting fluid flow field. By providing a longer cooling zone than "nasal only" strategies, the long column method allows for faster and deeper cooling. In addition it allows a larger steady state gradient between brain temperature and body temperature to be achieved and maintained.

As shown in FIG. 11, cold fluid can be supplied through nasal catheter 401 and multi lumen esophageal catheter 402. Fluid can exits into esophagus through port 403 while fluid loss to the stomach is prevented with balloon 404. Balloon 404 can also regulate aspiration of stomach contents. Large lumen catheter 405 can preserve stomach access and prevents pressure increase in the lower esophagus or stomach by providing an exit path for emesis and intestinal gas.

Fluid entry into lower trachea 406 can be reduced or prevented by balloon 408 and port 409 can permit the removal of fluid in the trachea to help reduce and/or prevent fluid stagnation. Fluid entry in to the lower trachea may be further reduced by using a ventilator to create a slight positive pressure in the lungs. A main lumen of a multifunctional endotracheal (tracheal) tube 407 can permit respiration. Main exit line 410 can be configured to recover fluid for filtering and recirculation or disposal. Patient may be placed flat or in Trendelenberg position to aid fluid removal In use, the system shown in FIG. 11 (and in other figures as applicable) can be implemented as described in the exemplary method below:

1. Induction Phase (Once it is Determined that Cooling is Appropriate for a Brain Injured Patient)

a. If not already intubated, a cuffed ETT (with or without additional ports and lumens) is inserted to protect the lungs. The ETT may have additional lumens and ports. The cuff is inflated to a pressure of 20-50 cm water. If a double balloon or cuff ETT or catheter is used, its second balloon can be inflated.

b. An esophageal tube is inserted into the esophagus and its cuff inflated to 20-60 cm water to protect the stomach.

c. Nasal catheters are inserted into the nostrils.

d. The oral catheter is placed in the mouth.

e. The liquid carrying tube lines are attached to their respective manifolds (nasal, tracheal, esophageal, and return).

f. The return line is connected to the reservoir.

g. The fluid path is completed by placing the single use heat exchanger or heat exchangers in the cooling unit and possibly the warming unit.

h. The reservoir is charged with cooling fluid i. The cooling unit is activated.

j. The pumps are activated.

k. Fluid flow is now established and can move in a circuit (see, e.g., FIGS. 10A, 10B, and 10C).

l. The flow field inside the patient (see, e.g., FIG. 11).

m. Given that the aerodigestive tract may contain infective material such as gastric contents or pharyngeal fluid, the first liter or so of fluid exiting the patient may be discarded and not recirculated. If a double balloon tracheal catheter is used, flushing or slight suction may be applied to the space between the balloons or cuffs in the trachea to shield the lungs from infective fluid ingress. In addition, pressure may be slightly increased in the lungs using a ventilator to further shield against fluid ingress into the lungs.

n. Measurement devices (thermocouples or thermistor based devices) are introduced in the rectum, or axillia. If a central venous line and or "bolt" are present these temperatures can be acquired. Intracranial pressure data may also be acquired if available.

o. After the cold fluid circuit is established, brain temperature will decrease rapidly, while body temperature will decrease more slowly than that of the brain. During induction, it is possible that the warming function will not be used.

p. A patient's body core temperature can be left near normal temperatures. In other cases, however, a patient can be cooled until body core temperature is below 36° C., 35° C., 34° C., 33° C., 32° C., or lower, and in some cases 26° C., 25° C., 24° C., or lower. It is desired that the brain will be colder than the core temperature. As the core temperature approaches its set point, the warming unit will be engaged, eventually reaching a steady state where the heat extracted by the cooling unit is balanced by the heat supplied onto the patient by the warming unit.

q. In the event that brain temperature measurement is available and that the brain temperature is the controlled variable of the control loop, the brain temperature will be monitored and when the brain temperature approaches its set point, the cooling will be discontinued and/or the warming unit will be engaged, eventually reaching a steady state where the heat extracted by the cooling unit is balanced by the heat supplied onto the patient by the warming unit.

2. Maintenance Phase a. Once the patient reaches goal temperature, control actions will be taken as needed to maintain the patient in the vicinity of the goal temperature. Many control methods are described in the art including PID methods, multi input, single output control (MISO) and multi-input multi-output control (MIMO). Internal model control (IMC) can also be used.

b. In addition to other treatment, intermittent flushing of the aerodigestive tract may be undertaken to prevent stagnation of fluids (particularly in the trachea) during this "maintenance phase."

c. In addition, intermittent suction may be placed on the tracheal ports to prevent stagnation of fluids "above" the cuff protecting the lungs. In this context, "above" means on the side of the cuff closest to the mouth rather than closest the lungs.

d. During maintenance phase, both cooling and warming may be increased to allow a greater gradient between brain and body temperature. This may correspond with a decrease in the temperature of the cooling fluid used to irrigate the patient, or an increase in the duty cycle of the system (e.g., minutes of active irrigation per hour of elapsed time).

e. During maintenance phase temperature of the irrigation fluid may be modulated to increase or decrease the rate of cooling. The flow rate of the irrigating fluid may also be modified, including intermittent stoppage of irrigation of all or part of the aerodigestive tract.

3. Re-Warming Phase a. During re-warming, if a warming device is not present, the cooling system power or duty cycle is decreased and the patient is allowed to re-warm. If a warming blanket is present additional energy may be applied to the patient as the cooling is reduced.

b. As the patient approaches goal temperature, the power to the warming device is reduced or the warming device is switched off c Fluid is recovered from the patient as needed and catheters removed when appropriate.

As discussed above, patients relying on mechanical ventilation can be particularly susceptible to pneumonia, as bacteria present in the mouth and pharynx enter the lungs. However, flushing the upper airway and esophagus with cooling fluid can mitigate this risk by several mechanisms. First, flushing entrains saliva, mucus and pharyngeal fluid, and sweeps the associated bacteria away. The bacteria are thus prevented from multiplying and accumulating in the aerodigestive tract. Second the flushing dilutes the nutrients required by for bacterial growth reducing the multiplication rate of the bacteria not swept away. This is especially important in instances where the patient has recently vomited or in danger of aspirating stomach contents. Third because the flushing fluid is very cold the temperature of the surfaces of the aerodigestive tract are reduced considerably, further depressing the rate of bacteria growth. The net result of these effects is that any liquid that does enter the lungs is likely much less infective than that entering the lungs of an un-flushed patient. It is also possible to add antibacterial agents and surfactants to the irrigating fluid.

Patients undergoing cooling for the sake of neuroprotection are often especially vulnerable to pneumonias because of the immune system suppression associated with reduction of patient core temperature. The selective cooling system largely avoids cooling the core and leaves the patient's own immune system better able to fight infection. This benefit is further enhanced by the fact that surface warming can be applied independently, or with an integrated warming device.

Flushing can be performed by allowing the fluid to exit and circulate as described above with respect to FIG. 11 and elsewhere. In addition, an exemplary method for flushing can be performed as follows:

1. At least the tracheal catheter is introduced into the patient, but additionally, any or all of the nasal, or esophageal, catheters as well as the return line are introduced into the patient.

2. The nasal catheter and/or esophageal catheters are used to introduce fluid in to the patient. Even a lumen of the tracheal catheter itself may be used.

3. Suction is applied intermittently to the suction port of the tracheal tube.

The flushing can be part of a cooling process, or it can be distinct from cooling in that it can be performed with fluid close to the patient's core temperature.

Figure 22A:
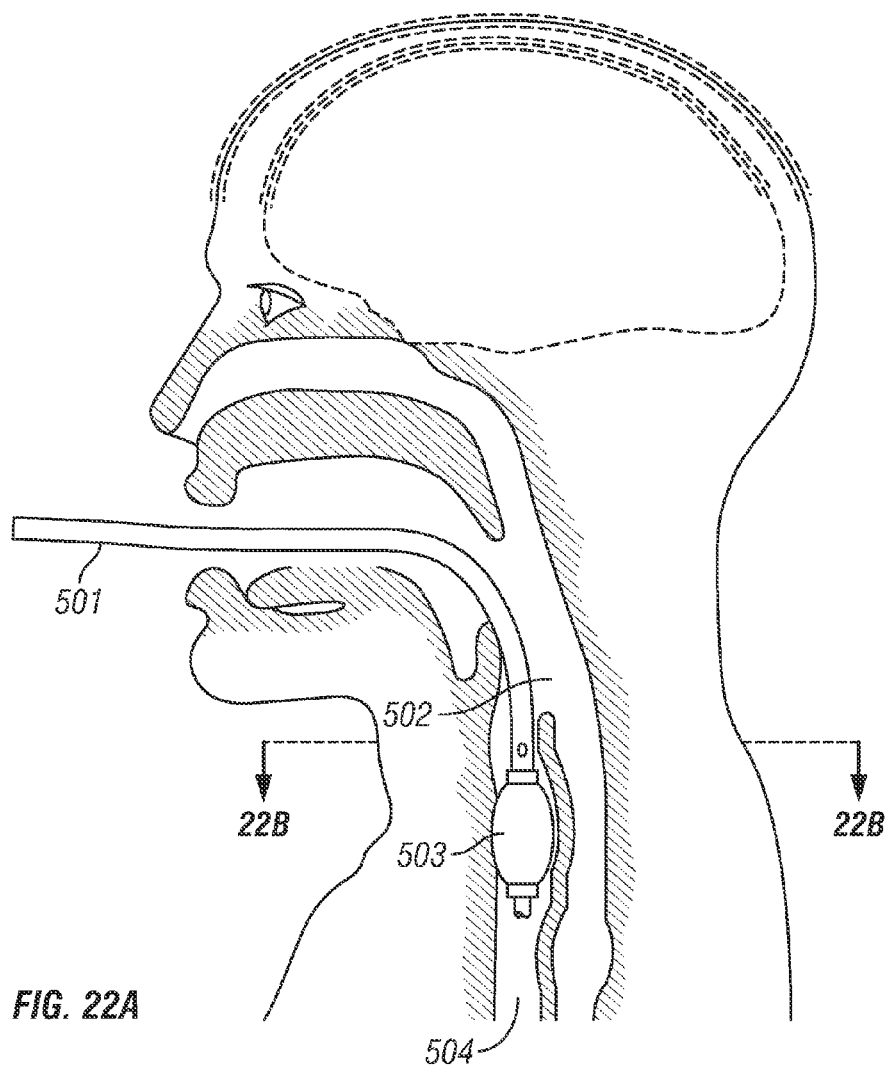
FIGS. 22A-B show one example of a flushing concept using a multi-function tracheal tube and an exemplary section view taken along line A-A in FIG. 22A.
Figure 22B:
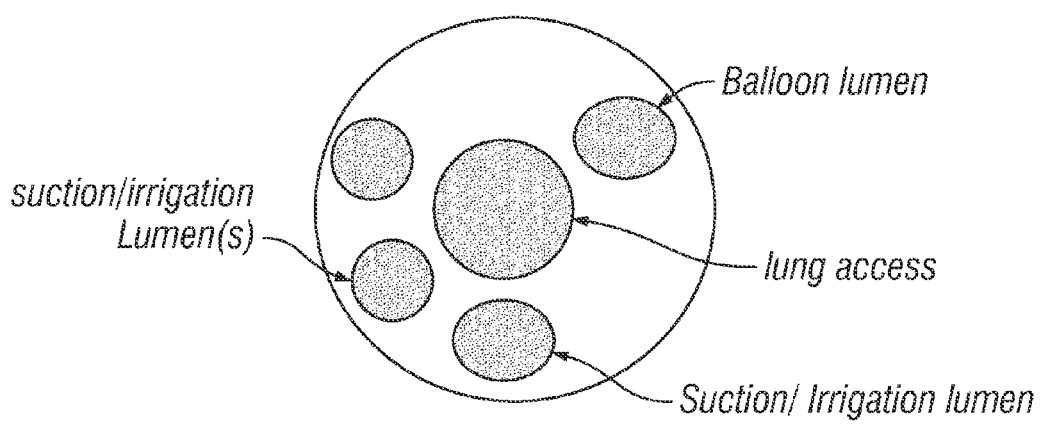

FIGS. 22A and 22B illustrate a simplified flushing system in which fluid is flushed via a multi-function tracheal tube. As shown in FIGS. 22A and 22B, fluid can be introduced via multi-function tracheal catheter 501, and enters trachea at port 502. Balloon 503 can restrict and/or prevent fluid entry into the lower trachea, while a primary lumen (not shown) allows entry and exit of respiratory gases. Flushing fluid can either overflow into stomach or can be recovered by application of suction to a lumen that is in fluid communication with port 502 or to an adjacent lumen in communication with another port in the vicinity of port 502.

Temperatures from various sites in, on, and/or near the body or the device can be used to adjust the function of the device while in use. These measurements can also be used to estimate properties that are not directly measured, such as deep tissue temperature (brain), cardiac output, core heat generation, brain heat generation and blood flow to the brain. Potential sites of temperature measurement include, for example, brain, rectum, esophagus, bladder, tympanic membrane, stomach, pulmonary artery, vena cava, aorta, exhaled gas, tracheal wall, eye, skin, peritoneum, axilla, and groin.

Exemplary cooling systems and related analyses are described below. A macroscopic heat balance on the patient's body is shown in Eq. 1 below.

$$\overline{\rho C_p} \frac{d\overline{T}}{dt} = q_{met} + q_{env} + q_{cooler} + q_{warmer} \quad (1)$$

The left hand side of the equation shows the total rate of change in heat content of the patient's body as the product of density, $\rho(x,y,z)$ heat capacity $C_p(x,y,z)$ and time derivative of temperature $T(x,y,z)$ represented by their spatial averages averaged over the entire body. The body's heat content changes in time as a result of multiple heat flows (measured in joules per unit time, i.e., watts). The first term on the right side of Eq. 1 is heat generated by the body itself, $q_{met}$, in ordinary situations, which is balanced by heat exchange with the body's environment, represented by the second term, $q_{env}$ at an equilibrium temperature of about 37° C. When a brain injured patient is cooled, additional heat is extracted by the cooling device, this heat flow, represented by $q_{cooler}$ will cause the patient's overall average temperature to decrease until a new equilibrium is established, with metabolic heating being balanced by environmental and device driven cooling.

The addition of thermal energy by use of a warming device such as such as a heated blanket, contact pads or wrap, can roughly counterbalance the energy extracted by the cooling device and lessen this overall decrease in patient temperature. The energy added by the warming equipment, $q_{warmer}$ will often be roughly equal in general (but not always exactly equal) to the cooling energy, $q_{cooler}$. In some cases, however the two energy flows will be very different, such as during induction of therapeutic hypothermia when a rapid reduction of patient brain temperature is required.

An advantage of this system is that, in some examples, it can permit care providers to selectively drive the brain to one temperature while driving the body to another temperature. This can be helpful because often the optimal therapeutic temperature for the brain is different than the optimal temperature for the body. For example, this can be the case when a brain injury results from cardiac arrest. This advantage can be highlighted by envisioning the head and body as two separate, but interacting systems as shown in FIGS. 9A and 9B.

Figure 9A:
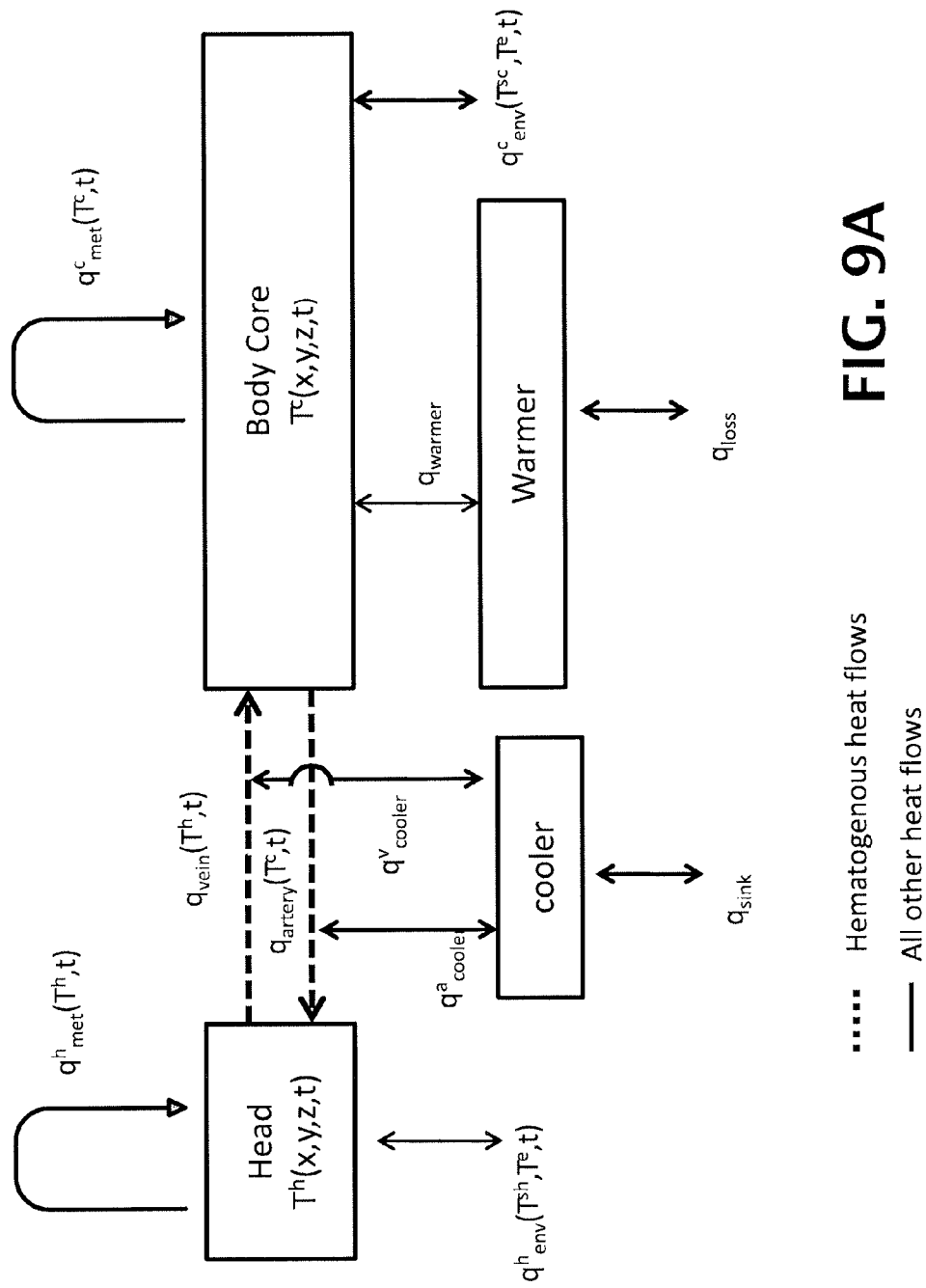
FIG. 9A is one example of a block diagram showing the heat flows impacting the temperature of the brain and body core for a system that can provide simultaneous brain cooling and body warming.
Figure 9B:
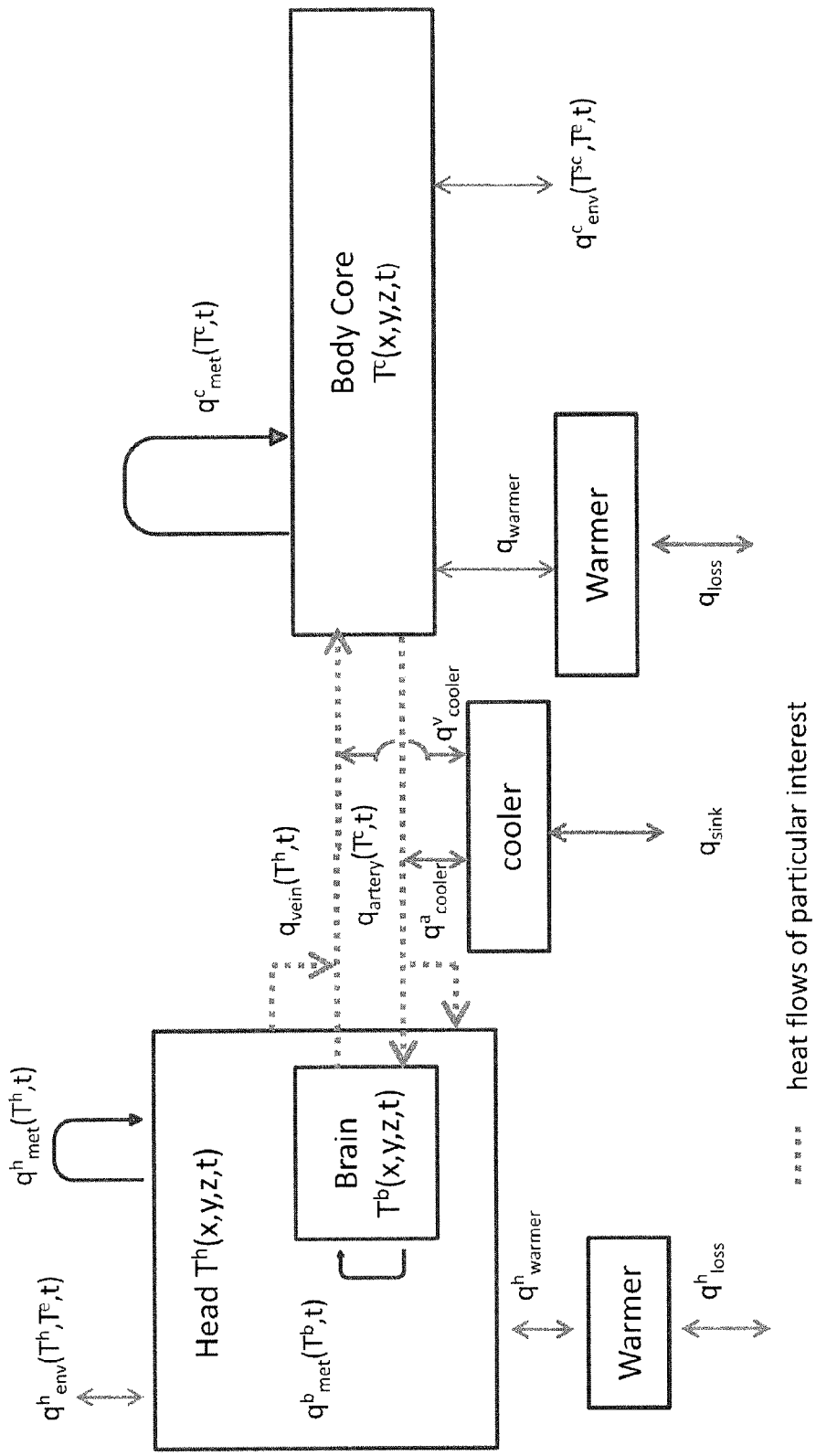
FIG. 9B is another example of a block diagram of heat flows impacting the temperature of the brain and body core.

FIG. 9A is a block diagram showing the major heat flows impacting the temperature of the brain and body core. The structure shown in FIG. 9A provides simultaneous brain cooling and body warming. FIG. 9B is a more detailed block diagram of the major heat flows impacting the temperature of the brain and body core. In this representation a third "head" compartment is added to emphasize that the cooling due to the arterial blood is not perfectly selective for the brain. However, the flows in the internal carotid and vertebral arteries do primarily influence brain temperature and other flows are influencing the brain indirectly after cooling the body.

In this model the "head" is considered separated from the body by a planar control surface at the end of the neck. There is of course a significant conductive heat exchange between the nasal cavity and the brain compartment. For this analysis it is lumped with the hematogenous cooling and treated as part of "q a cooler" and is not shown separately for the sake of brevity.

The heat balance on the head is given in Eq. 2, where quantities denoted with a superscript 'h' are total fluxes to and from the head. While recognizing that the temperature profile of the head is heterogeneous, this makes the point that the average temperature of the head can be manipulated by changing the energy content of the blood leaving the body core, $q_{artery}$, as is done with systemic cooling devices. However, in this case the blood energy flow is largely controlled by $q^a_{cooler}$, which the heat extracted from the artery by irrigation of the aerodigestive tract with cold fluid from the cooling unit. The temperature of the brain in turn affects the temperature of the exiting venous blood and thus the energy flux leaving the brain area toward the body, $q_{vein}$ $$\overline{\rho^h C_p^h} \frac{d\overline{T^h}}{dt} = q_{artery} + q^a_{cooler} + q^h_{met} + q^h_{env} - q_{vein} \quad (2)$$

The heat balance on the body core is given in equation 3 where quantities denoted with a superscript 'c' are totaled fluxes into the body core. While recognizing that the temperature profile of the body core is heterogeneous, the average temperature of the body core is impacted by the energy flow of the venous blood leaving the head, $q_{vein}$ which is in turn influenced by heat extracted from the veins due to proximity with the aerodigestive tract, $q^v_{cooler}$. The average temperature of the body core can also be manipulated through the use of an external warming device, and this heat flux, $q^c_{warmer}$ can provide a counter balance to the energy required to warm the returning cold venous blood.

$$\overline{\rho^c C_p^c} \frac{d\overline{T^c}}{dt} = -q_{artery} + q_{met}^c + q_{env}^c + q_{vein} + q_{cooler}^v + q_{warmer}^c \quad (3)$$

summing the metabolic heat generation of the body core and the head yields the total heat generation of the body $$q_{met}^h + q_{met}^c = q_{met} \quad (4)$$

By the same logic, $$q_{env}^h + q_{env}^c = q_{env} \quad (5)$$

And $$q_{cooler}^a + q_{cooler}^v \approx q_{cooler} \quad (6)$$

And finally, again using the same logic to describe the heat content of the entire body gives Eq. 7.

$$\overline{\rho^h C_p^h} \frac{d\overline{T^h}}{dt} + \overline{\rho^c C_p^c} \frac{d\overline{T^c}}{dt} = \overline{\rho C_p} \frac{d\overline{T}}{dt} \quad (7)$$

With these definitions in place adding Eq. 2 and Eq. 3 together recovers the original energy balance in Eq. 1. And shows how a stead state heat balance may be achieved Returning to Eq. 2, the heat balance on the head is re-arranged to group the terms describing the blood flow leaving the head and body core:

$$m^h \overline{C^h} \frac{d\overline{T^h}}{dt} = (q_{artery} - q_{vein}) + q_{cool}^h + q_{met}^h + q_{env}^h \quad (8)$$

$$m^c \overline{C^c} \frac{d\overline{T^c}}{dt} = (q_{vein} - q_{artery}) + q_{cool}^c + q_{met}^c + q_{env}^c + q_{warmer}^c \quad (9)$$

Solve for body equation for expression in parenthesis and substitute into brain equation $$(q_{artery} - q_{vein}) = \left[ -m^c \overline{C^c} \frac{d\overline{T^c}}{dt} + q_{cool}^c + q_{met}^c + q_{env}^c + q_{warmer}^c \right] \quad (10)$$

This makes combined expression relating change in head temperature to the change in body temperature. Note that the mass of the head is much less than that of the body, meaning that the change in head temperature will be much larger than the change in body temperature for a given amount of energy delivered $$m^h \overline{C^h} \frac{d\overline{T^h}}{dt} = \begin{bmatrix} -m^c \overline{C^c} \frac{d\overline{T^c}}{dt} + Q_{cool}^c + \\ q_{met}^c + q_{env}^c + q_w^c \end{bmatrix} + q_{cool}^h + q_{met}^h + q_{env}^h \quad (11)$$

In general the metabolic and environmental fluxes will be variable so these will be understood as unpredictable "load" variables. However, the cooler and warmer related fluxes can be readily manipulated by the user via an automated control system.

This analysis shows that the temperature of the brain and body can be manipulated independently, where $q_{cooler}$ is used to control the temperature of blood entering the head, and $q_{warmer}$ is essentially used to compensate for the resulting reduction in the temperature warmer is (and thus energy content) of the returning blood and thus decrease the resulting reduction in the patients core temperature. The inventors recognize that the model presented here is simplified in that conduction through the control surface was neglected, however it could be added in without significant change in the result, namely that cooling the aerodigestive tract affects brain temperature to a greater degree than systemic cooling strategies, and that the resulting disturbance on body temperature can be countered by systemic warming, and that the patient can be maintained in thermal equilibrium with the environment.

FIGS. 9A and 9B depict relevant heat fluxes, with the parameters in the above equations and FIGS. 9A and 9B described below in Table 7.

TABLE 7

(Summary of variables in heat balance FIGS. 9A and 9B, and Eqs. 1-11)

| Variable | Explanation | Note |
|---|---|---|
| $\overline{\rho}$ | density | |
| $\overline{C_p}$ | Heat capacity | |
| $\frac{dT}{dt}$ | Change in temperature in time | |
| $\frac{d\overline{T^h}}{dt}$ | Change in head temperature in time | |
| $\frac{d\overline{T^c}}{dt}$ | Change in body temperature in time | |
| $\frac{d\overline{T^b}}{dt}$ | Change in brain temperature in time | |
| $T^h$ | Temperature of the head, including the brain | Temperature profile is function of x, y, z position and t |
| $T^c$ | Temperature of the body core | Temperature profile is function of x, y, z position and t |
| $T^b$ | Temperature of the brain (excludes rest of head) | Temperature profile is function of x, y, z position and t |
| $T^{hs}$ | Head compartment surface temperature | Influences rate of head heat exchange with the environment |
| $T^{cs}$ | Core compartment surface temperature | Influences rate of core heat exchange with the environment |
| $q_{artery}$ | The heat flux transferred from the body core by arterial blood flow | Reflects a flow-weighted average of the heterogenous body temperature profile |
| $q_{vein}$ | The heat flux transferred from the head by returning venous blood flow | Reflects a flow weighted average of the heterogenous head temperature profile |
| $q_{cooler}^a$ | The heat flux removed from the arterial blood flow by the cold perivascular tissue | The arterial heat flux arriving in the head is $q_{artery} + q_{cooler}^a$ |
| $q_{cooler}^v$ | The heat flux removed from the venous blood flow by the cold perivascular tissue | The venous heat flux returning to the body core is $q_{vein} + q_{cooler}^v$ |
| $q_{met}^b$ | Heat generated by metabolism within the brain | |
| $q_{met}^h$ | Heat produced in the head by metabolim | |
| $q_{env}^h$ | Heat exchanged between the head and the environment | |

TABLE 7-continued (Summary of variables in heat balance FIGS. 9A and 9B, and Eqs. 1-11)

| Variable | Explanation | Note |
| --- | --- | --- |
| $q_{met}^{c}$ | Heat produced in the core by metabolism | |
| $q_{env}^{c}$ | Heat exchanged between the core and the environment | |
| $q_{warmer}^{c}$ | Heat supplied to the body by the warmer | |
| $q_{warmer}^{h}$ | Heat supplied to the head by warming | Heat designed to counterbalance cold blood arriving in the external carotid arteries. |
| $q_{sink}$ | Heat removed from the warm side of the cooling device | In the case a thermoelectric cooler is used this includes heat generated by the device as well as heat pumped from the cold side of the device |
| $q_{loss}^{c}$ | Heat that the warming device loses to the environment rather than supplying to the patient | In some examples, this can be a significant amount of heat relative to that actually delivered to the patient |
| $q_{loss}^{h}$ | Heat that the head warming device loses to the environment rather than supplying to the patient | In some examples, this can be a significant amount of heat relative to that actually delivered to the patient |

Figure 10A:
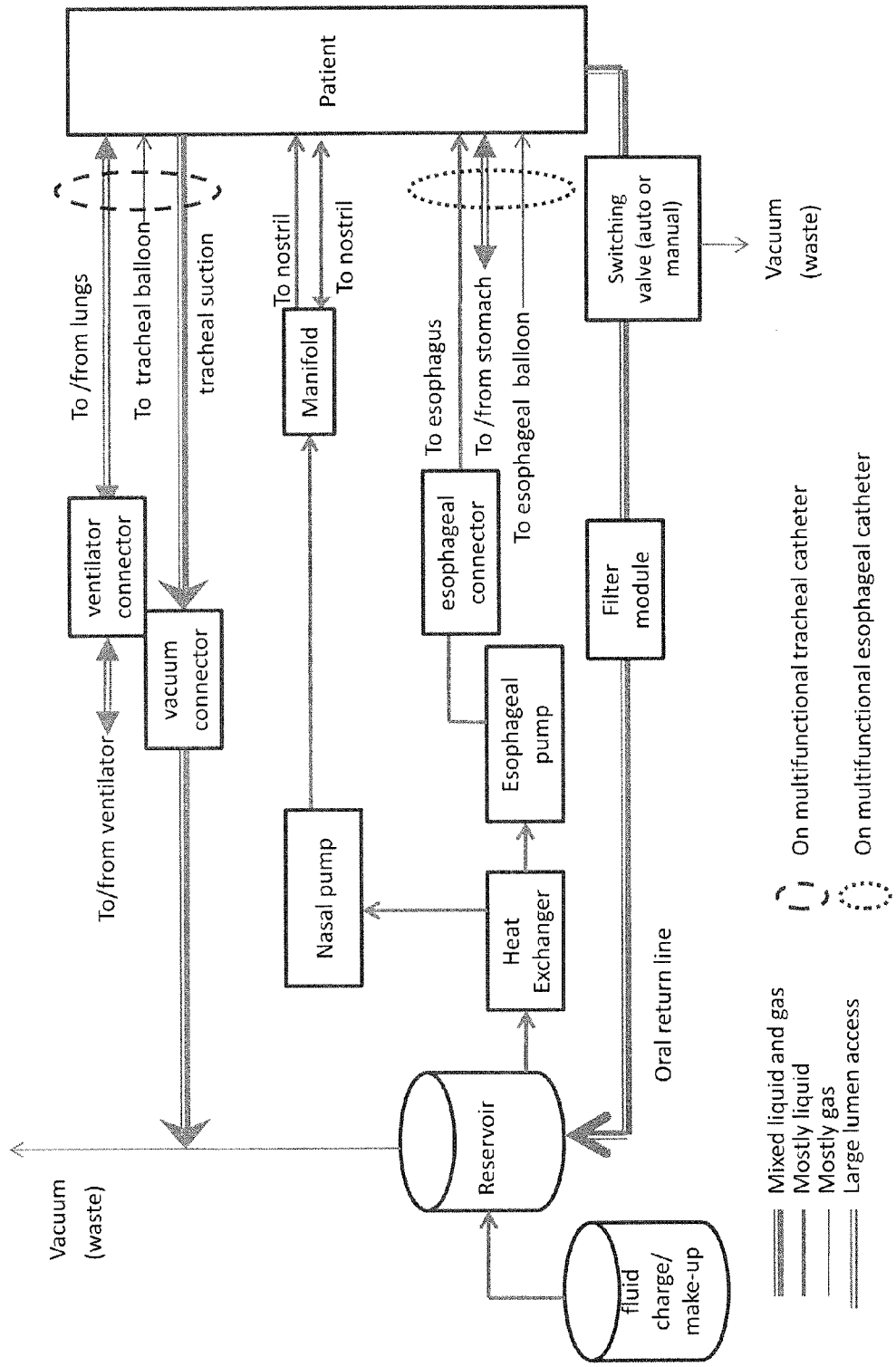
FIG. 10A is an example of a block diagram showing a fluidic system used to accomplish patient cooling.
Figure 10B:
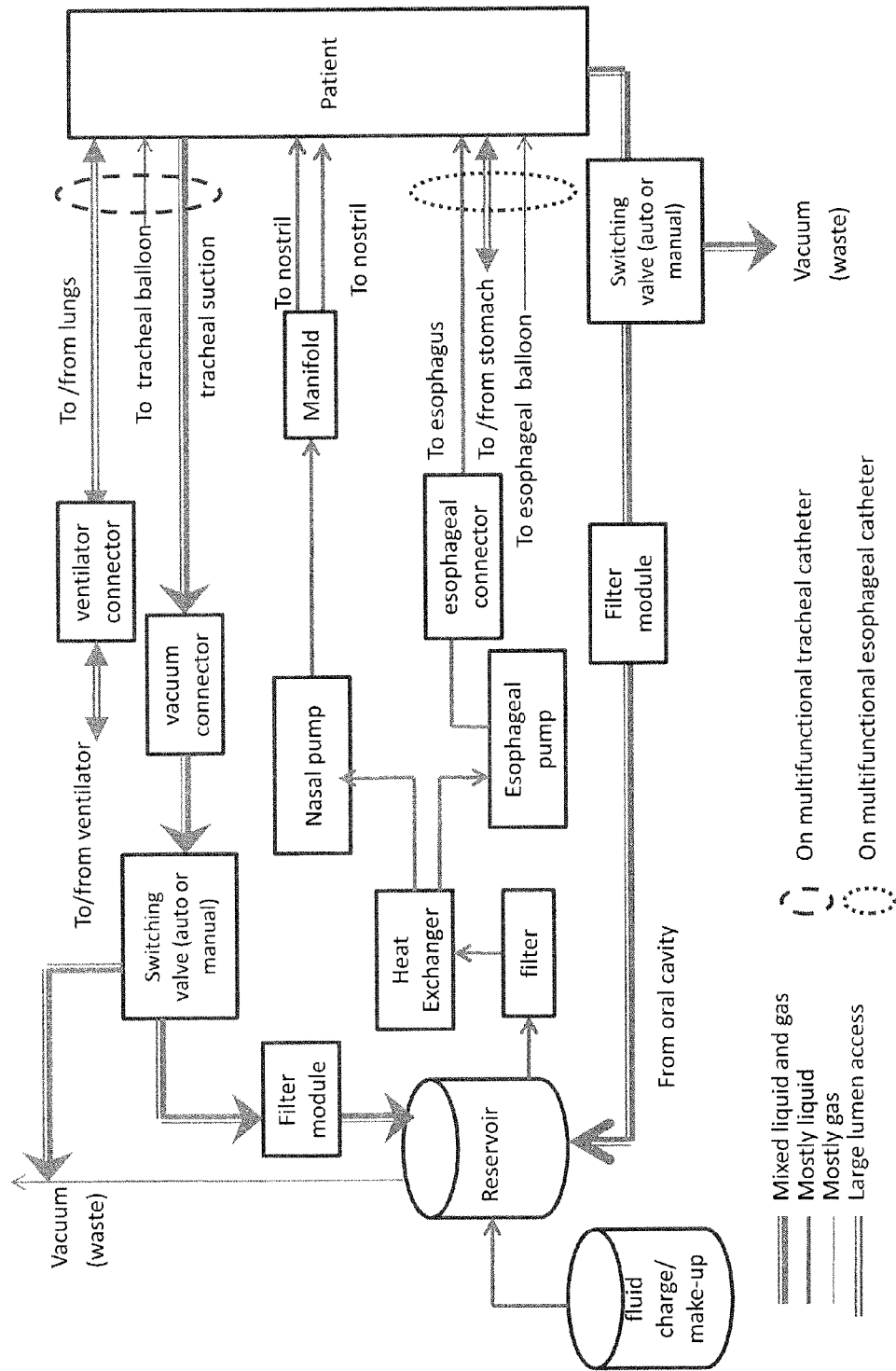
FIG. 10B is another example of a block diagram of a cooling system.
Figure 10C:
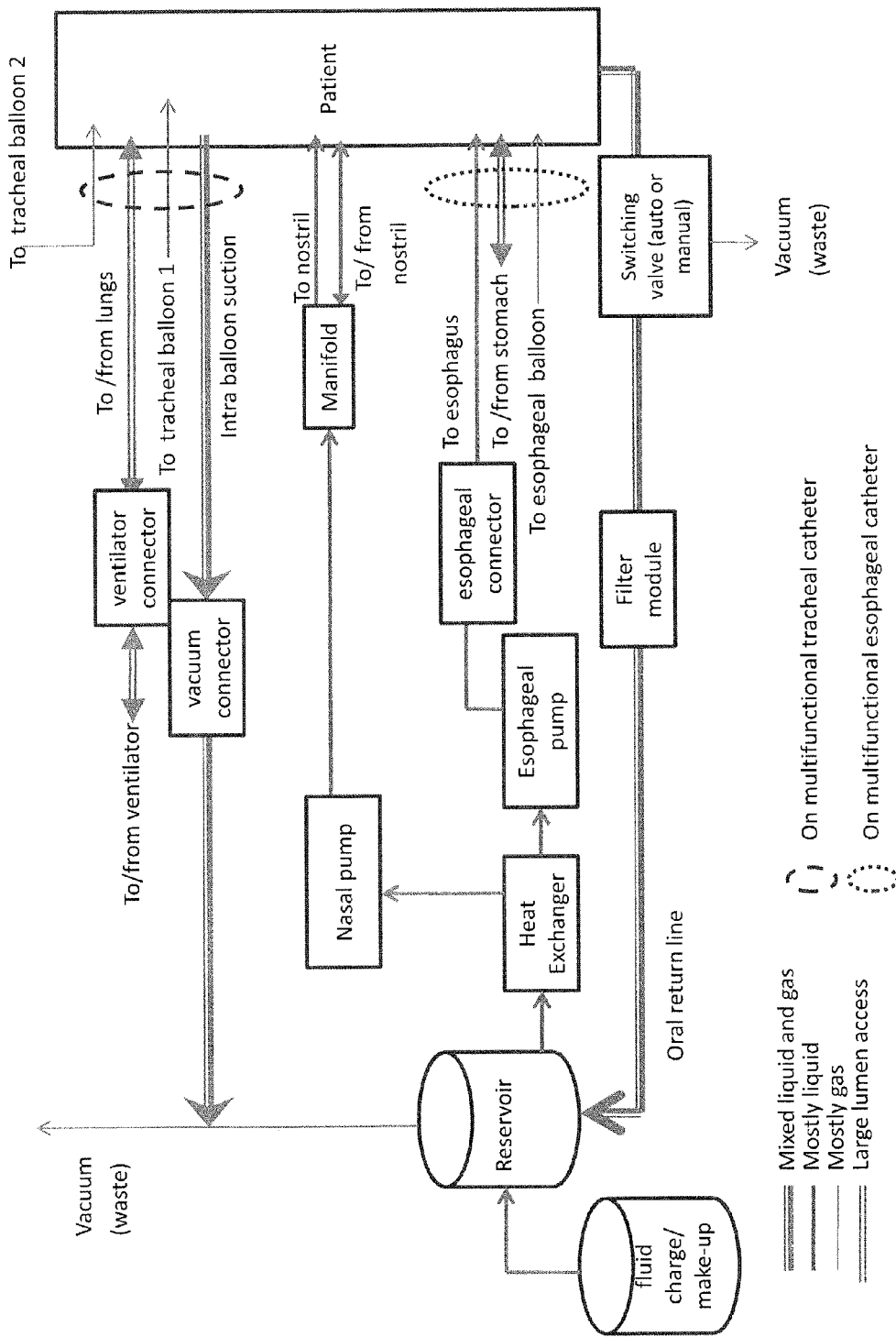
FIG. 10C is yet another example of a block diagram of a cooling system.

FIGS. 10A and 10B illustrate exemplary fluid (liquid, gas, and mixed) flow in the system. The esophageal and nasal catheters are supplied with cold fluid in the manner shown. The fluid is pulled from the reservoir by the pumps and cooled by the heat exchanger in thermal contact with the cooling unit. Fluid is removed from the patient by vacuum, but could also be pumped away. Fluid flow could also be reversed to empty the patient's aerodigestive tract at any time.

Further variants could feature the elimination of the separate oral return line by using a lumen of either or both of the tracheal and esophageal catheters, or extending one of the nasal catheters to the oropharynx and employing it as a return line. In such a case, the other nasal catheter can still be used for irrigation of the nasal cavity.

In use, an initial fluid charge can be supplied to the reservoir the reservoir has a volume of about 2-20 L and is kept under a vacuum typical of that used in hospitals. The vacuum can be generated by a vacuum pump included in the unit, or by attaching to an externally supplied vacuum, such as the house vacuum line. The fluid can be drawn from the reservoir through the disposable heat exchanger by the nasal pump and the esophageal pump. The pumps can be peristaltic pumps and can be configured to move fluid toward the nasal area and esophagus respectively. Because the lines can be cold as a result of the fluid inside, the lines that are outside the patient can be insulated to reduce condensation if desired.

In the example shown in FIG. 10A, flow from the nasal pumps is split (e.g., generally evenly) by a manifold and supplied to two catheters that are each inserted through one of the patients nostrils. This fluid irrigates the nasal cavity. In other examples, however, the irrigating fluid can be delivered by only one of the nasal catheters and the other catheter can be routed, for example, to vacuum and used as a return line. The esophageal pump shown in FIG. 10A is configured to move fluid into the body via a lumen of the multifunctional esophageal catheter. It should be noted that the fluid in the patient is roughly at atmospheric pressure because the patient's mouth and possibly nasal cavities are open to the atmosphere. Thus, this cooling system enjoys a substantial safety advantage over intravascular systems where the cooling fluid is at very high pressure. Because the fluid in the patient is very near atmospheric pressure, the vacuum of the reservoir or the waste line/container is sufficient to remove the fluid from the patient.

In this example embodiment, fluid introduced into the patient can be recovered primarily by the oral return line. As shown in FIG. 10A, the oral return line can include a switching valve that can be manually actuated in some embodiments and automatically actuated in others. The switching valve can be, for example, a three way valve, a disposable stopcock or ball valve, or a pair of pinch valves. In one example, the valve or valves is/are disposable.

If the fluid is not discarded, it can be filtered by a filter or series of filters (a filter module) before returning to the reservoir for recirculation. Additional fluid may be added to the reservoir at any time to replace losses due to spills, discard, etc. Fluid can be recovered from the patient by suctioning through the multifunctional tracheal catheter. This fluid may be re-circulated or it can be routed to waste.

Fluid can also be recovered from the patient by reversing either or both of the esophageal or nasal pumps by connecting the esophageal and nasal tubes to vacuum line Fluid can be circulated through this system as needed to modulate patient temperature. The system can be stopped when cooling is not needed. In general, a flow rate and temperature are selected for the irrigating fluid, and the amount of cooling is determined by the fraction of time the pumps are on or off (i.e., the duty cycle). However, other modulation of flow rate and/or temperature can be used to control the amount of cooling provided to the patient.

Care is desirably taken to avoid suctioning trauma to the patient's tissues, and suction lumens typically have multiple holes in line (like a whistle catheter) or even distributed at different points around the multifunctional catheter's circumference so that they are not all blocked simultaneously. For more even circulation, multiple holes or lumens may be added to the esophageal or nasal catheters.

As described above, FIG. 11 shows a flow field of fluid inside the patient during use. The temperature modulating fluid is supplied through nasal catheter 401 and multi lumen esophageal catheter 402. Esophageal fluid exits into esophagus through port 403 while the stomach is protected with balloon 404. Balloon 404 also prevents aspiration of stomach contents. Large lumen catheter 405 preserves stomach access, and provides exit path for emesis. Distal trachea 406 is protected by balloon 408 and port 409 allows removal of fluid, preventing stagnation. The oral catheter functions as a main exit line 410 and recovers fluid for filtering and recirculation or disposal. Suction through tracheal suction port 409 (note 409 may actually be multiple ports) is used to withdraw fluid from the trachea when desired. This has the beneficial effect of flushing the trachea and reducing potential for bacterial growth by reducing the "residence time" of fluid above the cuff protecting the lungs. Alternatively, if flushing without cooling is desired, the fluid can be made normothermic by reversing the polarity on the thermoelectric device(s), causing them to function as warmers rather than coolers.

Figure 12:
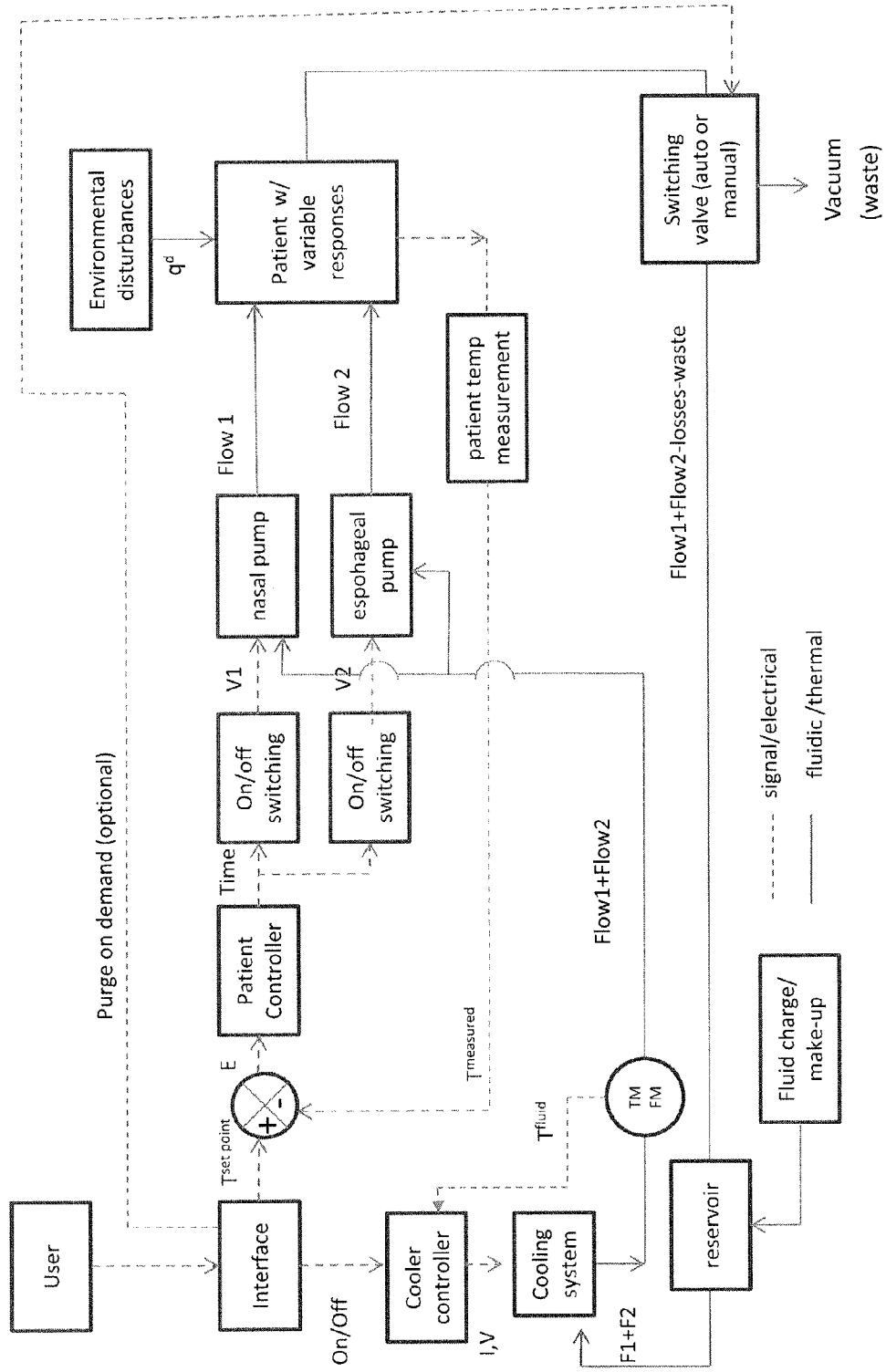
FIG. 12 is an example of a block diagram of a control system used to manipulate patient temperature and irrigation flow rates, among other things. Dashed lines represent interaction via information or electrical signals, while solid lines represent thermal and fluidic interactions.

FIG. 12 illustrates an exemplary control system that can be used to allow automated maintenance of desired set points for the patient's body core, as inferred from measured rectal or other temperature measurements, and/or brain, as inferred from direct measurement via trans-cranial bolt, or by a model informed by one or more measurements that do not invade the brain. The control system can also enable cooling of the patient to a given set point with minimal "overcooling" and enable controlled re-warming. This can be accomplished with PID control with parameters obtained empirically, by measurement of the patient, or by mathematical model.

The control system can comprise one or more of the following: a temperature measurement probe, a means of transmission for temperature data to the control unit, a means accepting user input, a control unit, and a means of transmitting the control unit output to a final control element (e.g., actuator).

In one example, a simple on-off feedback control scheme is provided to cool the brain while keeping the patient's core temperature above a certain minimum (e.g., a lower control limit, LCL). The measured and controlled variable can be, for example, a patient's rectal temperature. The cooling unit can be set by the user to provide fluid of a programmed temperature in the vicinity −20° C. to 37° C. The pumps can be set by the user to provide a flow rate between, e.g., 0.2 and 10 l/min when active. Once these parameters are fixed, patient temperature can be modulated by manipulation of the flow rate (on/off) of irrigation of all or part of the aerodigestive tract. A second control loop may be used to control the action of the thermoelectric cooling device(s), such that irrigation fluid is provided at the flow rate and temperature desired. The power to the cooler (e.g., thermoelectric or other) can be modulated to keep the irrigation fluid cold, but not freezing for example about 2-4 C. This second control loop can be a traditional PID controller. The desired set point for the irrigation fluid can be between −20° C. to 37° C. depending on the fluid used and the particular situation, but the fluid temperature set point is generally chosen at the start of therapy and kept under control, as opposed to being manipulated to control patient temperature. This approach minimizes the duty cycle on the pumps and minimizes the amount of time that the patient's aerodigestive tract is irrigated. When the patient core temperature reaches the lower control limit LCL, the pumps are switched off and kept off until the patients temperature rises above the upper control limit, or UCL, and cooling is resumed. In some cases it will be desirable to reverse the pumps and remove any recoverable fluid from the patient's aerodigestive tract at the end of the cooling action.

In another example, a control scheme can employs a PID controller for the patient temperature as well. This system can be configured to keep the patient's core temperature within the vicinity of a user programmed set point. The set point may be changed by the user (i.e., care provider) at any time. The user can also change the set point in a gradual fashion (a ramp rate), which can be useful to control the speed of cooling or re-warming. Patient temperature can be modulated by manipulation of the flow rate (on/off) of irrigation of all or part of the aerodigestive tract, and the patient's own metabolism provides a counterbalancing warming force. The irrigation time required of the pump(s) can be calculated by the PID control. The block diagram of FIG. 12 illustrates an exemplary method of implementing this system.

FIG. 12 illustrates interactions between components to enable feedback control. A user can interact with a user interface, with the user commanding set point and ramp rate temperature for the patient (shown as $T_{set\ point}$). The user can designate a temperature for the irrigation fluid, which is compared against the measured temperature of the fluid leaving the heat exchanger, $T_{fluid}$. Measurements may be taken at several points along the heat exchanger to provide more information about the temperature profile across the heat exchanger. The cooler controller manipulates power to the cooling system, represented by I,V (current and voltage) and, working as a feedback controller, maintains the temperature of the fluid leaving the cooling system at the desired temperature. The patient controller then works to drive the patient temperature, $T_{measured}$, to the desired temperature at the desired rate by turning the irrigation pumps on and off when indicated by the difference between patient temperature and set point, represented by the error signal, E.

The signals to the pumps V1 and V2 can be varied if different pump speeds are desired. Or, V1 and V2 may be simple "on/off" signals. The switching valve can be used to discard the fluid leaving the patient or recirculate it. It is expected that the pumps will be switched on not only to cool the patient initially, but to maintain the patient at the desired temperature in spite of environmental and metabolic heat generation, which acts as a disturbance or load on the patient (shown as qd). Note TM and FM are optional temperature and flow measurement devices respectively. A variety of temperature and flow measuring devices may be used, but if the heat exchanger is of sufficient dimensionless length—described earlier, the temperature of the fluid entering the patient may be readily inferred. Consideration of the power supplied by the thermoelectric unit and warming unit (if used) can be used as the basis of an estimate of energy flux to/from the patient Simultaneous cooling and counter warming can provide significant advantages. To illustrate these advantages, the flow field in the aerodigestive tract can be characterized and the resulting rates of heat transfer into the cold fluid can be estimated. First, the flow can be characterized as laminar or turbulent. Putting in the physical properties for water gives a Reynolds number of about 200 this flow is laminar. Taking a Prandtl number of 13 for water allows calculation of a Nusslet number of about 15 which implies a convective heat transfer coefficient of about 440 w/m2K for the "plate." Assuming a more cylindrical geometry yields a slightly different answer a Re of about 350, and a Nusslet number of about 15, leading to a convective heat transfer coefficient of about 300 W/m2k. Taking a mid-range value between the two cases gives a convective h of 400 W/m2k. This convective transfer is in series with the heat transfer resistance of the perivascular tissue that separates the airway from the arteries of interest. Assuming an average distance of about 1.5 cm of tissue in this area gives an overall heat transfer coefficient of about 35 w/m2K by:

$$Q = \frac{1}{\frac{1}{h} + \frac{l}{k}} A \Delta T.$$

For reference, if the heat transfer through the tissue side were infinitely fast, heat transfer would be about 10× faster. Accordingly, since the heat transfer resistance through the tissue is much larger than the resistance within the fluid filled airway, maximizing the surface area used for heat exchange, A, in the above expression as well as the temperature gradient, ΔT provide greater effects than maximizing flow rate of cooling fluid once a certain minimum flow rate is reached about 1 to 10 l/min. Also, decreasing the length scale, 1, over which conductive rather than convective heat transfer takes place can be significant. With this in mind, devices that use a balloon with re-circulating cold fluid, such as US 2009/0177258 and U.S. Pat. No. 7,189,253 can be disadvantageous because the cooling fluid is constrained by the balloon and cannot make the same intimate contact with the irregularly shaped features of the pharynx or esophagus as is possible with a free flowing fluid approach, as disclosed herein. This decreases both A, the area available for heat exchange and critically increases l by adding the thermal resistance of the balloon, and creating "dead spots" where convection cannot sweep away the thermal boundary layer. Air in these "dead spots" can further retard heat exchange due to air's low thermal conductivity.

A similar analysis can be made for the esophagus with the flow considered to be laminar in most cases. Again, tissue side resistance is greater than the heat transfer resistance on the fluid side. Given the close proximity of the esophagus and lower pharynx to the carotid, exploiting the esophagus and the nasopharynx together increases the surface area and column length available for heat exchange in the region of the body that the vertebral and carotid arteries traverse.

An additional point of differentiation versus nasal focused cooling strategies is apparent when the heat exchange between the perivascular tissue and the arteries is examined, with the carotid and vertebral arteries being of particular interest. Assuming a roughly circular cross section for the artery and a radius of about 4 mm, a Reynolds number of about 400 is computed. Using a Prandtl number of about 20 to represent blood, a Nusslet number of about 10 can be computed with the following analysis:

$$\overline{Nu}(L) = 1.614 \left( \frac{\frac{L}{D}}{PrRe} \right)^{-1/3}.$$

It is then possible to determine the extent to which the warm blood entering the carotid at the aortic arch will equilibrate with the cold tissue surrounding it by the time it reaches the circle of Willis in the brain. The expression for the degree of equilibration can be presented as:

$$\frac{\overline{T}_{artery} - T_r}{T_i - T_r} = e^{-A \frac{NuZ}{Re*PrD}}.$$

Using the representative numbers above in the expression reveals that the arterial blood is incompletely equilibrated even after 20 cm of travel in the carotid artery. This result shows that maximizing the length of the "cold zone" of perivascular tissue can be significant, and that exploiting the esophagus in tandem with the nasopharynx allows the blood to be cooled more thoroughly than is possible with "nasal only" strategies that cool the upper pharynx alone and therefore a shorter segment of the carotid and vertebral arteries.

Figure 13:
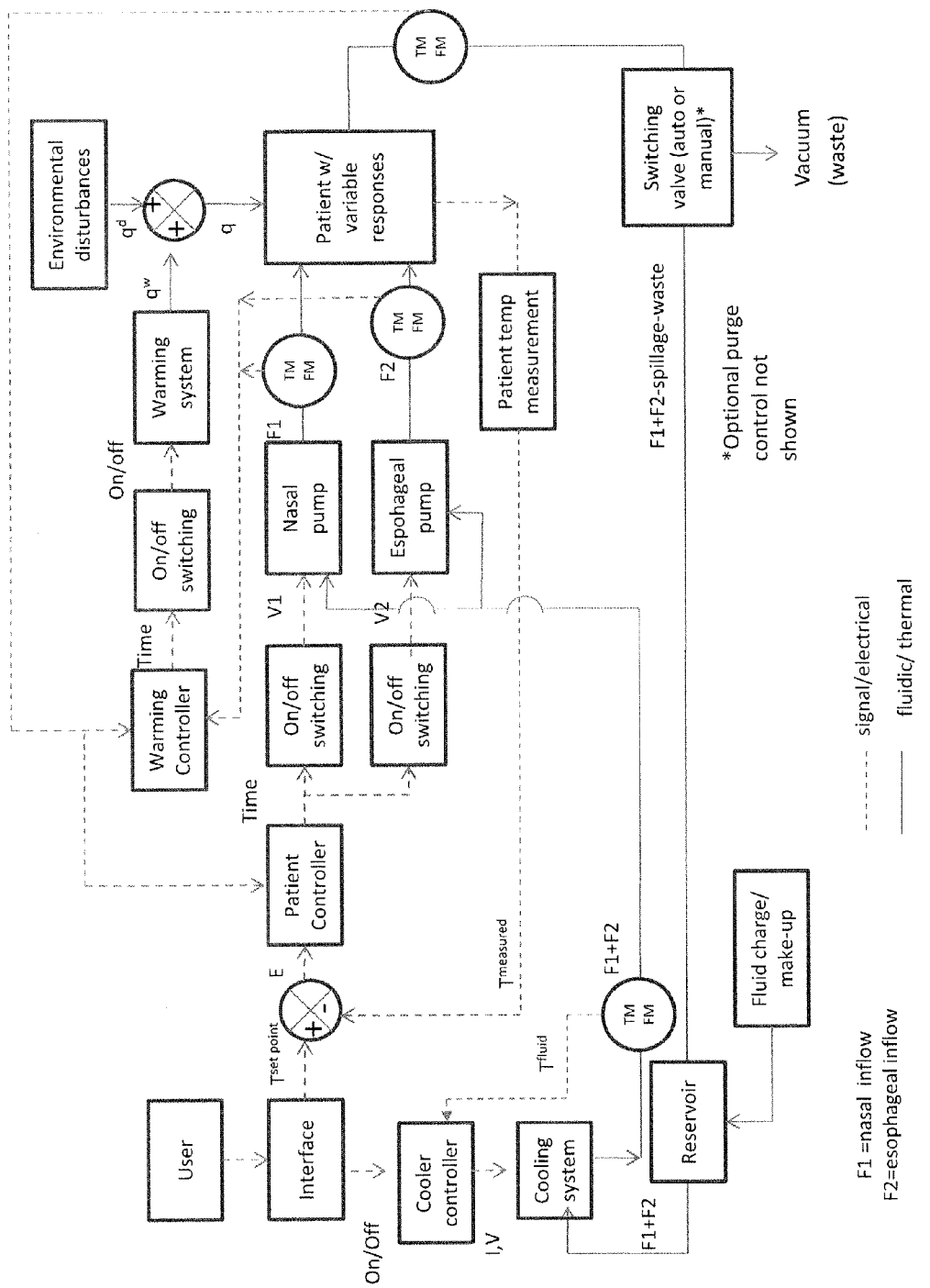
FIG. 13 is another example of a block diagram of a patient temperature control system when an integrated warming device is used. Dashed lines represent interaction via information or electrical signals, while solid lines represent thermal and fluidic interactions.
Figure 14:
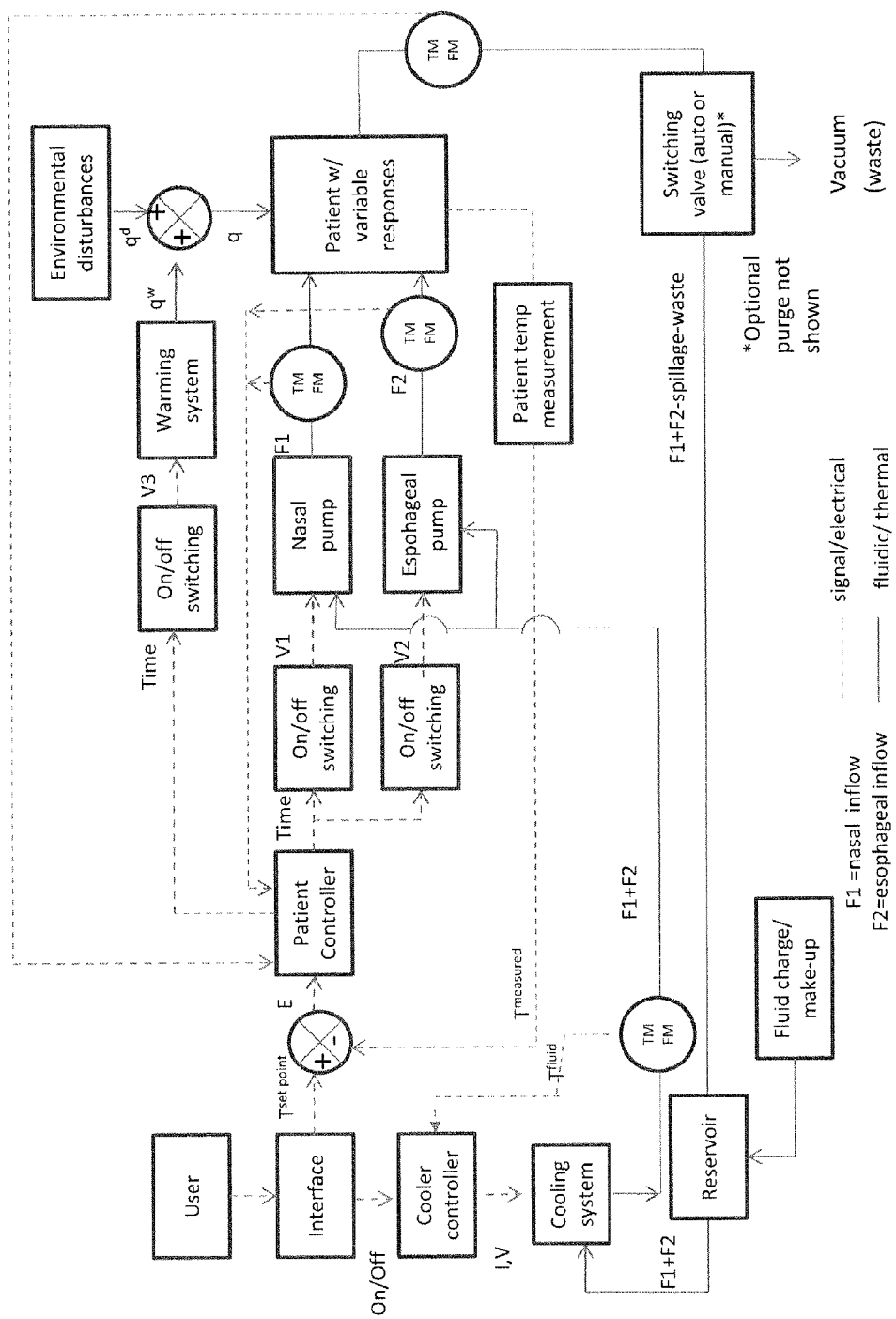
FIG. 14 is yet another example of a block diagram of another patient temperature control system.

FIGS. 13 and 14 illustrate methods of combining cooling of the brain with warming of the core. Frequently, it will be desired to warm all or part of the patient's body to counteract the effects on the body core of cold venous blood returning from the cooled brain or blood cooled by heat exchange with the aerodigestive tract while passing through the jugular vein. This counter warming can be applied to maintain a balance on the heat flows coming into and out of the patient. Counter warming additionally permits a greater brain to body core temperature gradient. Such an effect can operate to reduce the metabolism of the brain temperature, leading to reduced heat production by the brain.

The present disclosure includes various counter warming methods and devices. For example, in some embodiments, the system can be configured to comprise palm and/or sole counter warming devices for the hands and feet, respectively. Palms and soles participate actively in heat exchange. Such palm and/or sole counter warming devices can be used in addition to or independently from other warming devices (e.g., hot air blankets, water blankets, etc.). Palm and/or sole counter warming devices can have numerous benefits, including, for example, permitting maximum access to a patient during a cooling procedures (e.g., when a hot air blanket is not used with the palm and/or sole counter warming devices). Further beneficial effects can include vasodilation of the palms and/or soles upon warming the posterior neck, which can lead to additional core warming.

In other embodiments, the devices and methods can comprise a water blanket configured to warm the patient (e.g., an insulated water blanket). A water blanket can be used in tandem with or independently from other warming devices (e.g., palm and/or sole warming devices). In addition to their warming abilities, water blankets can further assist in gathering data for the system, such as by measuring fluid temperature into and out of the blanket to gauge a subject's core temperature (e.g., or at least the temperature of those portions of the subject in contact with the water blanket) or by using resistive heating of a defined power and temperature. Other blankets to assist in maintaining and/or increasing the body core temperature of a subject during a brain cooling procedure are, for example, foil blankets (e.g., space blankets). Furthermore, forced air devices can also be used (e.g., "Bair Hugger" Therapy blankets, etc.).

Other embodiments can include warming devices configured for other areas of the body. For example, some counter warming devices include passing warmed air into the lungs (e.g., through a tracheal tube discussed above). Further, venous warming devices can be used (e.g., jugular bulbs) to warm veins (e.g., depending on a given procedure, a given point in the procedure, a desired brain to body core gradient, etc.).

Counter warming methods can be performed using one or more of the counter warming devices and systems discussed in this disclosure. A warming device, a combination of warming devices, and/or the warming location can be varied during a procedure, depending on a core temperature measurement, a given procedure, a given point in a procedure, a desired brain to body core temperature gradient, and the like.

At the end of a cooling cycle, a patient can be re-warmed in a controlled fashion. As an example, warming can be adjusted to maintain a patient's body core temperature above a desired level (e.g., 33° C. to 40° C.). A patient can be warmed at any desired rate. For example, a user can decrease cooling fluid (e.g., form 100% to 0%) over a period of time (e.g., 12 hours), and counter warming can be adjusted during this time period as well.

These "steady state gradient" methods can provide additional advantages. For example, neuroprotection can be achieved by the cooling of the brain while complications related to body cooling can be reduced and/or avoided by taking into consideration the overall heat balance on the patient and returning heat to the patient's core. This gradient may be maintained for as long as it is therapeutically beneficial. The exploitation of the pharynx and esophagus is to create a long cooling zone around the arteries enables a large gradient between the brain and the body to a degree not possible with other approaches.

To create the gradient between brain temperature and body temperature, the aerodigestive tract can be cooled by irrigation, while the body is warmed with external warming devices, such as a warming helmet, pads or warming blanket on the body core or extremities. Heat lamps or warmed IV fluids could also be used. The warming devices should not cause the skin to reach temperatures of more than about 42° C. to reduce a risk of burning the patient. In one example, warming devices can be configured to provide a very mild temperature gradient (about 2-7° C. above the body core) over a large surface area of the patient.

If a stable difference between brain and body temperature is desired, a steady state can be achieved by adjusting the duty cycle of the warming devices to compensate for the heat removed by the irrigation of the aerodigestive tract, while maintaining the temperature of the warming devices strictly below the temperature range likely to cause skin damage (approximately 42° C.).

FIG. 13 shows an exemplary arrangement for accomplishing this aim, where measurements of flow rates and temperatures of fluids entering the patient are compared with the flow rate and temperature of fluid leaving the patient to infer the total amount of heat being extracted by the system. This measurement can be used alone or in combination with a measurement of power delivered to the cooling device. FIG. 13 is a representative block diagram of the patient temperature control system when an integrated warming device is used. In this embodiment, energy sent to the warming device can be modulated based on heat removed from the patient but the control can also be informed by rate of temperature change, patient size or weight, or mathematical models. The warming heat can cancel much of the cooling of the body core by warming cold venous blood returning to the heart. The warming system has in internal warming controller that can be set to about 40-42° C. but not higher to avoid damage to the skin. Although only one warming device is shown in FIG. 13, more than one warming device can be used if desired. The amount of warming can be modulated by adjusting the "duty cycle" (e.g., by adjusting the amount of warming per hour with a simple on/off signal or variable voltage).

FIG. 14 shows another exemplary integrated control strategy. FIG. 14 is a representative block diagram of an embodiment where energy sent to the warming device can be modulated based on heat removed from the patient as well as the patient's core temperature. The control scheme can include other factors as well, including, for example, power to the cooling unit, rate of patient temperature change, patient size or weight or mathematical models.

In this configuration shown in FIG. 14, the temperature and flow rate measurements on incoming and outgoing fluids are optional. Irrigation is started to provide a base "cooling load" and rectal temperature is monitored. When the rectal temperature goes below a given threshold, the warming devices can be energized and rise to a target "skin temperature" of a few degrees (e.g., 2-7° C.) above the desired patient core temperature. The warming devices can be controlled by PID controllers to hold a safe set point skin temperature, and then turned on/off as needed to maintain the patient core temperature in the desired range or into the vicinity of the desired set point. In this manner the body core can be held in a substantially normothermic state, while the brain can be continuously perfused with cooled blood. The cold blood branching off into the external carotid can optionally be re-warmed directly with the warming helmet, while the cold blood returning in the jugular vein can be counteracted with systemic warming measures such as a warming blanket, to warm any or all of the face, scalp, neck posterior or warmed gasses that are directed into the lungs via a ventilator.

PID control loops of the body core temperature can be envisioned where the irrigation time (duty cycle) of the cooling pumps and the active warming time (duty cycle) of the warming blanket are the parameters modulated to keep the core body temperature close to the desired steady state set point. The same control system could warm or cool the body core at a given ramp rate by making several small step wise changes to the core temperature set point.

This system could also be used in a "maximum gradient" mode. Such a method for establishing and maintaining a maximal gradient between brain and body core temperature can include one or more of the following steps:

1. Commencing cooling of the patient's aerodigestive tract with an apparatus as described herein. Exploiting the entire aerodigestive tract can be particularly useful when paired with systemic warming as the blood leaves the aortic arch at a temperature representative of the body core. Thus, the ultimate depth of brain cooling can be largely determined by the amount of heat that can be extracted from the blood on its journey from the aortic arch to the circle of Willis. If the length of the "cold zone" is not maximized—such as in a "nasal only" cooling strategy—the residence time of the blood in the cooling zone will be reduced, and the brain will be chilled less deeply before the blood returns to the body core and is re-warmed.
2. Controlling the temperature of the irrigating fluid to the lowest temperature that does not damage the aerodigestive tract (e.g., between about −20° C. and 20° C.).
3. Continuously or nearly continuously providing a flow rate of liquid to the aerodigestive tract sufficient that the overall rate of heat transfer is relatively insensitive to variations in flow rate. Providing flow sufficient such that the controlling resistance to heat transfer is not convective exchange between the patient and the irrigating fluid (e.g., about 0.2-10 l/min).
4. Controlling the temperature of the surface warming devices to not exceed about 40-42° C.
5. Applying the warming devices to the patient to warm the surface (skin) of the patient.

The warming device can comprise, for example, one or more of a warming blanket, warming helmet, warming of the face or neck posteriors(a maximum surface area is preferred when a maximum gradient between brain and body is desired).

6. Controlling patient core temperature by activating the warming system frequently enough that the patient's core temperature as determined by rectal and or other measurements is roughly maintained normothermic (e.g., around 37° C., or for deepest brain cooling, at least above the temperatures at which complications arising from systemic cooling begin to appear (e.g., about 32° C.).
7. Maximizing the duty cycle of the cooling pumps by, for example, maintaining continuous or nearly continuous irrigation of the aerodigestive tract with cold fluid.

Reducing the duty cycle of the pumps (irrigation time per day for example) would reduce the depth of brain cooling and thus the amount of counter warming needed. In this way, a steady state gradient can be set to any arbitrary value between the maximum case and an un-cooled one.

Other control systems can be provided. The warming function will often lag the cooling function, as the body core temperature takes some time to respond to the irrigation of the aerodigestive tract. The warming can include, for example, an element of feed forward control where the warming function is activated based on heat removed, and thus warming the body core before the patients core temperature drops appreciably. The start of warming could be based on the heat extracted from the patient as determined from measurements of incoming and outgoing irrigation fluid temperature. This quantity could be used independently or in combination with temperature measurement data to determine the correct control actions in the manner shown in FIG. 13.

This system could also be used in a "maximum selectivity" mode, where the ratio of brain cooling to systemic cooling is maximized. The term "maximized" as used herein, refers to an increase in a ratio to a point that is at or near a maximum. The term should be understood to include ratios whereby systemic cooling is less than an actual maximum ratio. This method can be used to establish and maintain a significant gradient between brain and body core temperature with minimal power expenditure. Such a method can also be used if limited cooling power or cooling fluid is available (such as in a field hospital) or if access to the esophagus is difficult or otherwise restricted. The method can also reduce the need for counter warming. In one embodiment, the method can include one or more of the following steps:

1. Commencing cooling of the patient's upper airway with an apparatus as described herein in other embodiments. The esophageal tube is not used, and the esophagus is not actively exploited for cooling. A laryngeal mask, extended oral catheter, or Trendelenberg posture can be used to reduce fluid entry into the esophagus. Because the length of the "cold zone" is not maximized—the residence time of the blood in the cooling zone will be reduced, and the brain will be chilled less deeply before the blood returns to the body core and is re-warmed. However, power and fluid requirements are reduced and selective cooling is still achieved.
2. Controlling the temperature of the irrigating fluid to the lowest temperature that does not damage the aerodigestive tract (e.g., between about −20° C. and 20° C.).
3. Controlling the level of fluid in the patients mouth by occasional adjustment of the flow rate in the oral catheter/return line. This allows maximal fluid recovery and even adjustment of cooling rate/selectivity by incomplete wetting of the pharynx.
4. Intermittently providing cooled liquid to the upper airway sufficient that such that the controlling resistance to heat transfer is not convective exchange between the patient and the irrigating fluid (e.g., about 0.2-5 l/min).
5. If a warming device is used (optional because of low cooling power) Controlling the temperature of the surface warming devices to not exceed about 40-42° C.
6. Optionally applying the warming devices to the patient to warm the surface (skin) of the patient. The warming device can comprise, for example, one or more of a warming blanket, warming helmet, warming of the face or neck posteriors(a maximum surface area is preferred when a maximum gradient between brain and body is desired).

The "maximum selectivity" method is differentiated from the method of rapid brain cooling using naso-oro perfusion and head immersion in dogs described by White et al. ("Rapid Selective Brain-Cooling using Head Immersion and Naso-Oral Perfusion in Dogs, Resuscitation 10:189-191, 1983), in that it does not immerse the subject's head. Avoiding head immersion can provide improved cooling selectivity. Selectivity is improved because the brain is convectively shielded from surface cooling of the face and scalp, but the blood large flow rates to these areas imply that a large amount of cooled blood will be returning to the core, causing systemic cooling. Avoiding head immersion is also helpful in reducing liquid use and cooling power requirements. Avoiding head immersion in ice water also avoids potential cosmetic effects to the face neck and scalp. In addition, the system described employs a disposable heat exchanger rather than ice, a sanitary disposable fluid path, an oral catheter for return of fluid to a base unit thermoelectric system, and feedback control of cooling and warming based on at least the patient core temperature.

Figure 15:
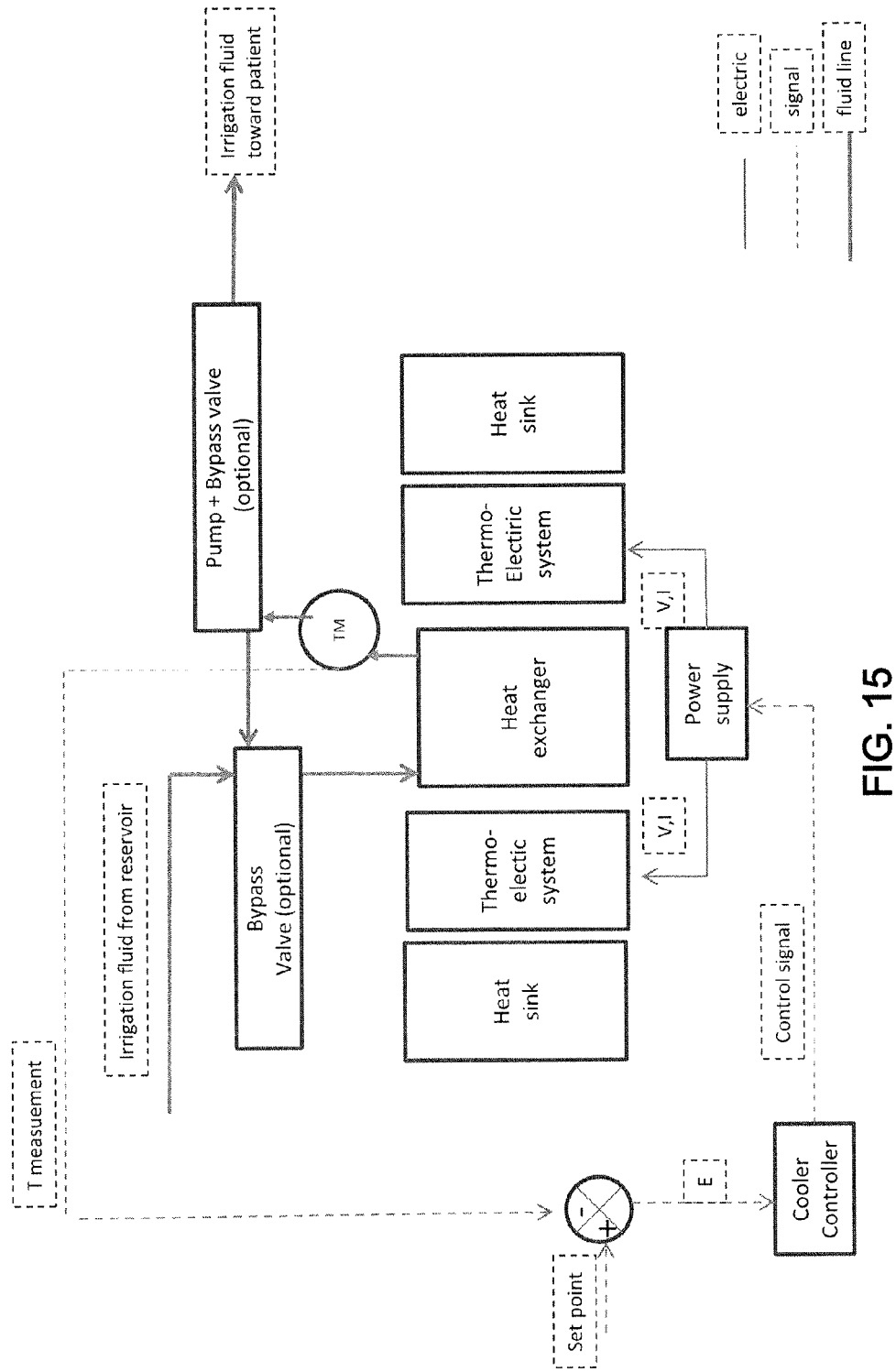
FIG. 15 is an example of a block diagram showing one embodiment of a cooling system.

FIG. 15 illustrates a re-usable cooling system that is part of the base unit, and that can be used to remove heat from the disposable heat exchanger. FIG. 15 is a representative block diagram showing one embodiment of the cooling system (the cooler) itself. The cooler can be in thermal contact with a disposable heat exchanger. The feedback control system can be configured so that power to the thermoelectric system is modulated based on the temperature of the fluid leaving the system.

An optional bypass valve arrangement is shown in FIG. 15. The bypass valve can allow fluid to be recirculated before being introduced into the patient. The bypass valve arrangement can also be placed at other parts of the fluid circuit, such as at the connection of the exit lines of the heat exchanger with the return line. The thermoelectric system(s) can include one or more individual thermoelectric elements arranged in an array, in thermal contact with a thermally conductive element (platen) designed to interface with the disposable heat exchanger. Although the platen and heat exchanger can be physically touching and in good thermal contact, they are desirably not in fluidic communication. The heat sink(s) can be in thermal contact with the hot side of the thermoelectric system and prevent the thermoelectric system form over heating due to accumulation of heat removed from the heat exchanger as well as internal generation when power is applied. A variety of heat sinks may be used.

As discussed above, a variety of heat exchangers (e.g., plate, shell, tube, etc.) can be used to provide two or more distinct paths for fluids. The cooling system and the heat exchanger can be in thermal contact and physically touching, but not in fluidic communication. Thus, heat exchange can be accomplished while avoiding contamination of the cooling unit with fluids that contact the patient.

Figure 16:
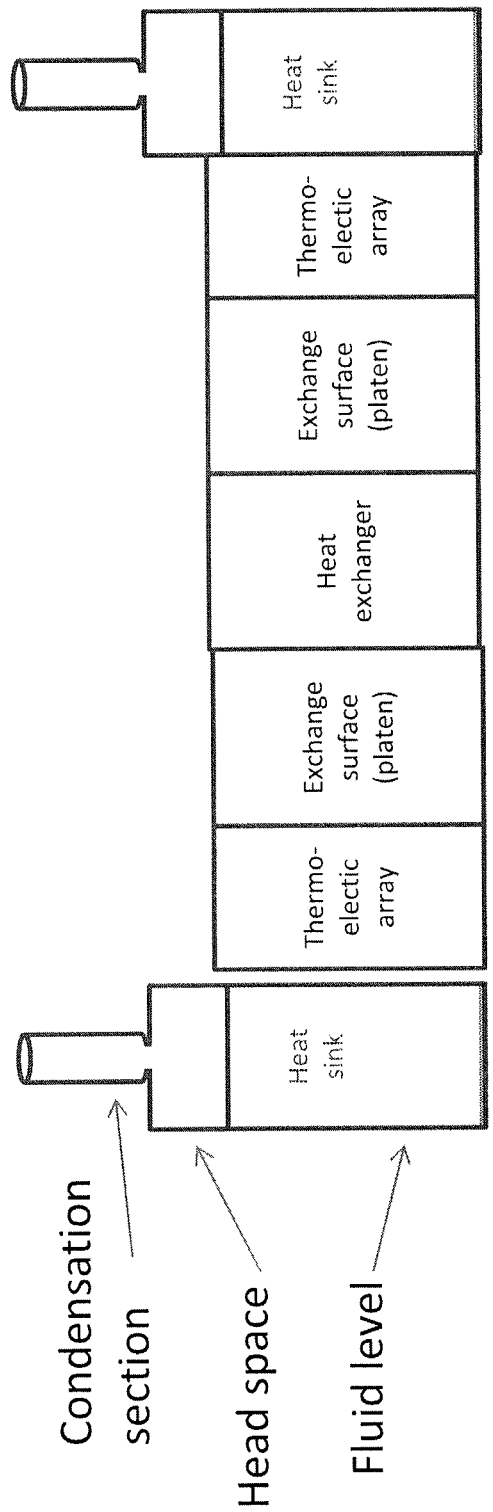
FIG. 16 is an example of a block diagram showing a cooling unit in thermal communication with a heat exchanger (e.g., disposable).

In one example, the heat exchanger can contact the exchange surfaces of the thermoelectric arrays of the cooling system in a "sandwich like" configuration. A locking mechanism or locating pins/datums can be provided to confirm proper location of the heat exchanger within the cooling unit, and lights can be provided to indicate correct placement or "ready" status. When powered, the thermoelectric arrays remove heat from the exchange surfaces and "pump" it towards the heat sinks, causing the heat sinks to warm, and the fluid to cool. The power sent to the thermoelectric arrays can be chosen so that the fluid is cooled to a temperature of 0 to 10° C. generally but may be lower in some cases. Alternative embodiments of the "sandwich" geometry feature can include, for example, one-sided thermoelectric contact or two smaller heat exchangers in tandem. In the case of 2 heat exchangers, one could be configured to serve the nasal area and one to serve the esophageal area. These heat exchangers can interface with separate cooling units or have distinct slots in one cooling unit. FIG. 16 illustrates an exemplary cooling system. Although FIG. 16 illustrates the thermoelectric array in thermal communication with a "fanless" heat sink, other heat sinks could be used, such as heat sinks that utilize finned areas and/or fans.

Figure 17:
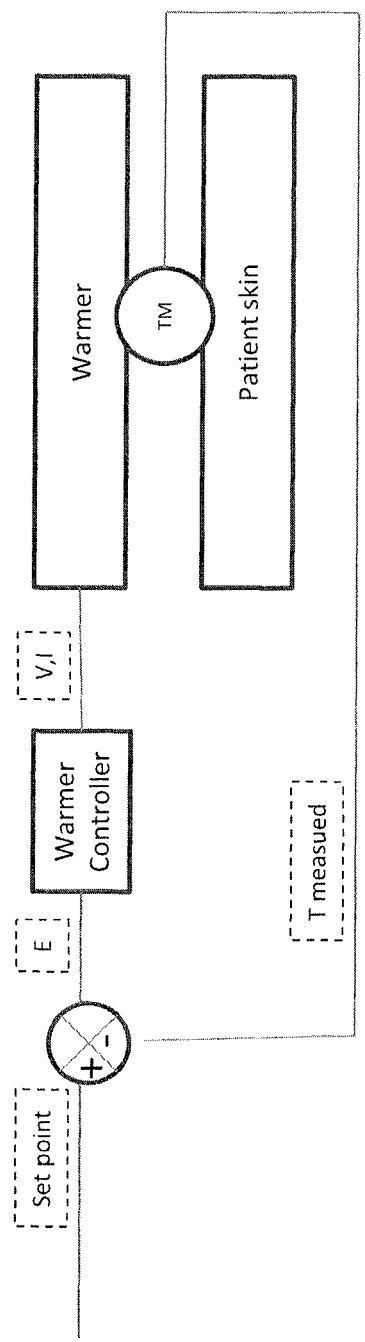
FIG. 17 is an example of a block diagram showing a simple feedback control loop designed to control a surface warming device based on the temperature at the interface between the device and the skin.

FIG. 17 illustrates a block diagram showing a simple feedback control loop designed to control a surface warming device based on the temperature at the interface between the device and the skin. The current and voltage (I, V) to the warming device can be modulated based on the difference between temperature of the device at the patient's skin and the set point provided to the controller. Of course, if desired, measurements at more than one location may be used.

A heat sink can comprise finned and fanned heat sinks typical of thermoelectric devices, where fans are used to force air over the hot surfaces, and the area for exchange is enhanced through the addition of fins. Alternatively, the heat can be removed using a fanless heat sink, by employing an arrangement similar to that of FIG. 15. The heat from the thermoelectric arrays can warm a reservoir of fluid contained in a sealed compartment with ample headspace. If the fluid is chosen with a boiling point in the range of 30 to 60° C., the current and voltage of the thermoelectric arrays can be chosen to provide a "hot side" temperature in this range. This will result in the liquid boiling as more heat is added to the heat sink reservoir side while the side contacting the single use heat exchanger is being cooled. The resulting vapor in the heat sink reservoir compartment can rise through the head space into the condensation section of the heat sink where it will condense as it encounters cooler temperatures. The heat sink fluid can continue to reflux through the heat sink compartment and thus dissipate the heat from the thermoelectric devices into the environment.

Such a heat sink can be significantly easier to clean in the case of contamination (by a spill, for example) than a finned and fanned heat sink. Also, during ordinary operation, the system can desirably accumulate and spread less dust and dirt than a fanned system. Additional advantages of fanless arrangements in a hospital environment include improved reliability and reduced noise. Also, further the condensation sections can be arranged to act as handles for the unit.

The walls of the heat sinks described herein are preferably made of a highly thermally conductive material (such as a metal) that is resistant to common chemical sterilizing solutions (such as ethanol in water, ammonium salts, etc). For example, stainless steel or other metals, with or without protective coatings, can be used.

In other embodiments, cooling techniques that are not based on thermoelectric arrays, such as a conventional refrigeration system, ice bath or endothermic chemical reaction, can be used.

The heat exchanger that interfaces with the cooling system is part of the patient interface kit and intended to be disposable. The heat exchanger is sized to provide about 5 up to 300 W of heat exchange at a flow rate of about 0.2-10 liters per minute. The actual amount of heat exchange depends on the temperature of the incoming fluid. The heat exchanger provides a serpentine flow path for the fluid to be cooled, as is typical of most heat exchanger designs. The heat exchanger is preferably constructed of a highly thermally conductive material, such as a metal, with aluminum, stainless steel, or copper being suitable choices. A box-like geometry with an internal channel of rectangular cross section is envisioned. The diameter or hydraulic diameter of the fluid path can be about 0.2-6 cm, with length of the flow path chosen to provide 100 to 300 W of heat exchange capability. Typical dimensions of the overall heat exchanger might be about 20 to 40 cm wide and 10 to 30 cm high, with a thickness of about 2 to 8 cm. These values are based on a simple serpentine fluid path, more compact arrangements are possible as the path becomes more tortuous.

The disposable heat exchanger can have one inlet for accepting fluid from the reservoir and one or more outlets for fluid to exit. In one example, one outlet for the nasal pump is provided and one outlet for the esophageal pump is provided. The portion of the heat exchanger near the inlet and outlet ends can be expanded slightly to accommodate fittings and connectors for incoming and outgoing lines. A bypass line may also be included with the disposable heat exchanger to allow recirculation of fluid through the heat exchanger while the device is in standby mode this feature is optional. In some embodiments, the walls of the heat exchanger that are not contacting the cooling elements of cooling unit will be insulated to reduce condensation and loss of cold to the environment As discussed above, various cooling fluids can be introduced into the aerodigestive tract. When maximum cooling rates and antibacterial properties are desired, the fluid formulations disclosed above can be desirable. When an extensive period of irrigation is desired, it can be advantageous to select an irrigating fluid that has an osmolality roughly equivalent to that in the tissues surrounding the aerodigestive tract so that water is not needlessly removed or added to the patient. To achieve osmotic balance, for example, a fluid formulation similar to that normally encountered by the cells lining the walls of the pharynx and esophagus can be desirable.

In one example, the formulation can be one with an electrolyte composition similar to that of ordinary saliva, including some or all of the following cations: sodium at about 1-40 mmol/l, potassium at about 5 to 60 mmol/l, calcium at about 0.5-5 mmol/l, magnesium at less than 1 mmol/l, and the following anions: chloride at 1-200 mmol/l, bicarbonate at 1-100 mmol/l, phosphate at less than 50 mmol/l and iodine at less than 10 mmol/l. This mixture can minimize chemical exchange between the body and the irrigation fluid by avoiding large osmolality or concentration gradients between the cells bordering the aerodigestive tract and the irrigating fluid. It should be noted, however, that the match need not be exact since the re-circulated fluid will equilibrate with the patient.

A slightly hypotonic formulation can also be useful because it will keep the total volume in the fluid circuit roughly constant. In more sophisticated formulations, the irrigation fluid might also be used to replace some of the mechanical and immunological functions of fluids found in the aerodigestive tract such as swallowed saliva, and other formulations can be created by adding proteins commonly found in saliva such as mucins, amylases, etc. A special dose of mucus like fluid could be added just before extubation to facilitate removal of the tubes.

Table 8 below identifies symbols used herein and in the figures.

TABLE 8

| Symbol | Meaning | Note |
|---|---|---|
| E | Error signal, indicating the difference between the measured value and the programmed set point | Used by controllers in feedback control loops |
| Flow 1 or F1 | Fluid flow rate in the nasal line | |
| Flow 2 or F2 | Fluid flow rate in the esophageal line | |
| TM | A temperature measurement device | |
| FM | A flow rate measurement device | |
| Time | A commanded time in seconds and/or duty cycle e.g. minutes/hour | Typically used to describe the amount of warming or pumping needed |
| $T^{setpoint}$ | Set point temperature commanded by the user | Typically set point for patient rectal temperature, but could be any single or multivariable measurement even, intracranial pressure, ICP |
| $T^{fluid}$ | Temperature of the fluid leaving the cooling unit, and about to enter the patient | |

TABLE 8-continued

| Symbol | Meaning | Note |
|---|---|---|
| $T^{measured}$ | Measured temperature | Typically measurement for patient rectal temperature returned to the controller, but could be any single or multivariable measurement even, intracranial pressure, ICP |
| I, V | Electric power (watts) going to coolers or warmers | |
| $q^d$ | Heat exchanged with the environment or generated by metabolism | |
| Q | Total heat exchanged with all sources other than the cooler | |
| Qw | Heat supplied by the warmer | |

The amount of warming needed can be determined by one or more of the following: monitoring the patients core temperature, considering the amount of heat being removed from the patient as determined by heat balance on incoming and outgoing fluid, energy balance on the thermoelectric cooling unit, empirical or semi-empirical relationships between multiple patient temperature measurements, and/or mathematical models. As described elsewhere, the location of warming can vary and can include, for example, the scalp, the arms, the legs, or other body surfaces. The means of warming can include circulating liquid blanket(s), hydrogel pad(s) with circulating liquids, forced air, heat lamp(s), electric blanket(s), or other suitable heat generating devices. In the case where the warming device employs circulating liquid, the warming power delivered to the patient can be estimated by monitoring the incoming and return temperatures of the warming fluid after accounting for other heat losses.

In another embodiment, a hybrid cooling system can be provided. The hybrid cooling system can include a cooling system configured to deliver (a) free flowing fluid to cool the nasal cavity as described herein and (b) balloon-contained fluid in which fluid can be circulated to cool the esophagus or at least a portion of the esophagus.

The balloon can be arranged around a catheter in an annular or partially annular fashion. An annular balloon can function to confine emesis to a large lumen of the catheter as described elsewhere herein. Alternatively, the balloon can be formed in a non-annular manner, such as with an elongated side balloon that makes good thermal contact with the arteries. A center lumen of the esophageal catheter can still function to provide stomach access and a cuff can be provided to restrict entry of emesis into the esophagus. A cuff tube can protect the lungs and suction can be applied just above the cuff to prevent stagnation as described in more detail in other embodiments.

If desired, additional fluid can be added to wash the esophagus and make good thermal contact. Fluid can exit at the mouth or, alternatively can be "dropped" into the stomach. Instead of adding additional fluid, fluid can be permitted to drip down from the nasal area to the esophagus or a portion of the esophagus.

The fluid in the balloons can be used to either maintain the esophagus in a cooled state or, alternatively, to re-warm the patient as needed.

In another embodiment, a system can be provided with a balloon that has recirculating cold fluid in the nose and free flowing fluid in the esophagus. Additional fluid can be added through an end lumen to wash the nasal cavity and make good thermal contact (e.g., like a "thermal grease"). The free flowing fluid can pile up in the esophagus and be removed through, for example, an oral return line. As in other embodiments, the lungs can be protected with a cuffed tube and suction just above the cuff can reduce/prevent stagnation.

In another embodiment, separate balloons can be provided in the nose and in the esophagus with re-circulating liquid for cooling. Additional fluid can be provided for conductivity/flushing. Again, as in other embodiments, the lungs can be protected with a cuffed tube and suction just above the cuff can reduce/prevent stagnation.

Although the methods and devices have been described in association with certain theories of their operation, the invention is not to be limited by those theories. To the extent that the invention can be understood in terms of the described structures and methods, the claims do not incorporate theories of operation unless the claims clearly indicate otherwise.

Other systems and methods can be used to help achieve and/or maintain a brain to body core temperature gradient. Such methods can be used along with the devices, systems, and methods previously described. For example, the devices, systems, and methods of the present invention can be used along with methods to reduce cerebral blood flow (e.g., 0 to 50% less than baseline). Reducing cerebral blood flow can have several advantages, such as, for example, increasing the time that the blood is in contact with anatomical regions cooled by the present methods, systems, and devices (e.g., reducing the temperature of the blood entering the brain) and reducing thermal interdependence between the brain and the body core (e.g., by increasing the amount of time cooled blood is in the brain and decreasing the amount of blood entering the brain in a given period, thus decreasing the amount of cooled blood returned to the core in relation to total cardiac output).

Various methods to reduce cerebral blood flow can be used with the present invention. For example, selective cooling the brain, itself, can result in decreased cerebral blood flow. However, in the event that selective brain cooling increases cerebral blood flow, other measures (e.g., described below) can be taken to decrease cerebral blood flow. Further, maximizing direct conductive cooling of inferior aspects of the brain (e.g., by adding surface active agents to the cooling fluid and/or decreasing cooling fluid residence time in sinuses) and/or maximizing cooling of the common carotid and vertebral arteries can reduce cerebral blood flow. Induced systemic cooling of the brain and the body in humans can also decrease cerebral blood flow.

As another example, various sedation methods can be used to decrease blood flow rate. Further, a method to reduce cerebral blood flow can comprise reducing cerebral perfusion pressure, for example, by decreasing blood pressure (systolic and diastolic), shunting blood to the body core (e.g., away from brain and meningeal arteries), and/or warming the scalp. Additionally, brief bursts or episodes of systemic cooling can reduce blood flow rate to the brain (e.g., by reducing brain metabolism). Still another example of reducing blood flow rate to the brain can be to induce hypocarbia or hyperventilation (e.g., by reduction of arterial CO2), which acts to reduce cerebral perfusion, narrow cerebral arteries, increase resistance to cerebral blood flow, and/or reduce cerebral blood volume.

In other embodiments, cerebral blood flow of a patient can be decreased by administering medications and/or agents to the patient. For example, a subject can be administered barbiturates (e.g., thiopental drip, phenobarbital, pentobarbital, methohexital, etc.), benzodiazepines (e.g., Versed, Ativan, Valium), propofol, clonidine, lidocaine, etomidate, caffeine, alcohols (e.g., ethanol), cocaine, beta-blockers (e.g., labetalol), anti-migraine medications (e.g., triptans, ergotamines, etc.), inhaled gas (e.g., isofluorane), narcotics, systemic vasoconstrictors (e.g., phenylephrine), and other select medications and/or agents. Such agents can lead to a narrowing of cerebral arteries, a reduction in cerebral blood volume, and/or a resistance to cerebral blood flow. Appropriate doses of such medications and/or agents will be understood by those of skill in the art.

In some instances, increasing intracranial pressure (e.g., by lying a subject's head and body flat, by increasing positive end-expiratory pressure using the ventilator) from low pressure levels induced by cooling therapy can also assist in reducing cerebral blood flow. Other methods of decreasing cerebral blood flow can include reducing heart rate and reducing systemic vascular resistance in relation to cerebral vascular resistance (e.g., with vasodilators and/or warming the skin). A number of these methods also decrease metabolic demand of the brain, which can further lead to reduced cerebral blood flow.

EXAMPLES

The following includes two examples of use of the present devices, systems, and methods, and various examples of features that can be included in various embodiments of the present methods and apparatuses. Examples 1 and 2 comprise recirculating chiller units and plate heat exchanges to cool fluid (e.g., as depicted in FIGS. 23A, 23B, 24A, and 25A). Fluid was withdrawn from a 10 L fluid supply reservoir using peristaltic pumps (Cole-Parmer computer-controlled digistaltic pump drive). Fluid was pumped through two heat exchangers prior to passing the fluid through the plurality of catheters. The heat exchangers were coupled to one or more recirculating chiller unites (e.g., Polyscience benchtop chillers) to cool the heat exchangers. Fluid was recovered from the patient (e.g., via vacuum suction) through oral and/or tracheal return lumens in fluid communication with the fluid supply reservoir.

In each example, the following procedures were used.
1. Mechanical Ventilation
  a. Volume Control: Vt=8 ml/kg, Rate=10/min, PEEP=5, FiO2=30%
  b. ETCO2: 30-35 Torr
  c. pH: 7.35-7.45
  d. O2 sat >96% throughout study
2. Catheters
  a. Esophogeal catheter: 3-lumen catheter
    i. Provided access to the stomach to permit gas and fluid to escape stomach.
    ii. Provided ability to inflate a balloon within esophagus to prevent cooling fluid from entering stomach.
    iii. Provided cooled liquid to the lower portion of the esophagus.
  b. Endotracheal catheter: 3-lumen catheter
    i. Provided access to the lungs to permit air to enter and exit the lungs.
    ii. Provided ability to inflate a balloon within trachea to prevent cooling fluid from entering the lungs.
    iii. Provided ability to remove cooling liquid from trachea.
  c. Two Nasal Catheters: Provided cooling fluid into aerodigestive tract.
  d. Oral Catheter: Provided ability to remove fluid accumulating in mouth.
3. Control System:
  a. System On/Off
  b. Body Set Point
  c. Pump 1 Speed
  d. Pump 2 Speed
  e. Pump Enable On/Off Example 1

A 76 kg pig was placed supine and was systemically warmed using a small Gaymar circulating water blanket and forced hot air.

Figure 23A:
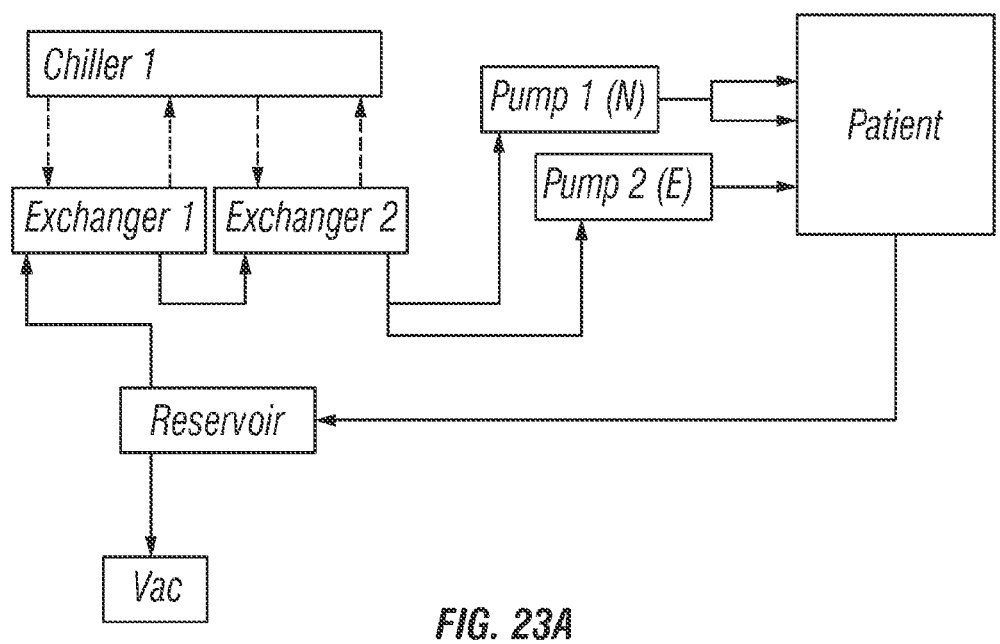
FIG. 23A depicts one embodiment of a single use fluid path system with a recirculating chiller.
Figure 23B:
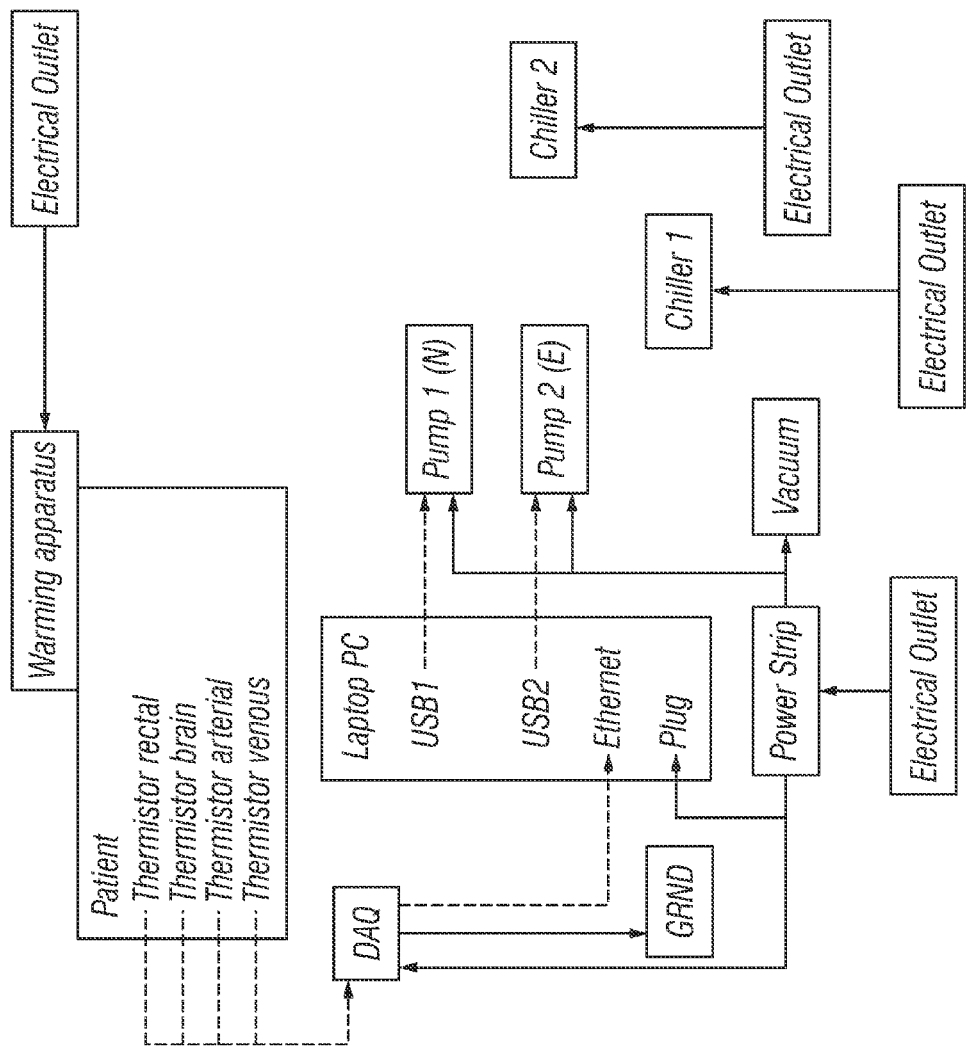
FIG. 23B depicts an electrical schematic of the embodiment of the system of FIG. 23A.
Figure 23C:
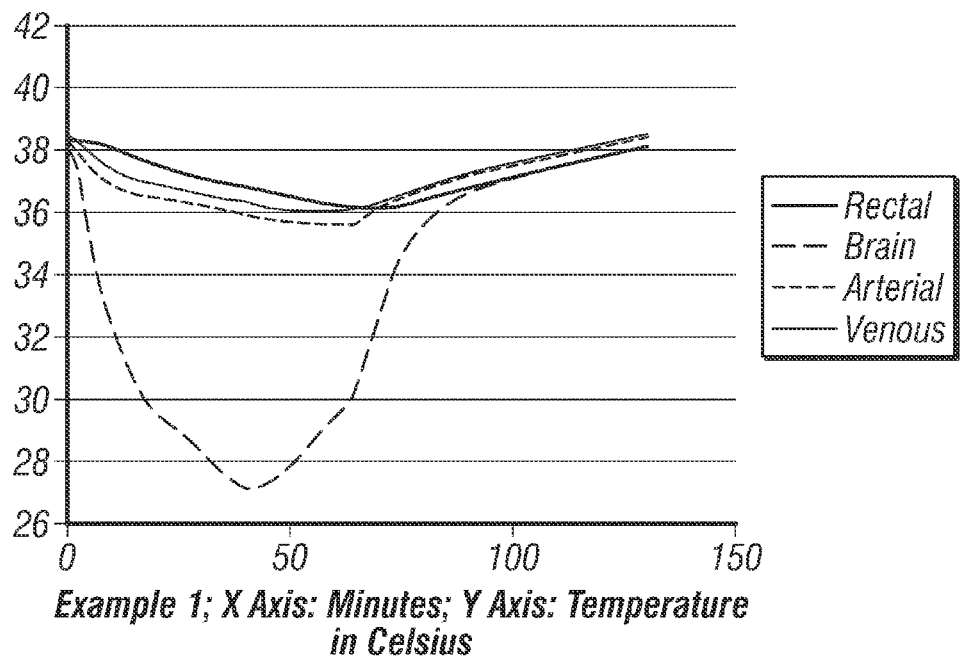
FIGS. 23C-D depict various graphical representations of temperature measurements over time using the system of FIG. 23A.

Four temperature probes were active. A needle probe was inserted into the animal's brain. Two catheter probes were inserted into the aorta and inferior vena cava, respectively. Also, a rectal temperature probe was used to monitor core temperature. Temperature probes were controlled using LabView, and pumps were controlled manually (i.e., the system was run in "open loop" mode). A fluid schematic of the system used is depicted in FIG. 23A, and an electrical schematic is depicted in FIG. 23B. After a series of set-up tests, the pig was rewarmed, and the cooling fluid was refilled. Pumps were set to 300 RPM, and cool fluid was pumped through catheters for approximately 120 minutes. The pig's initial temperatures were: Brain—38.0° C.; Aorta—38.3° C.; Vena Cava—38.4° C.; and Rectal—38.3° C. A graphical representation of results is depicted in FIG. 23C, and Table 9 displays parameters associated with this trial.

TABLE 9

| Parameter | Value |
| --- | --- |
| Time from 'Start' to 33° C. Brain | 8.68 min |
| Initial 300 RPM cooling Brain 1° C. | 3.04 min |
| Min time to cool Brain 1° C. | 1.17 min |
| Initial 300 RPM cooling Core 1° C. | 26.24 min |
| Min Rewarming time Brain 1° C. | 2.28 min |
| Min Rewarm time Core 1° C. | 48.1 min |
| Max gradient | 9.7° C. |
| Lowest T brain | 27.09° C. |
| Lowest T core | 36.13° C. |

Figure 23D:
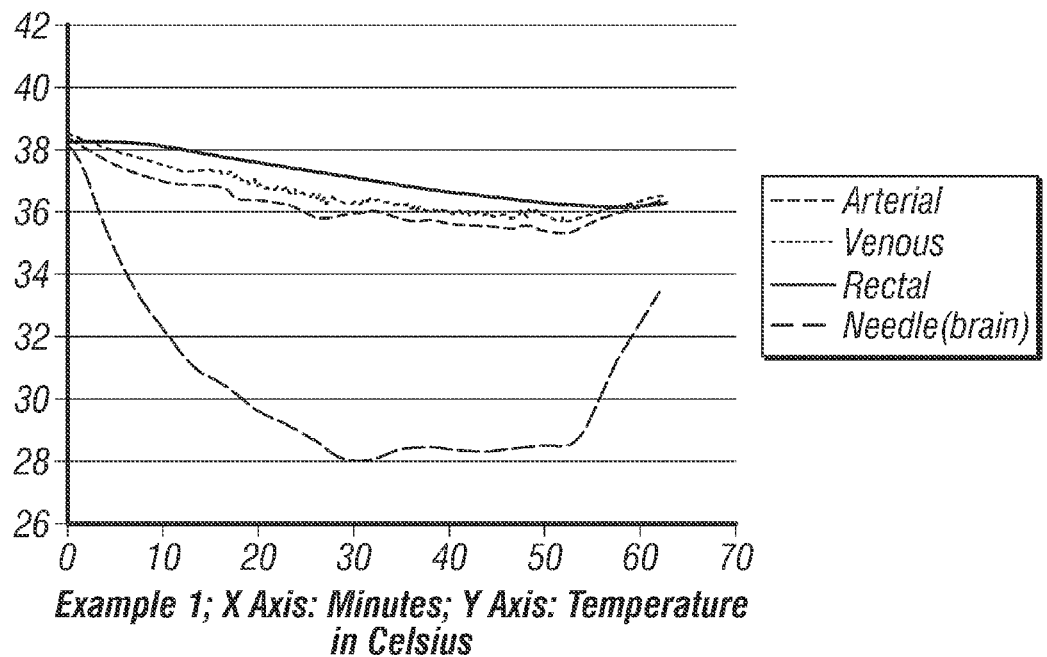

The pig was rewarmed, and the cooling fluid was refilled. Pumps were set to 600 RPM, and cool fluid was pumped through catheters for approximately 32.45 minutes. The pig's initial temperatures were: Brain—38.1° C.; Aorta—38.3° C.; Vena Cava—38.5° C.; and Rectal 38.1° C. A graphical representation of results is depicted in FIG. 23D up to a time of approximately 32.45 minutes, and Table 10 displays parameters associated with this trial.

TABLE 10

| Parameter | Value |
| --- | --- |
| Time from 'Start' to 33° C. Brain | 8.15 min |
| Initial 600 RPM cooling Brain 1° C. | 2.01 min |
| Min time too cool brain 1° C. | 1.18 min |
| Initial core cooling 1° C. | 26.75 min |
| Min rewarming time core | NA |
| Min rewarming time brain | NA |
| Max gradient | 8.95° C. |
| Lowest T brain | 28.06° C. |
| Lowest T core | 36.0° C. |

The pump speed was reduced mid-cycle from 600 RPM to 300 RPM at approximately 32.45 minutes, and cool fluid was pumped through catheters for approximately 30 more minutes. A graphical representation of results is depicted beginning at approximately 32.45 minutes in FIG. 23D, and Table 11 displays parameters associated with this trial.

TABLE 11

| Parameter | Value |
| --- | --- |
| Min brain temp after change to 300 RPM | 28.3 |
| Max gradient after change to 300 RPM | 8.36 |
| Min rewarming time core | NA |
| Min rewarming time brain 1° C. | 1.53 min |

These tests demonstrate that a variety of flow rates can be used to accomplish cooling, that cooling is rapid, that cooling is selective, that the brain returns to its former state once cooling ends, and that the results are reproducible.

Example 2

Figure 24A:
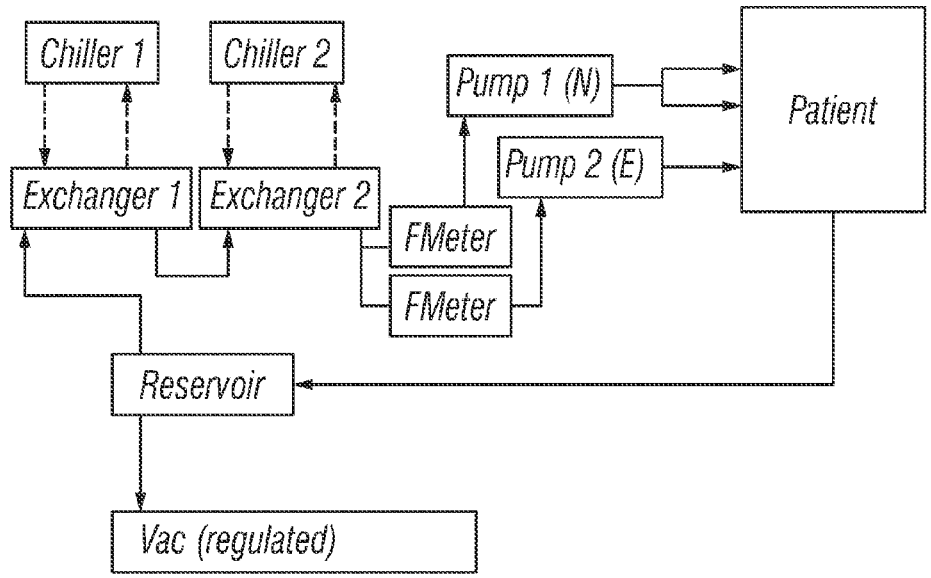
FIGS. 24A depicts another embodiment of the present systems, including two recirculating chillers and flow meters.

In Example 2, a pig of similar size was used. The cooling apparatus was similar to that used in the previous example; however, flow meters and a vacuum regulator were included. A schematic representation of the fluid system of Example 2 is depicted in FIG. 24A. The electrical system did not change from that in Example 1. A graphical representation of results of Example 2 are depicted in FIG. 24B.

Figure 24B:
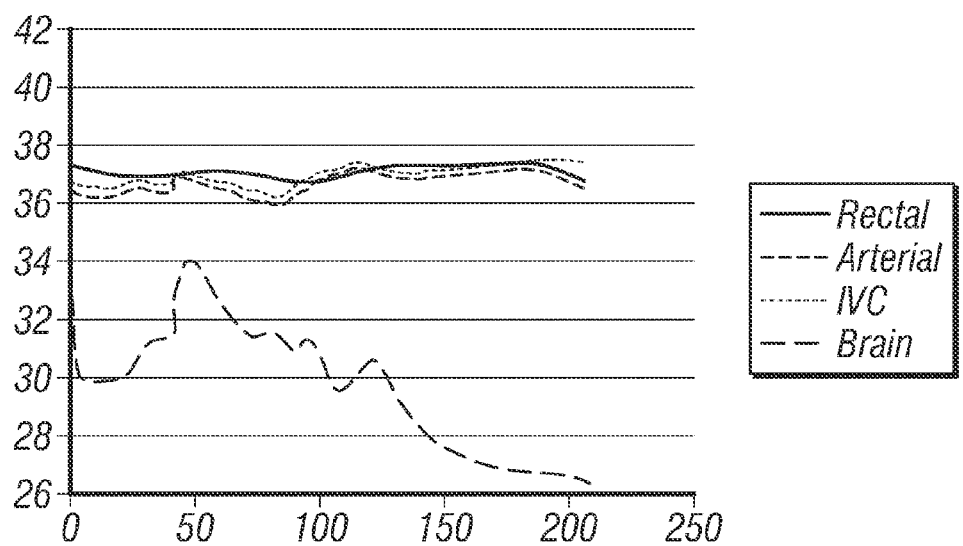
FIG. 24B depicts a graphical representations of temperature measurements over time using the system of FIG. 24A.
Figure 25A:
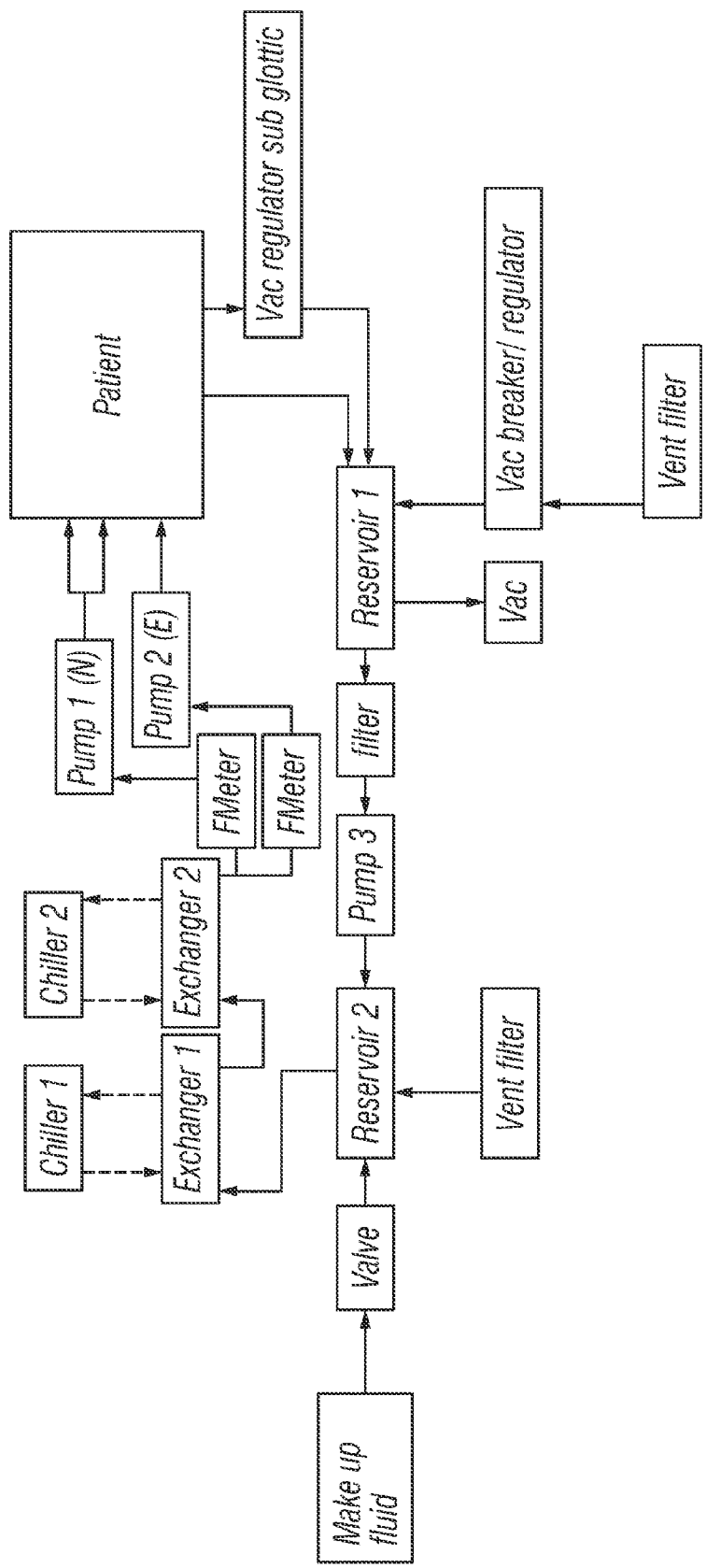
FIGS. 25A-25B depict another other embodiments of the systems of the present invention with separate fluid return and fluid supply reservoirs.
Figure 25B:
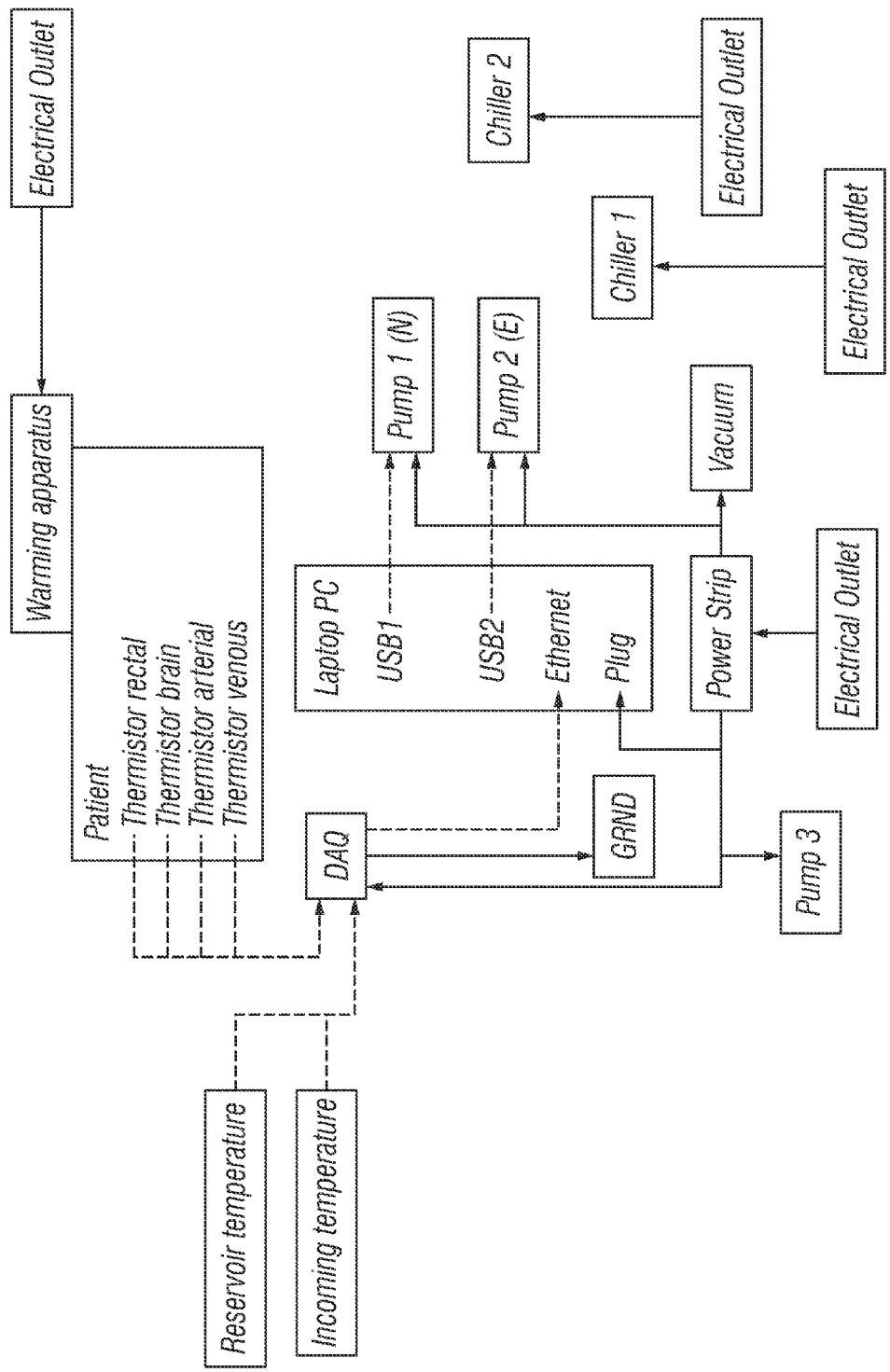

As depicted at minutes 120 to 180 of FIG. 24B, body core temperature was substantially maintained and/or increased with a counter warming device, while brain temperature decreased (e.g., increasing a brain to body core temperature gradient). A maximum brain to body core temperature gradient of approximately 10.8° C. was achieved. Addition of propofol as an anesthetic assisted in decreasing brain temperature by, for example, decreasing blood flow to the brain and/or allowing deeper equilibration of blood in the large arteries of the neck (e.g., by decreasing flow rate and velocity and increasing residence time). However, as described above, a number of other anesthetics can also be used.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The invention claimed is:

1. A method for cooling the brain, comprising:
   directing a non-nebulized free flowing fluid through a plurality of catheters into the aerodigestive tract of a patient such that at least a portion of the free flowing fluid is in direct contact with tissue of the aerodigestive tract and where the free flowing fluid cools blood flowing between the aortic arch and the brain;
   actively removing the free flowing fluid from the aerodigestive tract of the patient through at least one of the plurality of catheters; and
   recirculating at least a portion of the free flowing fluid through a heat exchanger and the aerodigestive tract where the volume of free flowing fluid directed to the aerodigestive tract is substantially equal to the volume of free flowing fluid that is actively removed from the aerodigestive tract through the plurality of catheters until reaching a brain to body core temperature gradient of at least 3° C.

2. The method of claim 1, further comprising:
   recirculating the fluid through the plurality of catheters until reaching a brain to body core temperature gradient of from 3° C. to 25° C.

3. The method of claim 1, further comprising:
   recirculating the fluid through the plurality of catheters until reaching a brain to body core temperature gradient of from 4° C. to 12° C.

4. The method of claim 1, where the fluid comprises electrolytes.

5. The method of claim 1, where the fluid comprises antibacterial agents.

6. The method of claim 1, where the fluid comprises propylene glycol.

7. The method of claim 1, where the fluid is hypertonic.

8. The method of claim 1, where the fluid comprises mucosal protectants.

9. The method of claim 1, where the brain to body core temperature gradient remains substantially constant for at least 1 hour.

10. The method of claim 1, further comprising:
    activating a warming device to warm at least a portion of the patient.

11. The method of claim 1, further comprising:
    reducing blood flow to the patient's brain.

12. The method of claim 11, where reducing blood flow to the brain comprises sedating the patient.

13. The method of claim 11, where reducing blood flow to the brain comprises decreasing blood pressure.

14. The method of claim 11, where reducing blood flow comprises administering barbiturates, propofol, benzodiazepines, lidocaine, etomidate, caffeine, alcohol, narcotics, cocaine, beta-blockers, anti-migraine medications, vasoconstrictors, and/or clonidine to the patient.

15. The method of claim 1, further comprising:
    monitoring a temperature of at least one of the patient's brain and the patient's body core.

16. The method of claim 15, where monitoring a temperature of the patient's brain comprises disposing a bolt comprising a temperature sensor in the patient's brain.

17. The method of claim 15, where monitoring a temperature of the patient's brain and the patient's body core comprises administering a magnetic resonance imaging procedure.

18. The method of claim 15, where monitoring a temperature of the patient's brain comprises inserting a temperature sensor intravenously in the jugular and positioning the temperature sensor near the brain.

19. The method of claim 1 further comprising cooling the brain without the use of a cooling reservoir that, at least partially, surrounds a patient's head.

20. A method for cooling the spinal column, comprising:
directing a non-nebulized free flowing fluid through a plurality of catheters into the aerodigestive tract of a patient such that at least a portion of the free flowing fluid is in direct contact with tissue of the aerodigestive tract and where the free flowing fluid cools blood flowing between the aortic arch and the brain;
actively removing the free flowing fluid from the aerodigestive tract of the patient; and
recirculating at least a portion of the free flowing fluid through a heat exchanger and the aerodigestive tract where the volume of free flowing fluid that is directed to the aerodigestive tract is substantially equal to the volume of free flowing fluid that is actively removed from the aerodigestive tract until reaching a spinal column to body core temperature gradient of at least 3° C.

21. An apparatus for cooling the brain, the apparatus comprising:
a first catheter configured to direct a non-nebulized free flowing fluid into an aerodigestive tract of a patient where at least a portion the free flowing fluid is in direct contact with tissue of the aerodigestive tract and where the free flowing fluid cools blood flowing between the aortic arch and the brain;
a second catheter configured to remove the free flowing fluid from the aerodigestive tract of the patient; and
a recirculation system configured to actively recirculate at least a portion of the free flowing fluid through a heat exchanger and the aerodigestive tract where the volume of free flowing fluid that is directed to the aerodigestive tract is substantially equal to the volume of free flowing fluid that is actively removed from the aerodigestive tract until reaching a brain to body core temperature gradient of at least 3° C.

22. The apparatus of claim 21, further comprising:
recirculating the fluid through the plurality of catheters until reaching a brain to body core temperature gradient of from 3° C. to 25° C.

23. The apparatus of claim 21, further comprising:
recirculating the fluid through the plurality of catheters until reaching a brain to body core temperature gradient of from 4° C. to 12° C.

24. The apparatus of claim 21, where the fluid comprises electrolytes.

25. The apparatus of claim 21, where the fluid comprises antibacterial agents.

26. The apparatus of claim 21, where the fluid comprises propylene glycol.

27. The apparatus of claim 21, where the fluid is hypertonic.

28. The apparatus of claim 21, where the fluid comprises mucosal protectants.

29. The apparatus of claim 21, where the recirculation system is configured to actively recirculate at least a portion of the free flowing fluid to maintain the brain to body core temperature gradient substantially constant for at least 1 hour.

30. The apparatus of claim 21, further comprising:
a warming device to warm at least a portion of the patient.

31. The apparatus of claim 21, further comprising a third catheter for administering barbiturates, propofol, benzodiazepines, lidocaine, etomidate, caffeine, alcohol, narcotics, cocaine, beta-blockers, anti-migraine medications, vasoconstrictors, and/or clonidine to the patient.

32. The apparatus of claim 21, further comprising a first and a second temperature sensor where the first temperature sensor measures the patient's brain temperature and the second temperature sensor measures the patient's body core temperature.

33. The apparatus of claim 32, where at least one of the first and second temperature sensors comprises an intravenous temperature sensor.

34. The apparatus of claim 33 where the at least one temperature sensor is positioned intravenously in the jugular and the temperature sensor is positioned near the brain.

35. The apparatus of claim 21, further defined as not comprising a cooling reservoir that, at least partially, surrounds a patient's head.

* * * * *